(12) United States Patent
Graupe et al.

(10) Patent No.: US 8,993,755 B2
(45) Date of Patent: *Mar. 31, 2015

(54) MODULATORS OF TOLL-LIKE RECEPTOR 7

(71) Applicant: Gilead Sciences, Inc., Foster City, CA (US)

(72) Inventors: Michael Graupe, Pacifica, CA (US); Randall L. Halcomb, Foster City, CA (US)

(73) Assignee: Gilead Sciences, Inc., Foster City ( * ) Notice: Subject to any disclaimer, the term of this patent is extended or adjusted under 35 U.S.C. 154(b) by 0 days.

This patent is subject to a terminal disclaimer.

(21) Appl. No.: 14/158,595

(22) Filed: Jan. 17, 2014

(65) Prior Publication Data
US 2014/0135492 A1    May 15, 2014

Related U.S. Application Data

(60) Continuation of application No. 13/490,696, filed on Jun. 7, 2012, now abandoned, which is a continuation of application No. 13/153,340, filed on Jun. 3, 2011, now abandoned, which is a division of application No. 12/215,598, filed on Jun. 26, 2008, now Pat. No. 7,968,544.

(60) Provisional application No. 60/937,726, filed on Jun. 29, 2007, provisional application No. 60/959,714, filed on Jul. 16, 2007.

(51) Int. Cl.
C07D 273/00    (2006.01)
C07D 473/18    (2006.01)

(52) U.S. Cl.
CPC .................... C07D 473/18 (2013.01)
USPC ........................................ 544/276

(58) Field of Classification Search
CPC .................................. C07D 473/18
See application file for complete search history.

(56) References Cited

U.S. PATENT DOCUMENTS

| | | | |
|---|---|---|---|
| 6,329,381 B1 | 12/2001 | Kurimoto et al. |
| 6,376,501 B1 | 4/2002 | Isobe et al. |
| 7,642,350 B2 | 1/2010 | Pryde |
| 2005/0043239 A1 | 2/2005 | Douangpanya et al. |
| 2006/0052403 A1 | 3/2006 | Isobe et al. |
| 2007/0190071 A1 | 8/2007 | Kurimoto et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0209524 A1 | 8/2009 | Bennet et al. |
| 2009/0324551 A1 | 12/2009 | Carson et al. |
| 2009/0325877 A1 | 12/2009 | Grunt et al. |

(Continued)

FOREIGN PATENT DOCUMENTS

| | | | |
|---|---|---|---|
| JP | 2005/089334 A | 4/2005 |
| WO | WO 99/28321 A1 | 6/1999 |

(Continued)

OTHER PUBLICATIONS

Kelley, "Journal of Medicinal Chemistry" vol. 32 (8), pp. 1757-1763 (1989).

(Continued)

Primary Examiner — Noble Jarrell
Assistant Examiner — John S Kenyon
(74) Attorney, Agent, or Firm — Kilpatrick Townsend and Stockton LLP

(57) ABSTRACT

The present application includes a compound of Formula I or II:

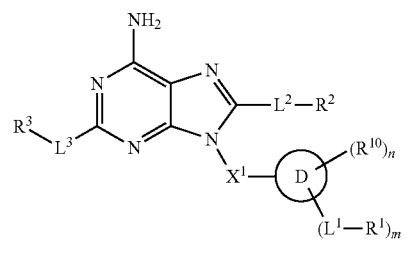

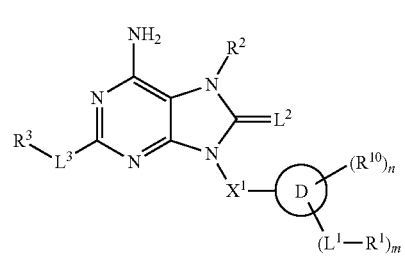

or a pharmaceutically acceptable salt, solvate, and/or ester thereof, compositions containing such compounds, therapeutic methods that include the administration of such compounds, and therapeutic methods that include the administration of such compounds with at least one additional active agent.

8 Claims, No Drawings

(56) References Cited

U.S. PATENT DOCUMENTS

| | | |
|---|---|---|
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2010/0280001 A1 | 11/2010 | Bonnert et al. |
| 2010/0298364 A1 | 11/2010 | Bennett et al. |

FOREIGN PATENT DOCUMENTS

| | | |
|---|---|---|
| WO | WO 99/32477 A1 | 7/1999 |
| WO | WO 2004/029054 A1 | 4/2004 |
| WO | WO 2005/016348 A1 | 2/2005 |
| WO | WO 2005/016349 A1 | 2/2005 |
| WO | WO 2005/067901 A2 | 7/2005 |
| WO | WO 2005/112935 A1 | 12/2005 |
| WO | WO 2005/117889 A1 | 12/2005 |
| WO | WO 2005/120511 A1 | 12/2005 |
| WO | WO 2006/089106 A2 | 8/2006 |
| WO | WO 2006/117670 A1 | 11/2006 |
| WO | WO 2007/024707 A2 | 3/2007 |
| WO | WO 2007/034817 A1 | 3/2007 |
| WO | WO 2007/034882 A1 | 3/2007 |
| WO | WO 2007/034917 A1 | 3/2007 |
| WO | WO 2007/089334 A2 | 8/2007 |
| WO | WO 2007/142755 A2 | 12/2007 |
| WO | WO 2008/004948 A1 | 1/2008 |
| WO | WO 2010/018130 A1 | 2/2010 |
| WO | WO 2010/018131 A1 | 2/2010 |
| WO | WO 2010/018132 A1 | 2/2010 |
| WO | WO 2010/018134 A1 | 2/2010 |

OTHER PUBLICATIONS

International Search Report for PCT/US2008/007955, Oct. 22, 2008.

Juricova et al., Synthesis of Base-Modified 'Abbreviated' NAD Analogues, "Collection of Czechoslovak Chemical Communications" vol. 60 (2), pp. 237-250. (1995).

New Zealand Office Action for Patent Application No. 582090 mailed Dec. 6, 2010.

MODULATORS OF TOLL-LIKE RECEPTOR 7

CROSS-REFERENCE TO RELATED APPLICATION

This application is a continuation of U.S. application Ser. No. 13/490,696, filed Jun. 7, 2012, which is a continuation of U.S. application Ser. No. 13/153,340, filed Jun. 3, 2011, which is a divisional of U.S. application Ser. No. 12/215,598, filed Jun. 26, 2008, now U.S. Pat. No. 7,968,544, which claims the benefit of U.S. Provisional Application No. 60/937,726, filed Jun. 29, 2007, and U.S. Provisional Application No. 60/959,714, filed Jul. 16, 2007, each of which is herein incorporated by reference in its entirety for all purposes.

FIELD OF THE INVENTION

This application relates generally to compounds and pharmaceutical compositions which selectively activates toll-like receptor 7 (TLR7), and methods of making and using them.

BACKGROUND OF THE INVENTION

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli*.), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), TLR7 recognizes and responds to imiquimod and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines.

SUMMARY OF THE INVENTION

The present invention is based, in part, on the discovery by the applicants that a number of small molecules can alter TLR-mediated immunostimulatory signaling. Accordingly, the present application is directed to compounds and pharmaceutical compositions, and methods for use in preventing or treating diseases or conditions associated with Toll-like receptor 7 (TLR7) activity in patients. In one embodiment, the invention comprises a compound of formula I or II:

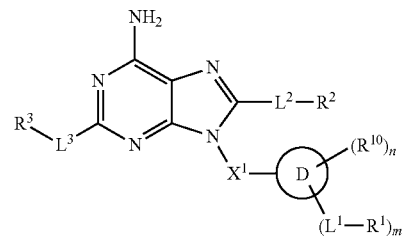

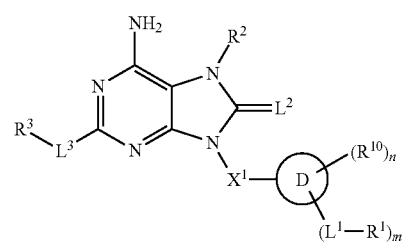

or a pharmaceutically acceptable salt thereof, wherein:

$X^1$ is —NH—, —O—, alkylene, substituted alkylene, alkenylene, substituted alkenylene, alkynylene, substituted alkynylene, carbocyclylene, substituted carbocyclylene, heterocyclylene, or substituted heterocyclylene;

D is carbocyclylene or heterocyclylene;

each $L^1$ is independently alkylene or substituted alkylene;

each $R^1$ is independently —$NR^4R^5$;

m is 1 or 2;

$L^2$ is a covalent bond, —NH—, —O—, or —S—;

$R^2$ is H, halo, alkyl, substituted alkyl, alkenyl, substituted alkenyl, carbocyclyl, substituted carbocyclyl, carbocyclylalkyl, substituted carbocyclylalkyl, arylalkyl, substituted arylalkyl, heterocyclylalkyl, substituted heterocyclylalkyl, —C(O)$R^6$, —C(O)O$R^6$, —C(O)N$R^7R^8$, —S(O)O$R^7$, —S(O)N$R^7R^8$, —S(O)$_2R^7$, —S(O)$R^7$, —S(O)$_2$O$R^7$, or —S(O)$_2$N$R^7R^8$;

$L^3$ is —NH—, —O—, —S—, —N($R^9$)C(O)—, —S(O)$_2$—, —S(O)—, or a covalent bond;

$R^3$ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

$R^4$ and $R^5$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)$R^3$, —S(O)$R^3$, —S(O)$_2R^3$, —C(O)O$R^3$, or —C(O)N$R^7R^8$; or $R^4$ and $R^5$, taken together with the nitrogen to which they are both attached, form a substituted or unsubstituted heterocycle;

$R^6$ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

R⁷ and R⁸ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl; or R⁷ and R⁸, taken together with the nitrogen to which they are both bonded, form a substituted or unsubstituted heterocycle;

R⁹ is H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

R¹⁰ is halogen, cyano, azido, nitro, alkyl, substituted alkyl, hydroxyl, amino, heteroalkyl, or substituted heteroalkyl; and n is an integer from 0 to 5; and with the following proviso:

(a) When X¹ is —CH₂—, D is 1,4-phenylene, R³-L³- is CH₃CH₂CH₂CH₂O— or CH₃—O—CH₂CH₂—O, n=0, m=1, then NR⁴R⁵ is not: (1) a 4-substituted or 4,4-disubstituted piperidine or piperazine (2) —NHCH₃;

(b) When X¹ is —CH₂—, D is 1,4-phenylene or 1,4-piperidinylene, R³-L³- is CH₃CH₂CH₂CH₂O— or CH₃—O—CH₂CH₂—O, n=0, m=1, then neither R⁴ nor R⁵ are substituted alkyl, substituted heterocycyl, or substituted benzyl; and (c) When X¹ is —CH₂—, D is 2,5-pyridylene, R³-L³- is CH₃CH₂CH₂CH₂O— or CH₃—O—CH₂CH₂—O, n=0, m=1, then NR⁴R⁵ is not pyrrolyl, piperazyl, or N(CH₃)₂.

In another embodiment, Formula I can be represented by Formula Ia:

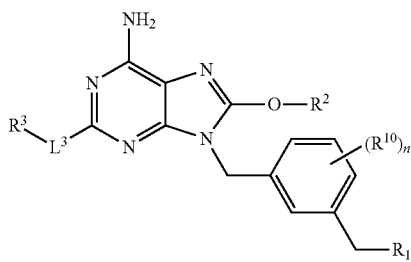

Ia or a pharmaceutically acceptable salt thereof, wherein:

R¹ is —NR⁴R⁵;

R² is H, alkyl, substituted alkyl, carbocyclyl, substituted carbocyclyl, carbocyclylalkyl, substituted carbocyclylalkyl, arylalkyl, substituted arylalkyl, heterocyclylalkyl, substituted heterocyclylalkyl, —C(O)R⁶, —C(O)OR⁶, —C(O)NR⁷R⁸, —S(O)₂OR⁷, or —S(O)₂NR⁷R⁸;

L³ is —NH—, —O—, —S—, —N(R⁹)C(O)—, —S(O)₂—, —S(O)—, or a covalent bond;

R³ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

R⁴ and R⁵ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)R³, —S(O)R³, —S(O)₂R³, —C(O)OR³, or —C(O)NR⁷R⁸; or R⁴ and R⁵, taken together with the nitrogen to which they are both attached, form a substituted or unsubstituted heterocycle;

R⁶ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

R⁷ and R⁸ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl; or R⁷ and R⁸, taken together with the nitrogen to which they are both bonded, form a substituted or unsubstituted heterocycle;

R⁹ is H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, a protecting group, or a prodrug moiety;

R¹⁰ is halogen, cyano, azido, nitro, alkyl, substituted alkyl, hydroxyl, amino, heteroalkyl, or substituted heteroalkyl; and n is an integer from 0 to 4.

In another embodiment, Formula II can be represented by Formula IIa:

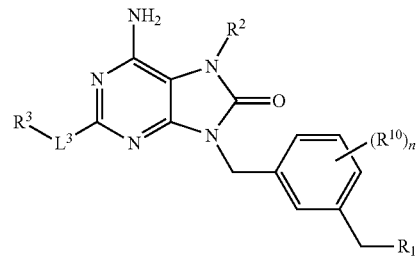

IIa or a pharmaceutically acceptable salt thereof, wherein:

R¹ is —NR⁴R⁵;

R² is H, alkyl, substituted alkyl, alkenyl, substituted alkenyl, carbocyclyl, substituted carbocyclyl, carbocyclylalkyl, substituted carbocyclylalkyl, arylalkyl, substituted arylalkyl, heterocyclylalkyl, substituted heterocyclylalkyl, —C(O)R⁶, —C(O)OR⁶, —C(O)NR⁷R⁸, —S(O)₂OR⁷, or —S(O)₂NR⁷R⁸;

L³ is —NH—, —O—, —S—, —N(R⁹)C(O)—, —S(O)₂—, —S(O)—, or a covalent bond;

R³ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

R⁴ and R⁵ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)R³, —S(O)R³, —S(O)₂R³, —C(O)OR³, or —C(O)NR⁷R⁸; or R⁴ and R⁵, taken together with the nitrogen to which they are both attached, form a substituted or unsubstituted heterocycle;

R⁶ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;

$R^7$ and $R^8$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl; or $R^7$ and $R^8$, taken together with the nitrogen to which they are both bonded, form a substituted or unsubstituted heterocycle;

$R^9$ is H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, a protecting group, or a prodrug moiety, $R^{10}$ is halogen, cyano, azido, nitro, alkyl, substituted alkyl, hydroxyl, amino, heteroalkyl, or substituted heteroalkyl; and n is 0, 1, 2, or 3.

In another embodiment, the present application provides for a pharmaceutical composition comprising at least one compound of Formula I or II, or a pharmaceutically acceptable salt, solvate, and/or ester thereof; and a pharmaceutically acceptable carrier or excipient.

In another embodiment, the present application provides for a pharmaceutical composition comprising at least one compound of Formula I or II, or a pharmaceutically acceptable salt, solvate, and/or ester thereof; at least one additional active agent; and a pharmaceutically acceptable carrier or exigent.

In another embodiment, the present application provides for a method for treating or preventing a viral infection comprising administering, to a patient in need thereof, a therapeutically effective amount of at least one compound of Formula I or II, or a pharmaceutically acceptable salt, solvate, and/or ester thereof.

In another embodiment, the present application provides for a combination pharmaceutical agent comprising:

a) a first pharmaceutical composition comprising a compound of Formula I or II, or a pharmaceutically acceptable salt, solvate, and/or ester thereof; and b) a second pharmaceutical composition comprising at least one additional active agent selected from the group consisting of interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

DETAILED DESCRIPTION

Reference will now be made in detail to certain claims of the invention, examples of which are illustrated in the accompanying structures and formulas.

While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

All documents referenced herein are each incorporated by reference in their entirety for all purposes.

Definitions

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of formula I or II" means a compound of formula I or II, or a pharmaceutically acceptable salt, solvate, ester or physiologically functional derivative thereof. Compounds of the invention also include tautomeric forms thereof, e.g., tautomeric "enols" as described herein. Similarly, with respect to isolatable intermediates such as for example, compounds of formula (2), the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene, vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., C$_2$-C$_{20}$ alkynyl), 2 to 12 carbon atoms (i.e., C$_2$-C$_{12}$ alkyne,), or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aminoalkyl" refers to an acyclic alkyl radical in which one of the hydrogen atoms bonded to a carbon atom, typically a terminal or sp$^3$ carbon atom, is replaced with an amino radical.

"Amidoalkyl" refers to an acyclic alkyl radical in which one of the hydrogen atoms bonded to a carbon atom, typically a terminal or sp$^3$ carbon atom, is replaced with a —NR$^a$COR$^b$ group where R$^a$ is hydrogen or alkyl and R$^b$ is alkyl, substituted alkyl, aryl, or substituted aryl as defined herein, e.g., —(CH$_2$)$_2$—NHC(O)CH$_3$, —(CH$_2$)$_3$—NH—C(O)—CH$_3$, and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or spa carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$^2$, —N$_3$, —NHC(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —P(O)(OR)(O), —C(=O)R, —C(S)R, —C(O)OR, —C(O)O$^-$, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; Principles of *Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

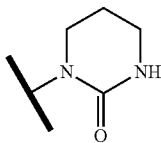

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, azetidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

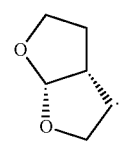

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or spa carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 2 to 20 carbon atoms, e.g., the alkyl portion of the arylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 2 to 20 carbon atoms, e.g., the alkenyl portion of the heterocyclyl alkenyl group comprises 1 to 6 carbon atoms and the heterocyclyl moiety comprises 1 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 2 to 20 carbon atoms, e.g., the alkynyl portion of the heterocyclyl alkynyl group comprises 1 to 6 carbon atoms and the heterocyclyl moiety comprises 1 to 14 carbon atoms.

"Heteroaryl" refers to a monovalent aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo (4,5), (5,5), (5,6) or (6,6) system, or 9 or 10 ring atoms arranged as a bicyclo (5,6) or (6,6) system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, etc.

"Carbocyclylene" refers to a carbocyclyl or carbocycle as defined above having two monovalent radical centers derived by the removal of two hydrogen atoms from the same or two different carbon atoms of a parent carbocyclyl. Typical carbocyclylene radicals include, but are not limited to, phenylene.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-5-aryl, -alkylene-5-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)— thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)— pyrimidyl, —CH(CH$_3$)-pyrazyl, etc.

The term "optionally substituted" in reference to a particular moiety of the compound of Formula I (e.g., an optionally substituted aryl group) refers to a moiety having 0, 1, 2, or more substituents.

"Ester thereof" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. Esters can also include esters—as described above—of "tautomeric enols", e.g. as shown below:

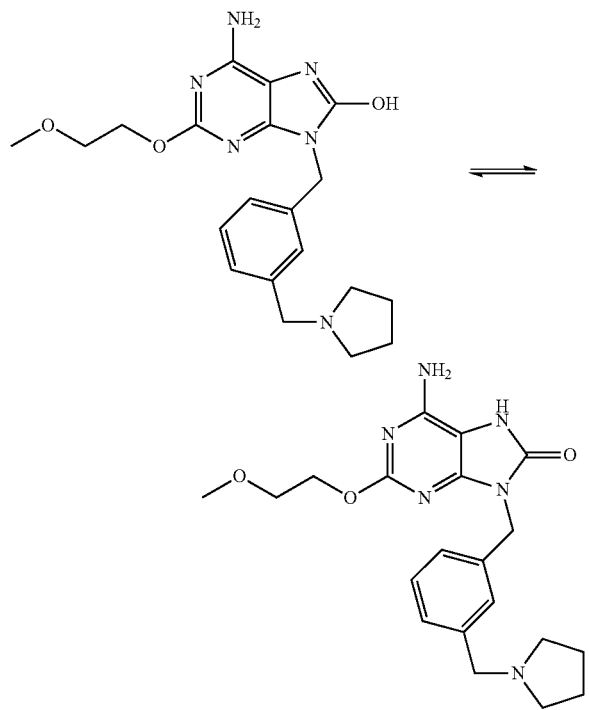

The term "ester thereof" includes but is not limited to pharmaceutically acceptable esters thereof.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereo-selection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, N.Y., 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I or II

In one embodiment, the present application provides compounds according to Formula I or II, as described herein.

In each of the embodiments herein, the following provisos apply when applicable:

(a) When $X^1$ is —$CH_2$—, D is 1,4-phenylene, $R^3$-$L^3$- is $CH_3CH_2CH_2CH_2O$— or $CH_3$—O—$CH_2CH_2$—O, n=0, m=1, then $NR^4R^5$ is not: (1) a 4-substituted or 4,4-disubstituted piperidine or piperazine (2) —$NHCH_3$;

(b) When $X^1$ is —$CH_2$—, D is 1,4-phenylene or 1,4-piperidinylene, $R^3$-$L^3$- is $CH_3CH_2CH_2CH_2O$— or $CH_3$—O—$CH_2CH_2$—O, n=0, m=1, then neither $R^4$ nor $R^5$ are substituted alkyl, substituted heterocycyl, or substituted benzyl; and (c) When $X^1$ is —$CH_2$—, D is 2,5-pyridylene, $R^3$-$L^3$- is $CH_3CH_2CH_2CH_2O$— or $CH_3$—O—$CH_2CH_2$—O, n=0, m=1, then $NR^4R^5$ is not pyrrolyl, piperazyl, or $N(CH_3)_2$.

The compounds of the present invention do not include any of the compounds disclosed in WO 07/034,817, WO 07/034,917, U.S. Patent Application Publication 2006/0052403, JP 2005/089334, or U.S. Pat. No. 6,329,381, each of which is incorporated by reference in its entirety.

The definitions and substituents for various genus and subgenus of the present compounds are described and illustrated herein. It should be understood by one skilled in the art that any combination of the definitions and substituents described above should not result in an inoperable species or compound.

"Inoperable species or compounds" means compound structures that violates relevant scientific principles (such as, for example, a carbon atom connecting to more than four covalent bonds) or compounds too unstable to permit isolation and formulation into pharmaceutically acceptable dosage forms. For example, it is understood to one skilled in the art that the definition of $L^2$ as a covalent bond only applies to Formula I, and not to Formula II.

Similarly, the skilled artisan will understand that when $L^2$ is —NH—, —O—, or —S—, in Formula II, $L^2$ defines a =NH (imine), =O (carbonyl), or =S (thiocarbonyl) group.

In one embodiment of Formula I or II, $X^1$ is alkylene or substituted alkylene; wherein the substituted alkylene comprises an alkylene substituted with one or more substituents selected from the group consisting of halo, hydroxyl, amino, heteroalkyl, substituted heteroalkyl, cyano, azido, nitro, alkyl, substituted alkyl, and combinations thereof.

In another embodiment of Formula I or II, m is 1.

In another embodiment of Formula I or II, $L^1$ is —$CH_2$— or —$CH_2CH_2$—.

In another embodiment of Formula I or II, $R^1$ is independently —$NR^4R^5$; and $R^4$ and $R^5$, taken together with the nitrogen to which they are both attached, form a substituted or unsubstituted heterocycle.

In another embodiment of Formula I or II, $R^1$ is independently —$NR^4R^5$; and $R^4$ and $R^5$, taken together with the nitrogen to which they are both attached, form a substituted or unsubstituted heterocycle; wherein the heterocycle is a 4- to 8-membered monocyclic fully saturated or partially unsaturated ring containing at least one hetero atom selected from N, O, and S; or a 8- to 12-membered fused bicyclic fully saturated or partially unsaturated ring containing at least one hetero atom selected from N, O, and S.

In another embodiment of Formula I or II, $R^1$ is independently —$NR^4R^5$; and $R^4$ and $R^5$, taken together with the nitrogen to which they are both attached, form a substituted or unsubstituted heteroaryl.

In another embodiment of Formula I or II, $R^1$ is independently —$NR^4R^5$; and $R^4$ is H, alkyl, substituted alkyl, carbocyclylalkyl, substituted carbocyclylalkyl; and $R^5$ is aryl, substituted aryl, heteroaryl, substituted heteroaryl, heterocyclylalkyl, substituted heterocyclylalkyl, —C(O)H, —C(O)$R^3$, —C(O)O$R^3$, or —C(O)N$R^7R^8$.

In another embodiment of Formula I or II, $R^1$ is independently —$NR^4R^5$; $R^4$ is H or carbocyclylalkyl; and $R^5$ is alkyl, substituted alkyl, carbocyclylalkyl, or substituted carbocyclylalkyl.

In another embodiment of Formula I or II, D is arylene or heteroarylene.

In another embodiment of Formula I or II, $L^2$ is —O—.

In one embodiment of Formula I, -$L^2$-$R^2$ is —OH.

In another embodiment of Formula I or II, $L^2$ is —O—; and $R^2$ is —C(O)$R^6$, —C(O)O$R^6$, —C(O)N$R^7R^8$, —S(O)O$R^7$, —S(O)N$R^7R^8$, —S(O)$_2$O$R^7$, or —S(O)$_2$N$R^7R^8$.

In another embodiment of Formula I or II, $R^2$ is —C(O)OCH$_3$, —C(O)OCH$_2$CH$_3$, —C(O)OCH(CH$_3$)$_2$, —C(O)NHCH$_3$, —C(O)NHCH$_2$CH$_3$, —C(O)NHCH(CH$_3$)$_2$.

In another embodiment of Formula I or II, $L^2$ is —O—; and $R^2$ is alkyl, substituted alkyl, cyclylalkyl, substituted cyclylalkyl, aryl, substituted aryl, arylalkyl, substituted arylalkyl, heterocyclylalkyl, or substituted heterocyclylalkyl.

In another embodiment of Formula I or II, $R^2$ is methyl, ethyl, n-propyl, isopropyl, n-butyl, cyclopropyl, methylcyclopropyl, cyclopropylmethylene, benzyl, or methoxybezyl.

In another embodiment of Formula I or II, $L^3$ is —O—.

In another embodiment of Formula I or II, $R^3$ is alkyl, substituted alkyl, heteroalkyl, or substituted heteroalkyl.

In another embodiment of Formula I or II, -$L^3$-$R^3$ is —O-alkyl or —O-alkylene-O-alkyl.

In another embodiment of Formula I or II, -$L^3$-$R^3$ is —OCH$_2$CH$_2$OCH$_3$ or —OCH$_2$CH$_2$CH$_2$CH$_3$.

In another embodiment of Formula I, $R^4$ and $R^5$ are not each simultaneously H or alkyl.

In another embodiment of the present invention, Formula I is represented by Formula Ia:

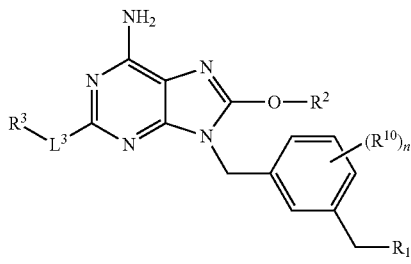

or a pharmaceutically acceptable salt thereof, wherein:
$R^1$ is —$NR^4R^5$;
$R^2$ is H, alkyl, substituted alkyl, carbocyclyl, substituted carbocyclyl, carbocyclylalkyl, substituted carbocyclylalkyl, arylalkyl, substituted arylalkyl, heterocyclylalkyl, substituted heterocyclylalkyl, —C(O)$R^6$, —C(O)O$R^6$, —C(O)$NR^7R^8$, —S(O)$_2$O$R^7$, or —S(O)$_2$$NR^7R^8$;
$L^3$ is —NH—, —O—, —S—, —N($R^9$)C(O)—, —S(O)$_2$—, —S(O)—, or a covalent bond;
$R^3$ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;
$R^4$ and $R^5$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)$R^3$, —S(O)$R^3$, —S(O)$_2$$R^3$, —C(O)O$R^3$, or —C(O)$NR^7R^8$; or
$R^4$ and $R^5$, taken together with the nitrogen to which they are both attached, form a substituted or unsubstituted heterocycle;
$R^6$ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;
$R^7$ and $R^8$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl; or
$R^7$ and $R^8$, taken together with the nitrogen to which they are both bonded, form a substituted or unsubstituted heterocycle;
$R^9$ is H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, a protecting group, or a prodrug moiety,
$R^{10}$ is halogen, cyano, azido, nitro, alkyl, substituted alkyl, hydroxyl, amino, heteroalkyl, or substituted heteroalkyl; and
n is an integer from 0 to 4.

In one embodiment of Formula Ia, $R^1$ is $NR^4R^5$; and $R^4$ and $R^5$, taken together with the nitrogen to which they are both attached, form a substituted or unsubstituted heterocycle.

In another embodiment of Formula Ia, $R^1$ is $NR^4R^5$; and $R^4$ and $R^5$, taken together with the nitrogen to which they are both attached, form a substituted or unsubstituted heterocycle; wherein the heterocycle is a 4- to 8-membered monocyclic fully saturated, partially unsaturated, or heteroaryl ring containing at least one hetero atom selected from N, O, and S; or a 8- to 12-membered fused bicyclic fully saturated or partially unsaturated ring containing at least one hetero atom selected from N, O, and S.

In another embodiment of Formula Ia, the heterocycle is selected from the group consisting of:

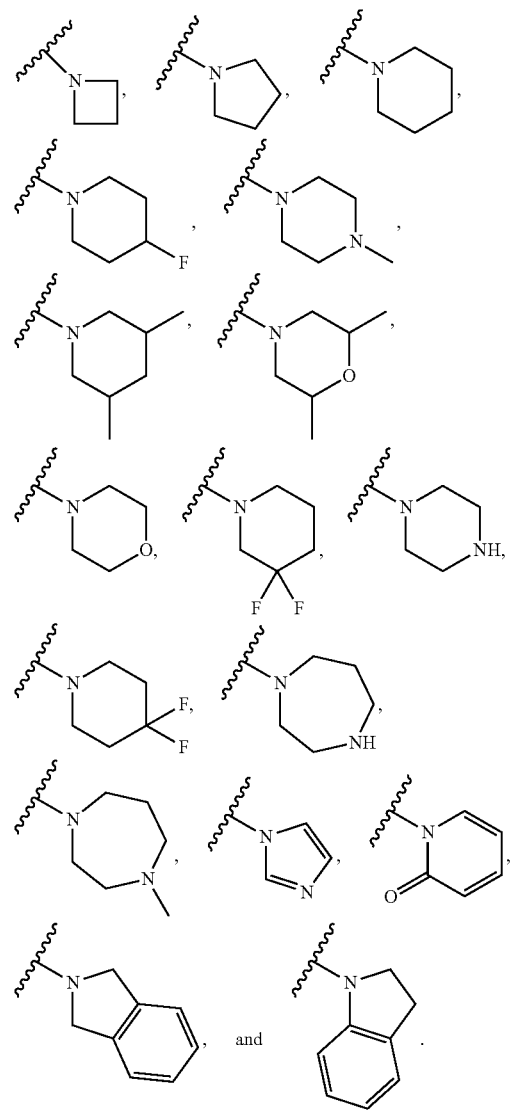

and

In another embodiment of Formula Ia, $R^1$ is $NR^4R^5$; $R^4$ is H, alkyl, substituted alkyl, carbocyclylalkyl, substituted carbocyclylalkyl; and $R^5$ is carbocyclyl, substituted carbocyclyl, carbocyclylalkyl, substituted carbocyclylalkyl, aryl, substituted aryl, heteroaryl, substituted heteroaryl, heterocyclylalkyl, substituted heterocyclylalkyl, —C(O)H, —C(O)$R^3$, —C(O)O$R^3$, or —C(O)$NR^7R^8$.

In another embodiment of Formula Ia, $R^4$ is H, methyl, ethyl, n-propyl, iso-propyl, n-butyl, cyclopropyl, or cyclopropylmethylenyl, $R^5$ is phenyl, pyridinyl, —C(O)CH$_3$, —C(O)OCH$_3$, —C(O)CH$_2$CH$_3$, or —C(O)OCH$_2$CH$_3$.

In another embodiment of Formula Ia, $R^1$ is $NR^4R^5$; $R^4$ is H; and $R^5$ is alkyl, substituted alkyl, carbocyclylalkyl, substituted carbocyclylalkyl.

In another embodiment of Formula Ia, $R^1$ is independently —$NR^4R^5$; $R^4$ is H; and $R^5$ is alkyl, substituted alkyl, carbocyclylalkyl, or substituted carbocyclylalkyl.

In another embodiment of Formula Ia, $R^1$ is independently —$NR^4R^5$; $R^4$ is H; and $R^5$ is selected from the group consisting of

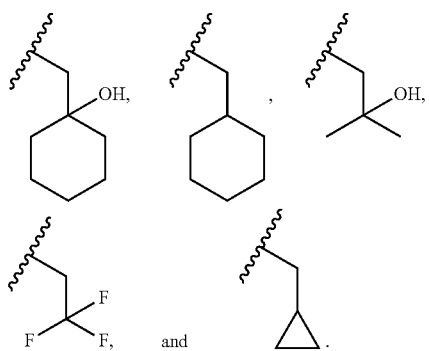

In another embodiment of Formula Ia, $R^2$ is H.

In another embodiment of Formula Ia, $R^2$ is —C(O)$R^6$, —C(O)O$R^6$, —C(O)N$R^7R^8$, —S(O)O$R^7$, —S(O)N$R^7R^8$, —S(O)$_2$O$R^7$, or —S(O)$_2$N$R^7R^8$.

In another embodiment of Formula Ia, $R^2$ is —C(O)OCH$_3$, —C(O)OCH$_2$CH$_3$, —C(O)OCH(CH$_3$)$_2$, —C(O)NHCH$_3$, —C(O)NHCH$_2$CH$_3$, —C(O)NHCH(CH$_3$)$_2$.

In another embodiment of Formula Ia, $R^2$ is alkyl, substituted alkyl, cyclylalkyl, substituted cyclylalkyl, aryl, substituted aryl, arylalkyl, substituted arylalkyl, heterocyclylalkyl, or substituted heterocyclylalkyl.

In another embodiment of Formula Ia, $R^2$ is methyl, ethyl, n-propyl, isopropyl, n-butyl, cyclopropyl, methylcyclopropyl, cyclopropylmethylene, benzyl, or methoxybezyl.

In another embodiment of Formula Ia, $L^3$ is —O—.

In another embodiment of Formula Ia, -$L^3$-$R^3$ is —O-alkyl, —O-(substituted alkyl), —O-carbocyclyl, —O-heterocyclyl, —O-carbocyclylalkyl, —O-heterocyclylalkyl, or —O-alkylene-O-alkyl. In this embodiment, it is preferred that $R^2$ is H. It is further preferred that $R^1$ is $NR^4R^5$ and $R^4$ and $R^5$, taken together with the nitrogen to which they are both attached, form a heterocycle selected from the group consisting of:

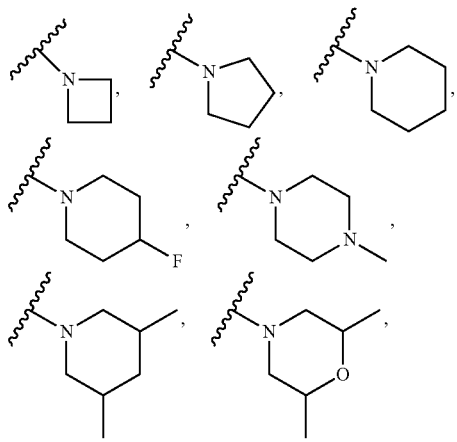

-continued

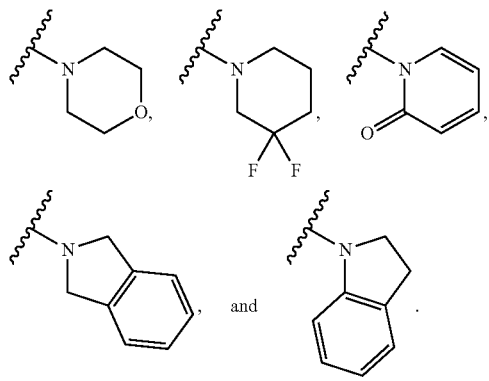

In another embodiment of Formula Ia, -$L^3$-$R^3$ is —OCH$_2$CH$_2$OCH$_3$, —OCH$_2$CH$_2$CH$_2$CH$_3$, —OCH$_2$CH$_2$CF$_3$, —OCH$_2$CF$_2$CF$_3$, —OCH$_2$CH(CH$_3$)$_2$, —OCH$_2$CF$_3$,

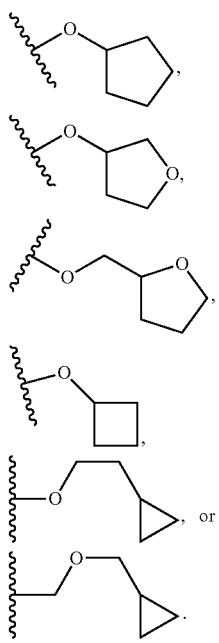

In this embodiment, it is preferred that $R^2$ is H. It is further preferred that $R^1$ is $NR^4R^5$ and $R^4$ and $R^5$, taken together with the nitrogen to which they are both attached, form a heterocycle selected from the group consisting of:

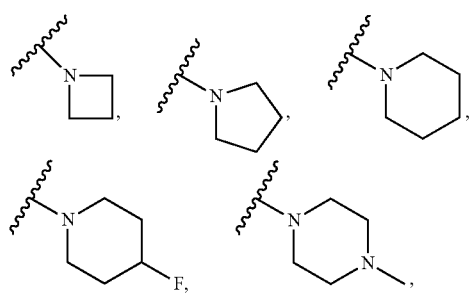

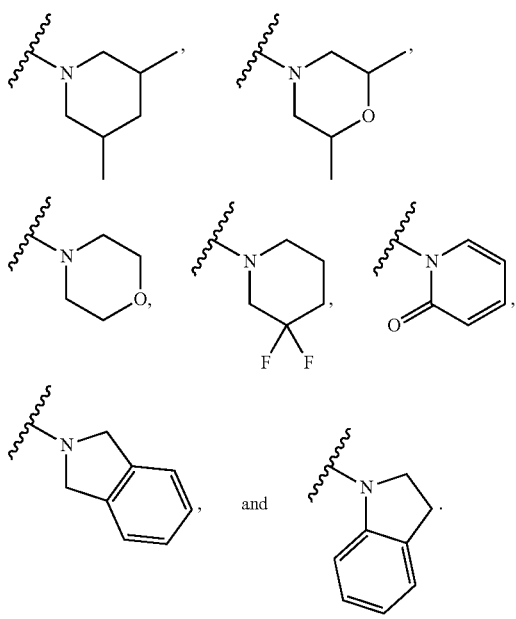

In another embodiment of Formula Ia, $R^1$ is —$NR^4R^5$; $R^2$ is H, —C(O)$R^6$, —C(O)O$R^6$, —C(O)$NR^7R^8$, —S(O)$_2$O$R^7$, or —S(O)$_2NR^7R^8$; $L^3$ is —O—; $R^3$ is alkyl, substituted alkyl, heteroalkyl, substituted heteroalkyl, carbocyclyl, heterocyclyl, carbocyclylalkyl, heterocyclylalkyl; and $R^4$ and $R^5$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)$R^3$, —S(O)$R^3$, —S(O)$_2R^3$, —C(O)O$R^3$, or —C(O)$NR^7R^8$; or $R^4$ and $R^5$, taken together with the nitrogen to which they are both attached, form a substituted or unsubstituted heterocycle.

In another embodiment of Formula Ia, $R^4$ and $R^5$ are not each simultaneously H or alkyl.

In another embodiment of Formula Ia, -$L^3$-$R^3$ is —OCH$_2$CH$_2$OCH$_3$, —OCH$_2$CH$_2$CH$_3$, —OCH$_2$CH$_2$CH$_2$CH$_3$, -Oi-butyl, -Oc-butyl, -Oc-pentyl, —OCH$_2$c-propyl, —OCH$_2$c-butyl, —OCH$_2$CH$_2$c-propyl, —OCH$_2$CH$_2$CH$_2$CH$_2$OH, —OCH$_2$CF$_3$, —OCH$_2$CH$_2$CF$_3$, —OCH$_2$CH$_2$CH$_2$CF$_3$, or (tetrahydrofuran-2-yl)methoxy.

In another embodiment of Formula Ia, -$L^3$-$R^3$ is —OCH$_2$CH$_2$OCH$_3$, —OCH$_2$CH$_2$CH$_2$CH$_3$, —OCH$_2$CH$_2$CF$_3$, —OCH$_2$CH$_2$CH$_2$CH$_2$OH, -Oi-butyl, —OCH$_2$CH$_2$c-propyl, or —OCH$_2$c-propyl. In still another embodiment, -$L^3$-$R^3$ is as defined immediately previously, $R^2$ is H, and $R^1$ is $NR^4R^5$ and $R^4$ and $R^5$, taken together with the nitrogen to which they are both attached, form a heterocycle selected from the group consisting of:

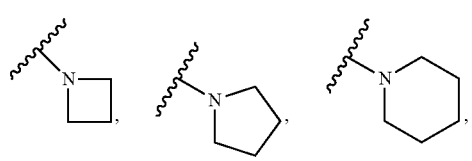

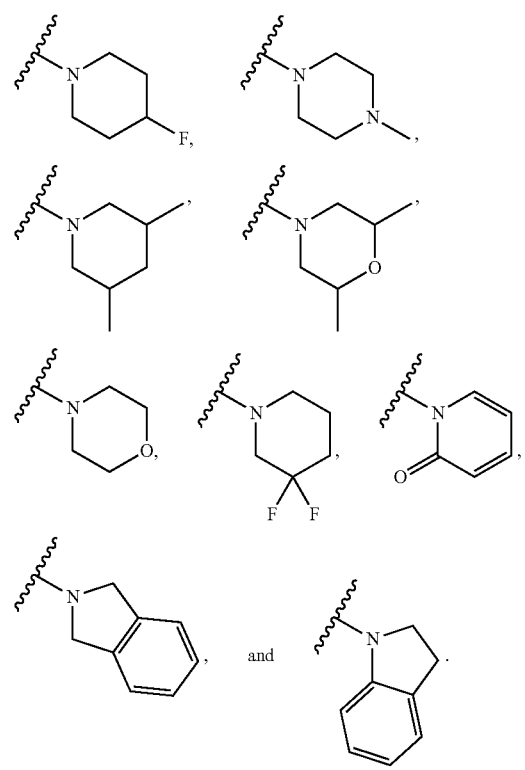

In another embodiment of Formula Ia, -$L^3$-$R^3$ is —OCH$_2$CH$_2$CH$_2$CH$_3$, —OCH$_2$CH$_2$OCH$_3$, —OCH$_2$CH$_2$CF$_3$, —OCH$_2$CH$_2$CH$_2$CH$_2$OH, or —OCH$_2$c-propyl. In still another embodiment, -$L^3$-$R^3$ is as defined immediately previously, $R^2$ is H, and $R^1$ is $NR^4R^5$ and $R^4$ and $R^5$, taken together with the nitrogen to which they are both attached, form a heterocycle selected from the group consisting of:

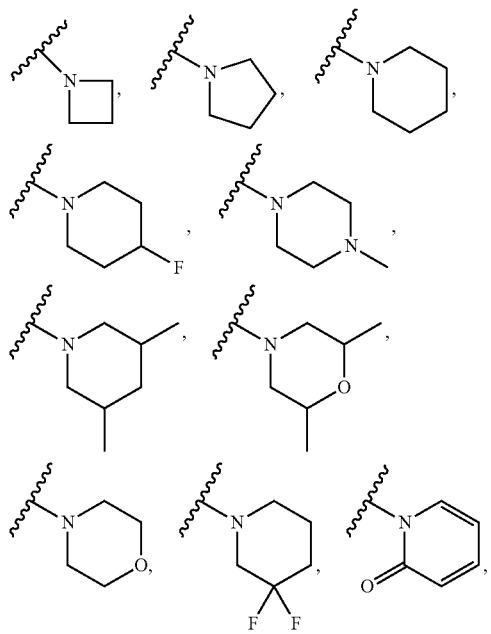

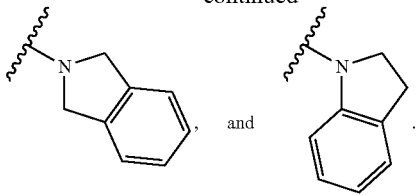

In a further embodiment -L³-R³ is —OCH₂CH₂CH₂CH₃.

In one embodiment of the present invention, Formula II is represented by Formula IIa:

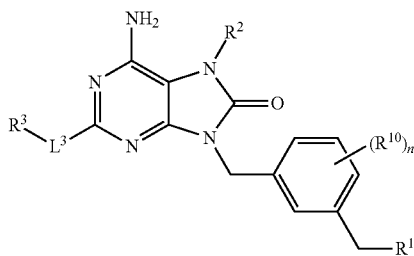

or a pharmaceutically acceptable salt thereof, wherein:
R¹ is —NR⁴R⁵;
R² is H, alkyl, substituted alkyl, alkenyl, substituted alkenyl, carbocyclyl, substituted carbocyclyl, carbocyclylalkyl, substituted carbocyclylalkyl, arylalkyl, substituted arylalkyl, heterocyclylalkyl, substituted heterocyclylalkyl, —C(O)R⁶, —C(O)OR⁶, —C(O)NR⁷R⁸, —S(O)₂OR⁷, or —S(O)₂NR⁷R⁸;
L³ is —NH—, —O—, —S—, —N(R⁹)C(O)—, —S(O)₂—, —S(O)—, or a covalent bond;
R³ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;
R⁴ and R⁵ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)R³, —S(O)R³, —S(O)₂R³, —C(O)OR³, or —C(O)NR⁷R⁸; or
R⁴ and R⁵, taken together with the nitrogen to which they are both attached, form a substituted or unsubstituted heterocycle;
R⁶ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;
R⁷ and R⁸ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl; or
R⁷ and R⁸, taken together with the nitrogen to which they are both bonded, form a substituted or unsubstituted heterocycle;

R⁹ is H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, a protecting group, or a prodrug moiety,
R¹⁰ is halogen, cyano, azido, nitro, alkyl, substituted alkyl, hydroxyl, amino, heteroalkyl, or substituted heteroalkyl; and
n is 0, 1, 2, or 3.

In one embodiment of Formula IIa, R¹ is NR⁴R⁵; and R⁴ and R⁵, taken together with the nitrogen to which they are both attached, form a substituted or unsubstituted heterocycle.

In another embodiment of Formula IIa, R¹ is NR⁴R⁵; and R⁴ and R⁵, taken together with the nitrogen to which they are both attached, form a substituted or unsubstituted heterocycle; wherein the heterocycle is a 4- to 6-membered monocyclic fully saturated or partially unsaturated ring containing at least one hetero atom selected from N, O, and S; or a 10- to 12-membered fused bicyclic fully saturated or partially unsaturated ring containing at least one hetero atom selected from N, O, and S.

In another embodiment of Formula IIa, the heterocycle is selected from the group consisting of:

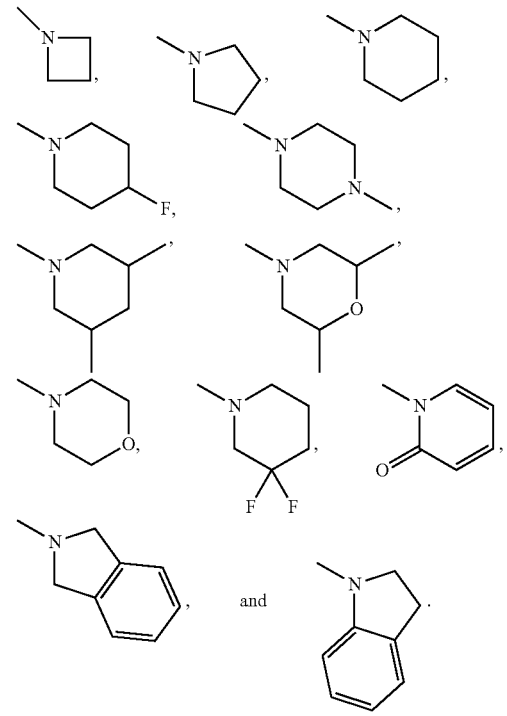

In another embodiment of Formula IIa, R¹ is NR⁴R⁵; R⁴ is H, alkyl, substituted alkyl, carbocyclylalkyl, substituted carbocyclylalkyl; and R⁵ is carbocyclyl, substituted carbocyclyl, carbocyclylalkyl, substituted carbocyclylalkyl, aryl, substituted aryl, heteroaryl, substituted heteroaryl, heterocyclylalkyl, substituted heterocyclylalkyl, —C(O)H, —C(O)R³, —C(O)OR³, or —C(O)NR⁷R⁸.

In another embodiment of Formula IIa, R² is —C(O)R⁶, —C(O)OR⁶, —C(O)NR⁷R⁸, —S(O)OR⁷, —S(O)NR⁷R⁸, —S(O)₂OR⁷, or —S(O)₂NR⁷R⁸.

In another embodiment of Formula IIa, R⁴ is H, methyl, ethyl, n-propyl, iso-propyl, n-butyl, cyclopropyl, or cyclopropylmethylenyl, $R^5$ is phenyl, pyridinyl, —C(O)CH$_3$, —C(O)OCH$_3$, —C(O)CH$_2$CH$_3$, or —C(O)OCH$_2$CH$_3$.

In another embodiment of Formula IIa, $R^2$ is alkyl, substituted alkyl, alkenyl, substituted alkenyl, carbocyclyl, substituted carbocyclyl, carbocyclylalkyl, substituted carbocyclylalkyl, aryl, substituted aryl, arylalkyl, substituted arylalkyl, heterocyclylalkyl, or substituted heterocyclylalkyl.

In another embodiment of Formula IIa, $R^2$ is methyl, ethyl, n-propyl, isopropyl, n-butyl, allyl, cyclopropyl, methylcyclopropyl, cyclopropylmethylene, benzyl, or methoxybezyl.

In another embodiment of Formula IIa, $L^3$ is —O—.

In another embodiment of Formula IIa, -$L^3$-$R^3$ is —O-alkyl or —O-alkylene-O-alkyl.

In another embodiment of Formula IIa, -$L^3$-$R^3$ is —OCH$_2$CH$_2$OCH$_3$ or —OCH$_2$CH$_2$CH$_2$CH$_3$.

In another embodiment of Formula IIa, $R^1$ is —NR$^4$R$^5$; $R^2$ is alkyl, substituted alkyl, alkenyl, substituted alkenyl, cyclylalkyl, substituted cyclylalkyl, cyclylalkylalkyl, substituted cyclylalkylalkyl, aryl, substituted aryl, arylalkyl, substituted arylalkyl, heterocyclylalkyl, or substituted heterocyclylalkyl; $L^3$ is —O—; $R^3$ is alkyl, substituted alkyl, heteroalkyl, substituted heteroalkyl; and $R^4$ and $R^5$, taken together with the nitrogen to which they are both attached, form a substituted or unsubstituted heterocycle.

In one embodiment of Formula I, $L^2$ is a covalent bond, and $R^2$ is hydrogen or halogen. That is, Formula I is represented by Formula Ib:

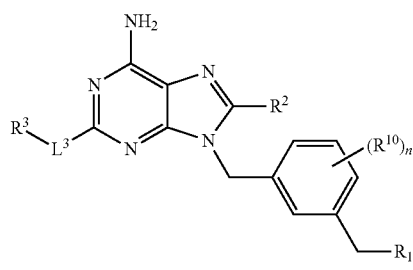

wherein:
$R^1$ is —NR$^4$R$^5$;
$R^2$ is H or halo;
$L^3$ is —NH—, —O—, —S—, —N(R$^9$)C(O)—, —S(O)$_2$—, —S(O)—, or a covalent bond;
$R^3$ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;
$R^4$ and $R^5$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, —C(O)H, —C(O)R$^3$, —S(O)R$^3$, —S(O)$_2$R$^3$, —C(O)OR$^3$, or —C(O)NR$^7$R$^8$; or
$R^4$ and $R^5$, taken together with the nitrogen to which they are both attached, form a substituted or unsubstituted heterocycle;
$R^6$ is alkyl, substituted alkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl;
$R^7$ and $R^8$ are each independently H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl; or
$R^7$ and $R^8$, taken together with the nitrogen to which they are both bonded, form a substituted or unsubstituted heterocycle;
$R^9$ is H, alkyl, substituted alkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, a protecting group, or a prodrug moiety,
$R^{10}$ is halogen, cyano, azido, nitro, alkyl, substituted alkyl, hydroxyl, amino, heteroalkyl, or substituted heteroalkyl; and n is an integer from 0 to 4; and In one embodiment of Formula Ib, $R^1$ is NR$^4$R$^5$; and $R^4$ and $R^5$, taken together with the nitrogen to which they are both attached, form a substituted or unsubstituted heterocycle; wherein the heterocycle is a 4- to 6-membered monocyclic fully saturated or partially unsaturated ring containing at least one hetero atom selected from N, O, and S. In this embodiment, the heterocycle can be selected from the group consisting of:

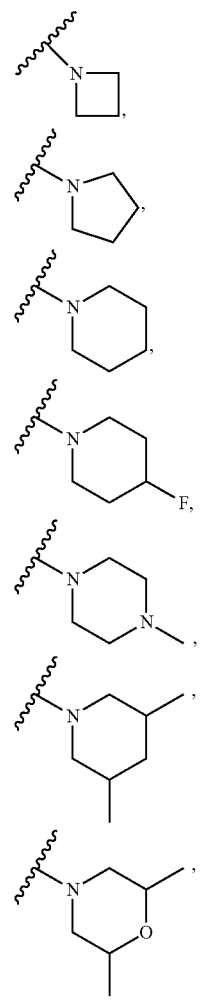

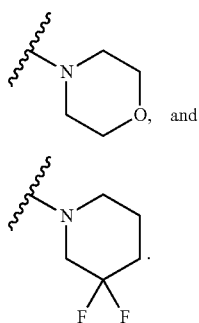

In one embodiment of Formula Ib, -L³-R³ is —O-alkyl or —O-alkylene-O-alkyl. It is preferred that -L³-R³ is —OCH₂CH₂OCH₃ or —OCH₂CH₂CH₂CH₃.

In one embodiment of Formula Ib, R¹ is NR⁴R⁵; -L³-R³ is —O-alkyl or —O-alkylene-O-alkyl; and R⁴ and R⁵, taken together with the nitrogen to which they are both attached, form a substituted or unsubstituted heterocycle; wherein the heterocycle is a 4- to 6-membered monocyclic fully saturated or partially unsaturated ring containing at least one hetero atom selected from N, O, and S.

In another embodiment of formula (I) or (II), the compound is selected from the group consisting of:

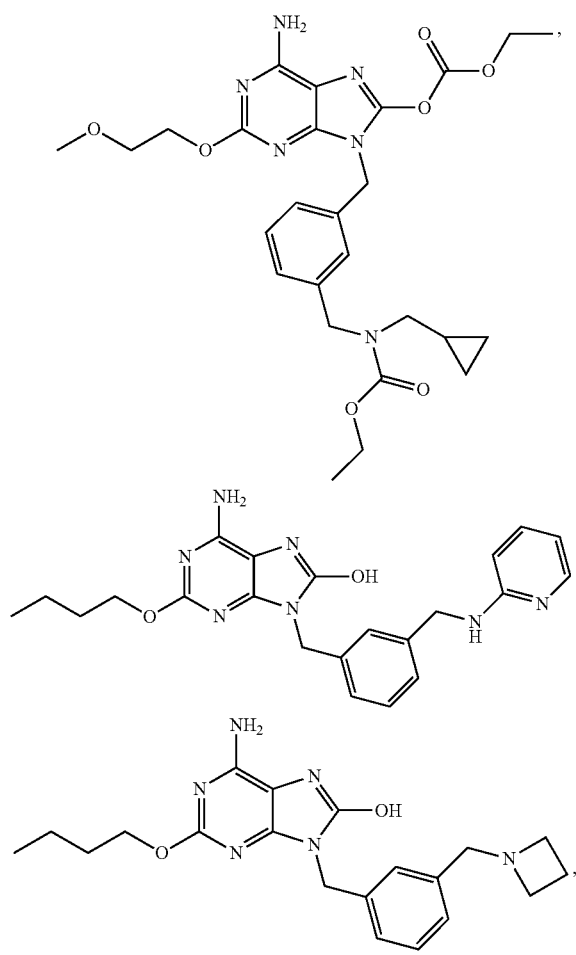

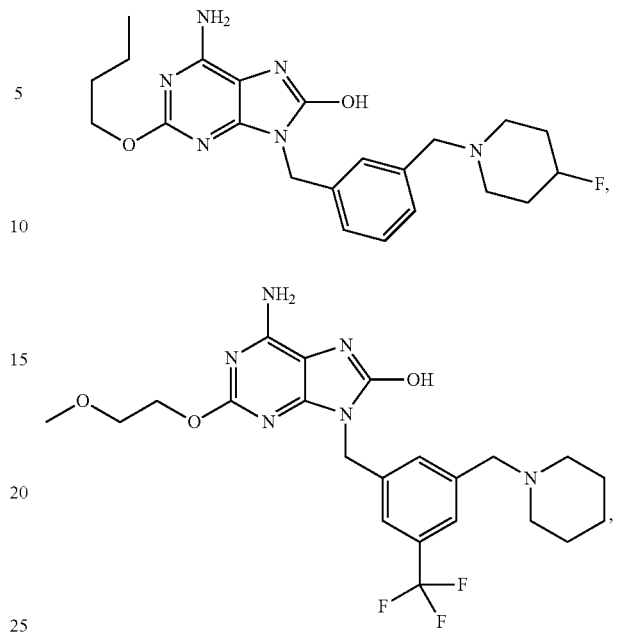

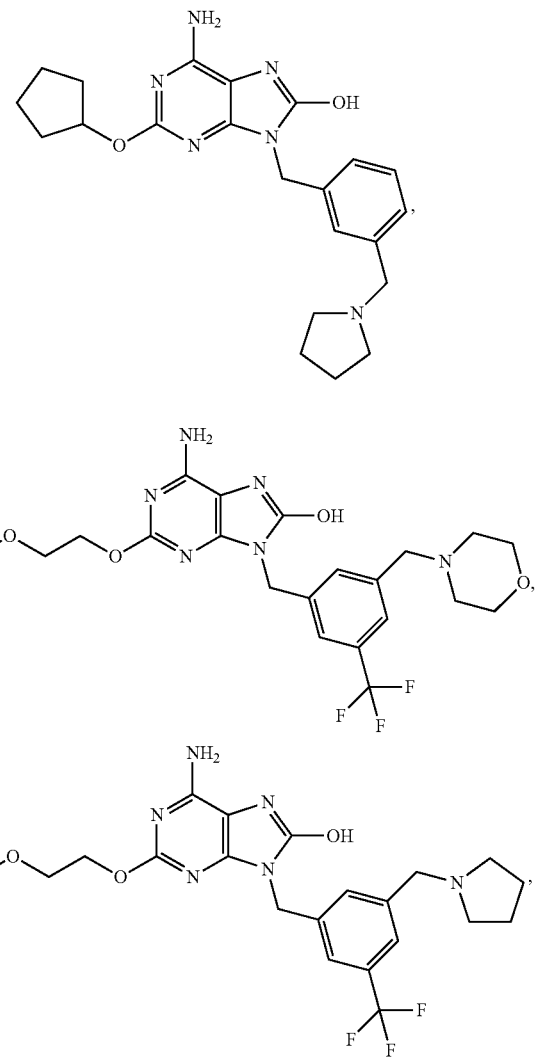

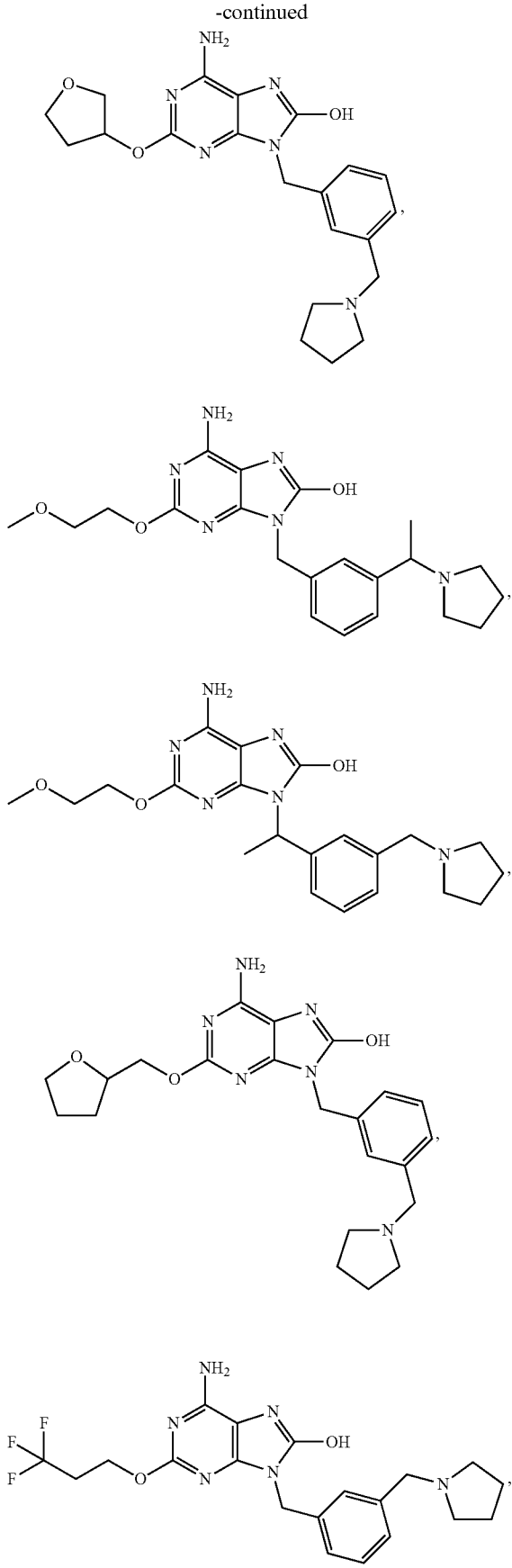

-continued
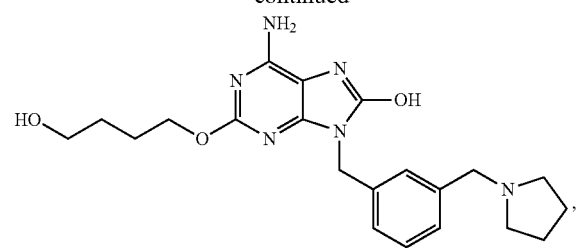
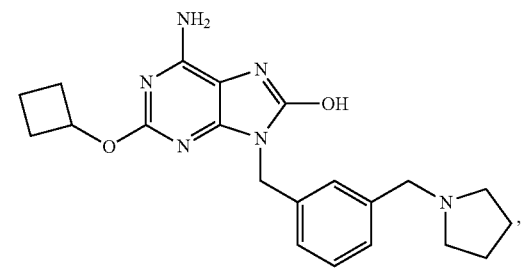
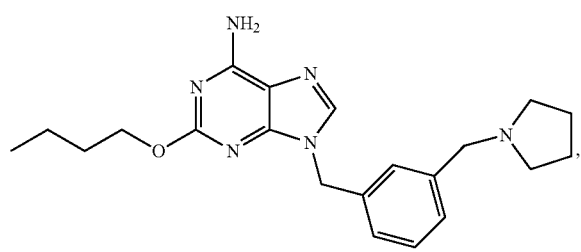
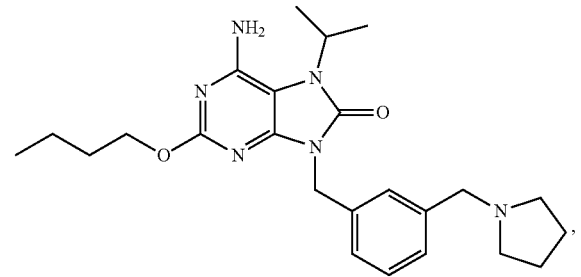
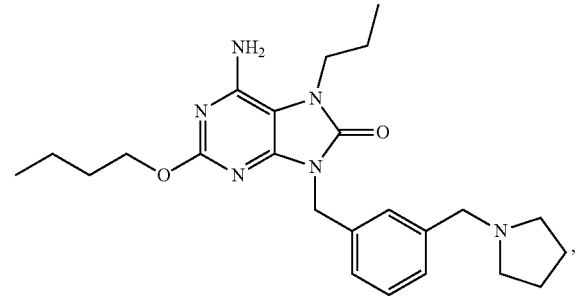
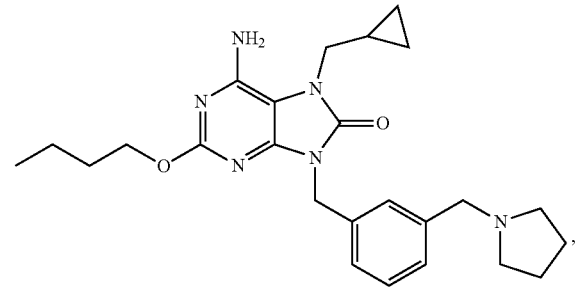
-continued
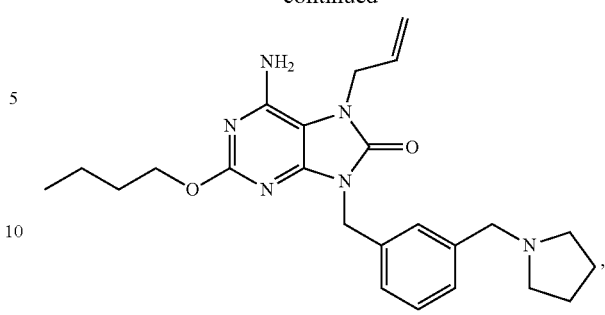
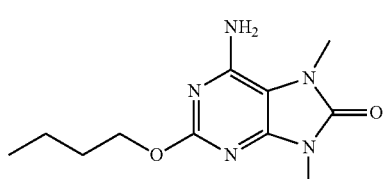
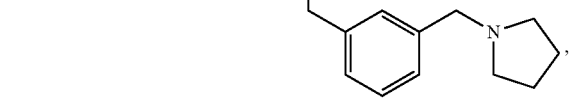
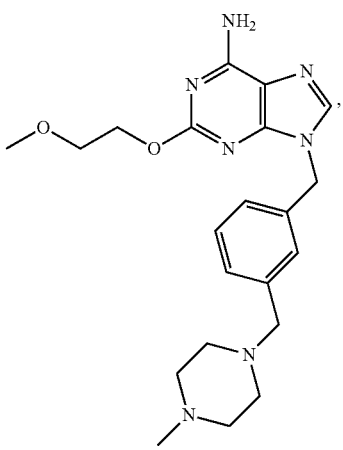
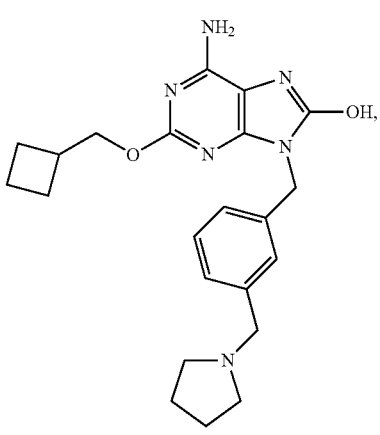

-continued
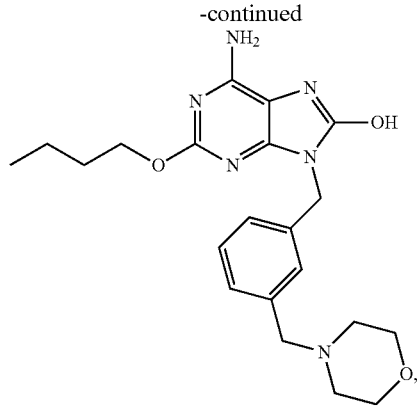
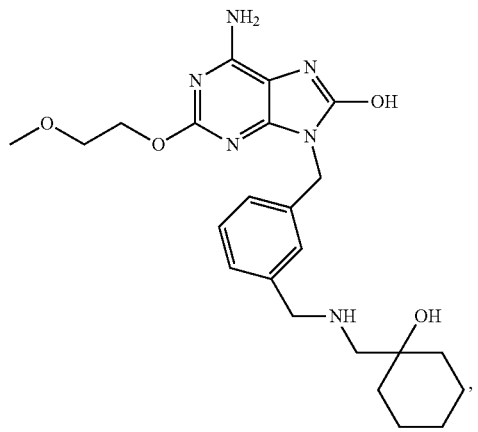
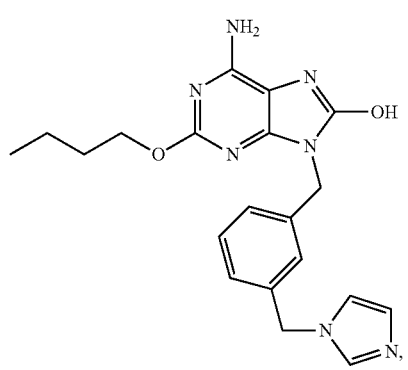
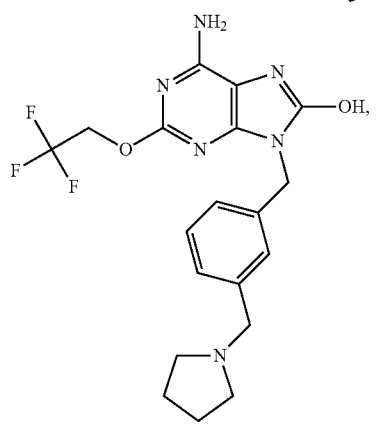
-continued
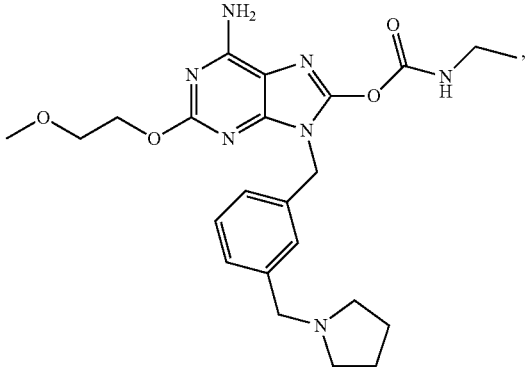
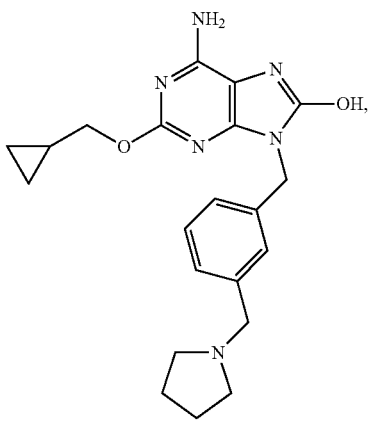
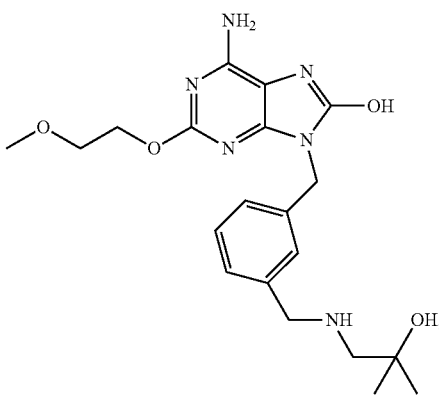
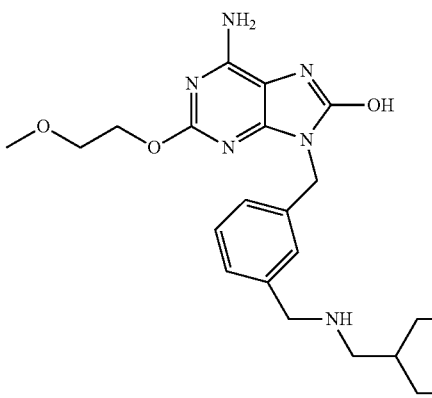

35
-continued
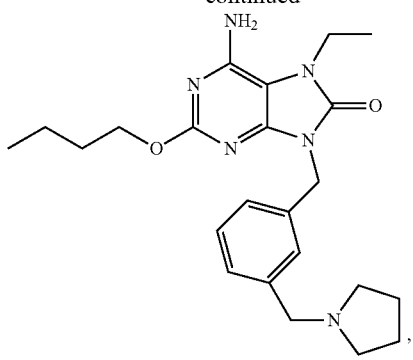
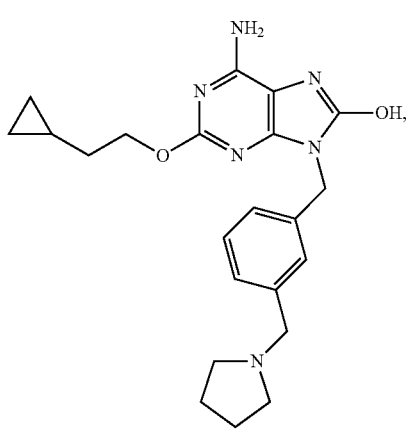
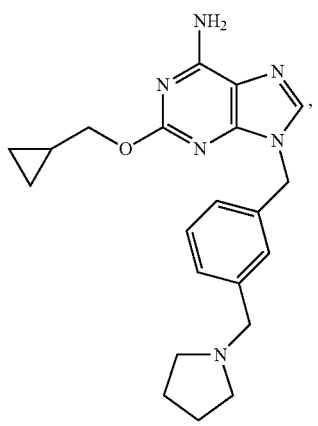
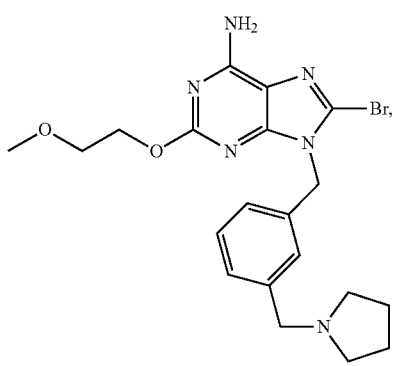
36
-continued
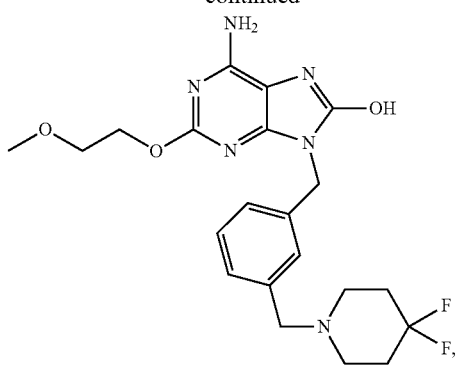
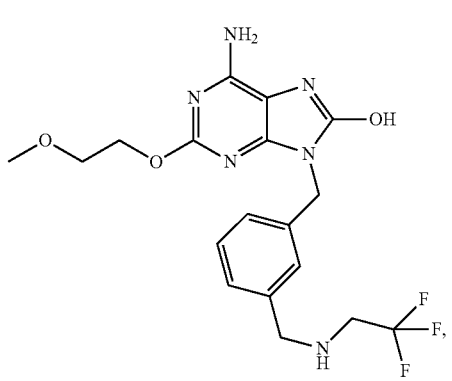
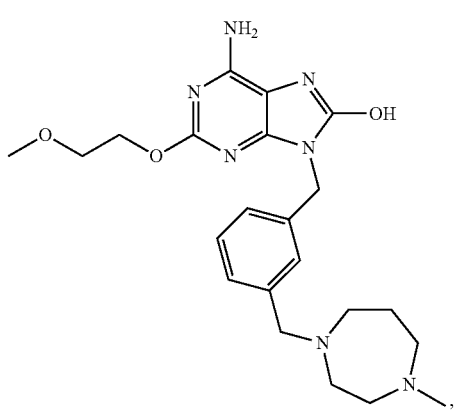
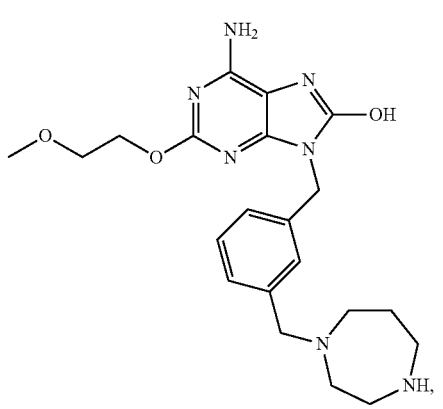

37
-continued
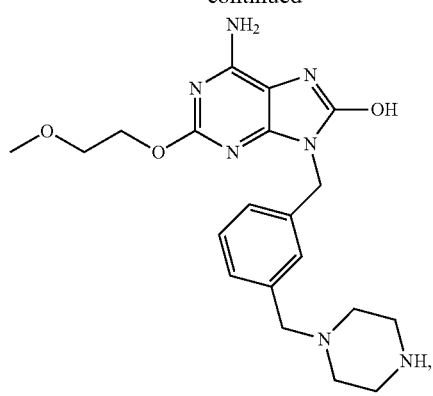
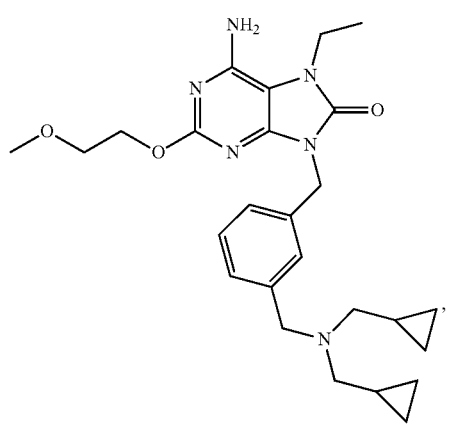
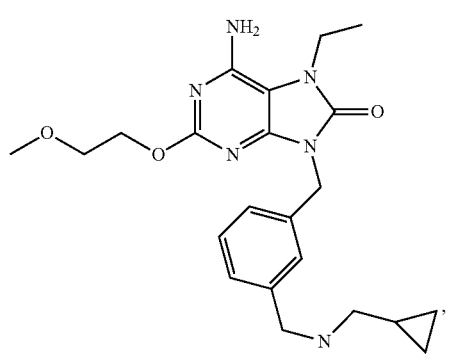
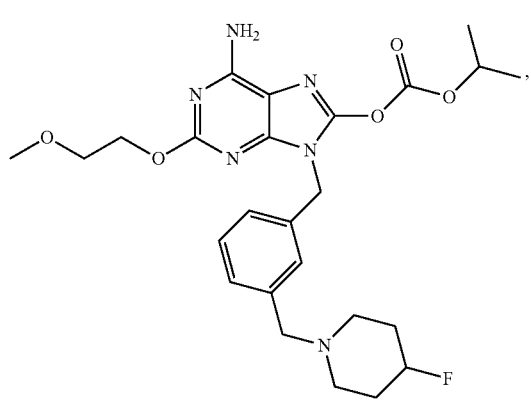
38
-continued
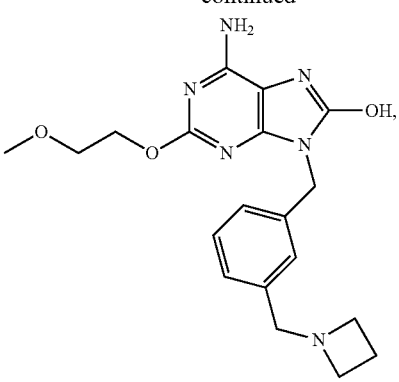
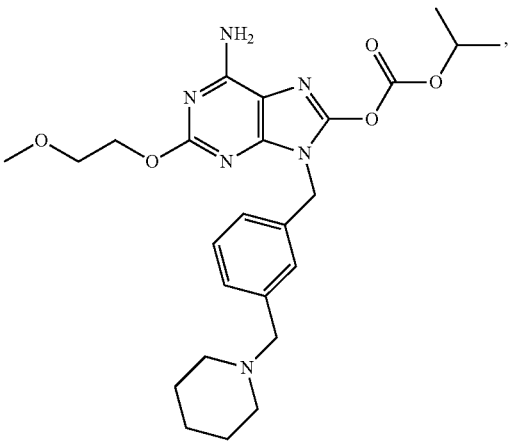
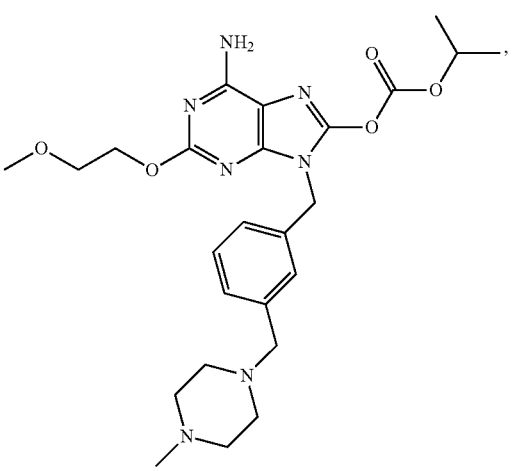
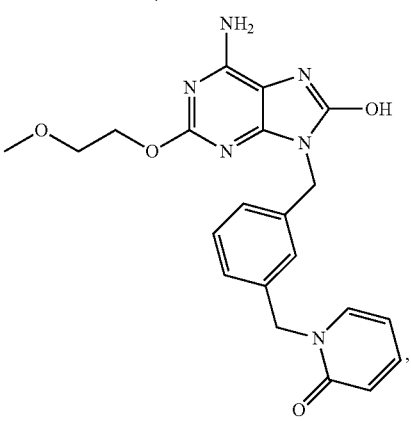

39
-continued
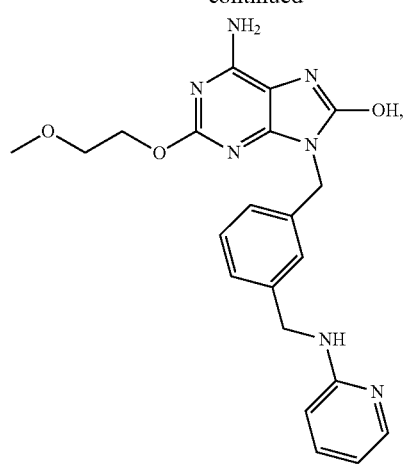
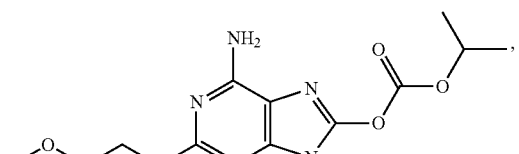
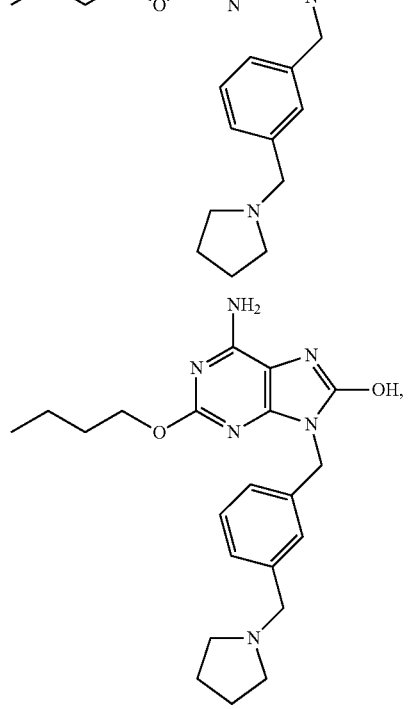
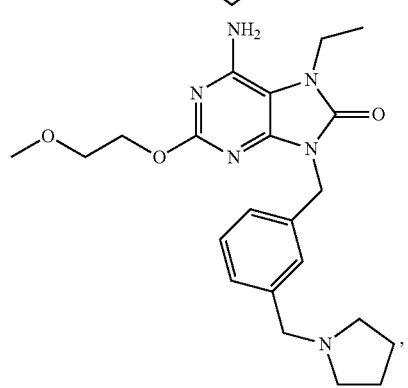
40
-continued
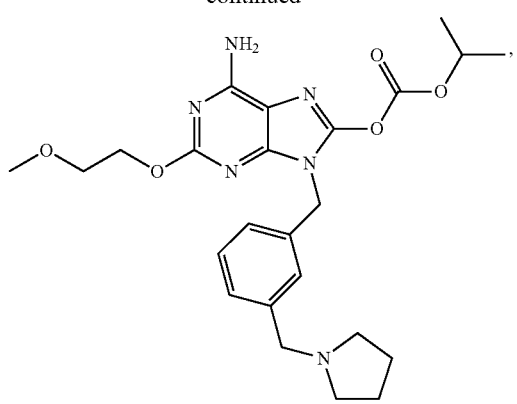
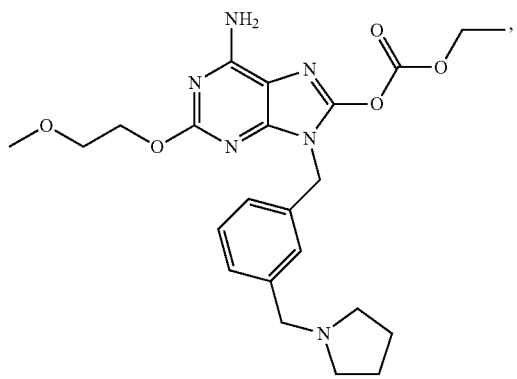
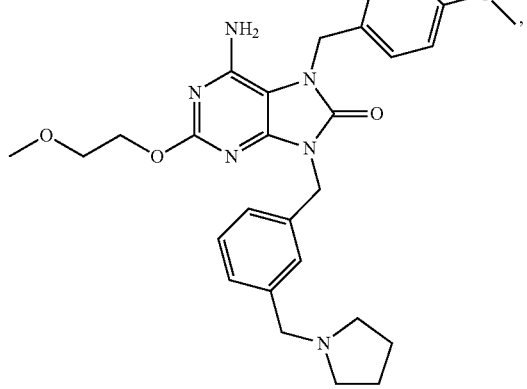
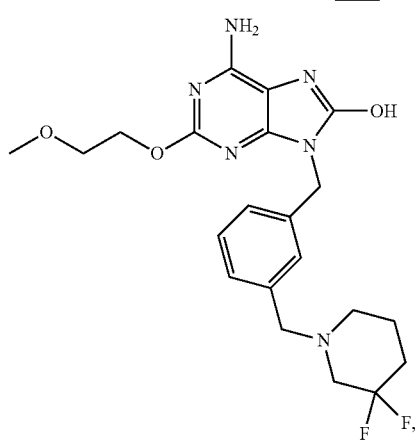

41
-continued
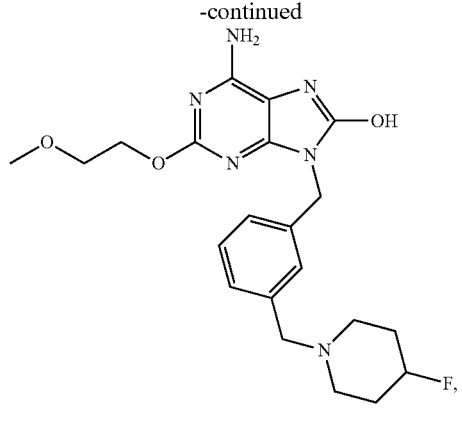
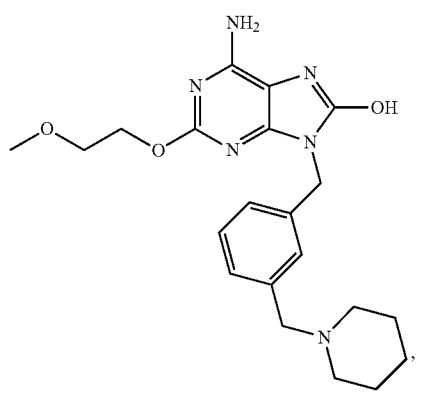
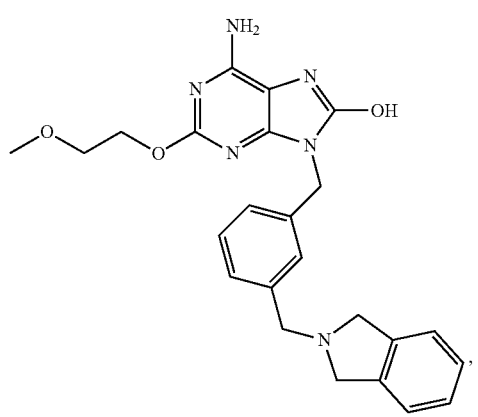
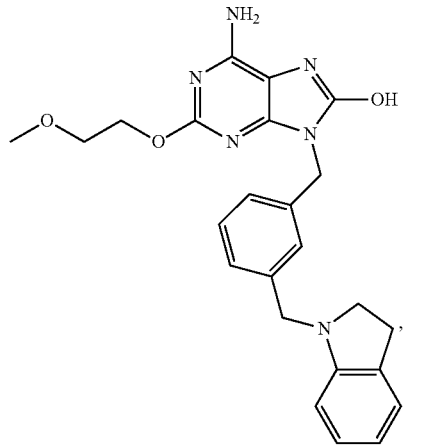
42
-continued
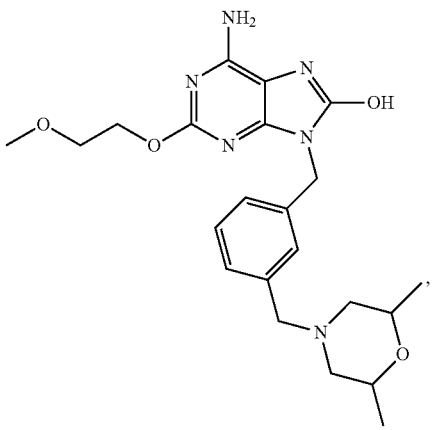
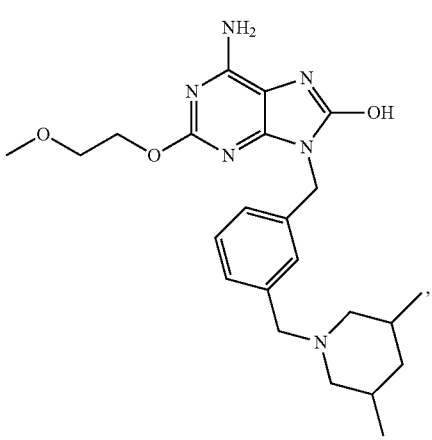
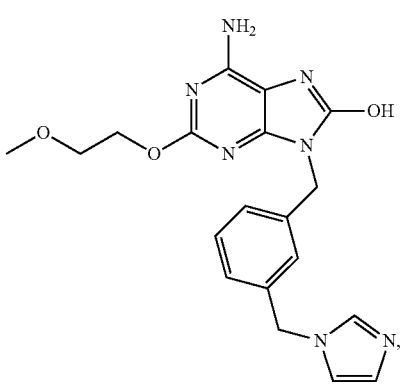
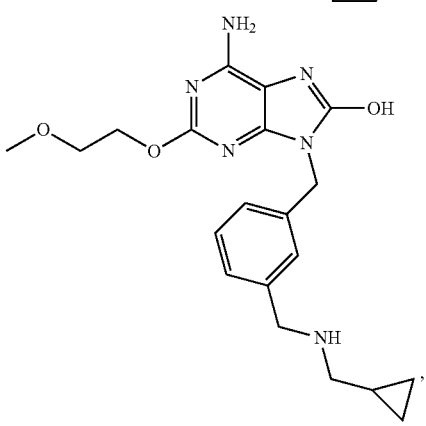

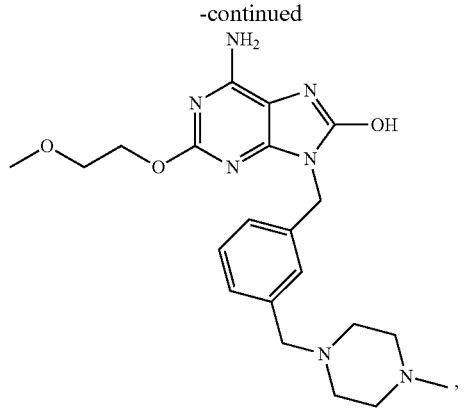
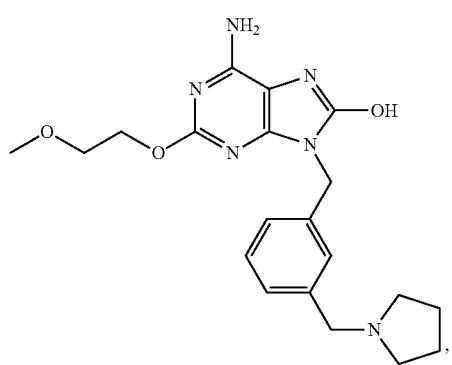
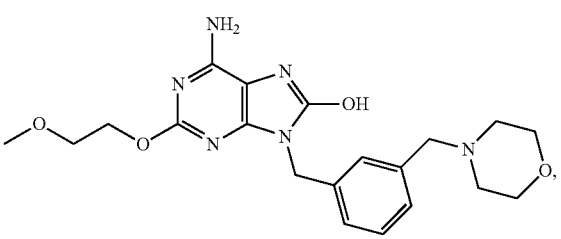
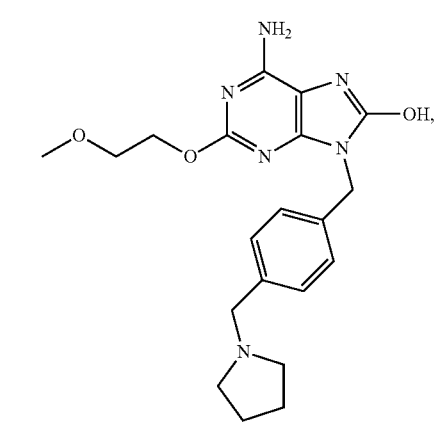
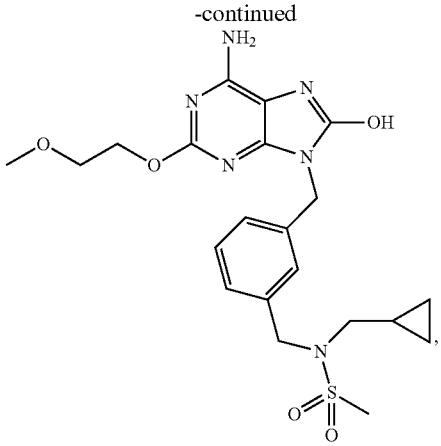
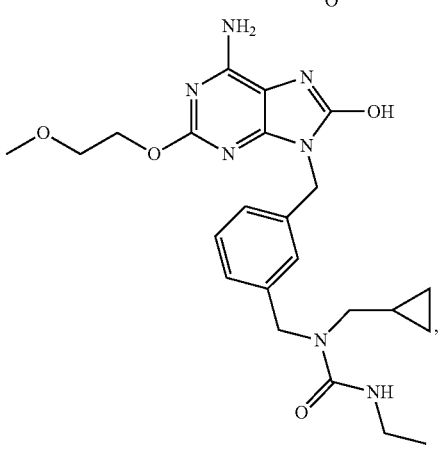
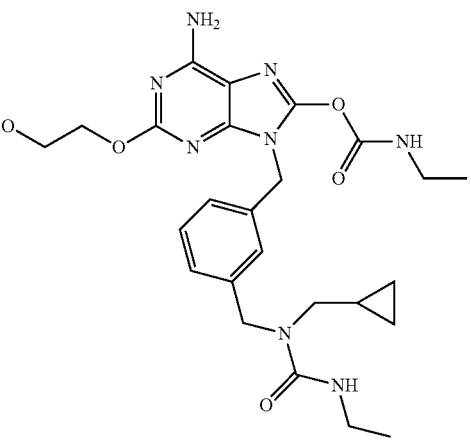, and
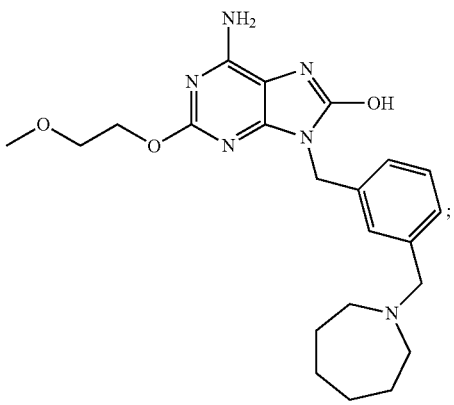;

or pharmaceutically acceptable salts, solvates, and/or esters thereof.

In one embodiment, the present application provides compounds according to Formula Ia:

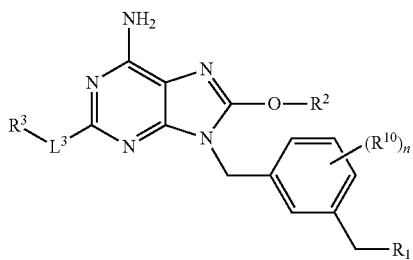

Ia or a pharmaceutically acceptable salt, solvate, and/or ester thereof, wherein:
-$L^3$-$R^3$ is —OCH$_2$CH$_2$OCH$_3$, —OCH$_2$CH$_2$CH$_3$, —OCH$_2$CH$_2$CH$_2$CH$_3$, -Oi-butyl, -Oc-butyl, -Oc-pentyl, —OCH$_2$c-propyl, —OCH$_2$c-butyl, —OCH$_2$CH$_2$c-propyl, —OCH$_2$CH$_2$CH$_2$CH$_2$OH, —OCH$_2$CF$_3$, —OCH$_2$CH$_2$CF$_3$, —OCH$_2$CH$_2$CH$_2$CF$_3$, or (tetrahydrofuran-2-yl)methoxy;

$R^2$ is H;

n is 0;

$R^1$ is —NR$^4$R$^5$; and $R^4$ and $R^5$, taken together with the nitrogen to which they are both attached, form a heterocycle selected from the group consisting of:

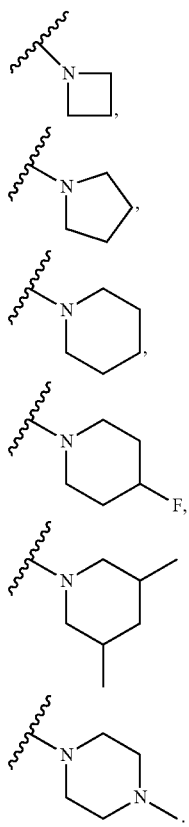

In one embodiment of Formula Ia, -$L^3$-$R^3$ is —OCH$_2$CH$_2$OCH$_3$, —OCH$_2$CH$_2$CH$_2$CH$_3$, —OCH$_2$CH$_2$CF$_3$, —OCH$_2$CH$_2$CH$_2$CH$_2$OH, -Oi-butyl, —OCH$_2$CH$_2$c-propyl, or —OCH$_2$c-propyl.

In one embodiment of Formula Ia, -$L^3$-$R^3$ is —OCH$_2$CH$_2$CH$_2$CH$_3$, —OCH$_2$CH$_2$OCH$_3$, —OCH$_2$CH$_2$CF$_3$, —OCH$_2$CH$_2$CH$_2$CH$_2$OH, or —OCH$_2$c-propyl.

In one embodiment of Formula Ia, -$L^3$-$R^3$ is —OCH$_2$CH$_2$CH$_2$CH$_3$.

In one embodiment of Formula Ia, $R^4$ and $R^5$, taken together with the nitrogen to which they are both attached form a heterocycle selected from the group consisting of:

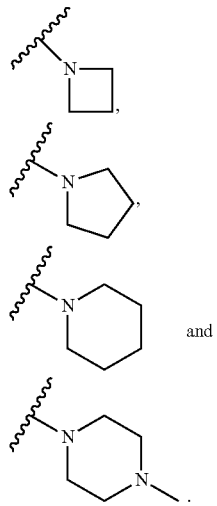

and

In still yet another embodiment, the compounds of Formula I and II are named below in tabular format (Table 5) as compounds of general Formula III:

Formula III

Compounds of general Formula III are depicted as four moieties T1, T2, T3 and T4 attached in the manner shown above. Tables A-D show, respectively, the structures of the T1, T2, T3 and T4 moieties, with the point(s) of attachment to neighboring moieties. Each moiety T1, T2, T3 and T4 in Tables A-D is represented by a "code" comprising letters and numbers. Each structure of a compound of Formula III can be designated in tabular form by combining the "code" representing each structural moiety using the following syntax: T1.T2.T3.T4. Thus, for example, T1A.T2A.T3A.T4A represents the following structure:

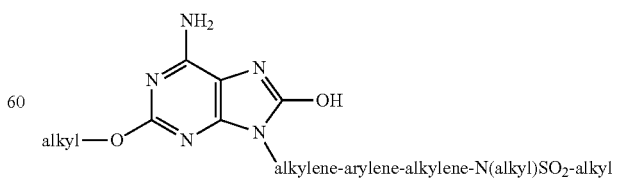

wherein the terms "alkylene", "arylene", "alkyl", "cycloalkylalkyl", "heteroarylene", "carboxcyclylene", "carbocyclyl", "heterocyclyl", etc. are as defined herein.

TABLE 1

T1 Structures

| Label | T1 Structure |
|---|---|
| T1A | —O-alkyl |
| T1B | —O-alkylene-O-alkyl |
| T1C | —S-alkyl |
| T1D | —NH-alkyl (alkyl is substituted or unsubstituted) |
| T1E | alkyl |
| T1F | (cycloalkyl)alkyl-O— |
| T1G | Cycloalkyl-O— |

TABLE 2

T2 Structures

| Label | T2 Structure |
|---|---|
| T2A | [purine structure with NH₂, OH, T1, T3–T4] |
| T2B | [purine structure with NH₂, O-C(O)-O-alkyl, T1, T3–T4] |
| T2C | [purine structure with NH₂, O-C(O)-NH-alkyl, T1, T3–T4] |
| T2D | [purine structure with NH₂, N-alkyl, =O, T1, T3–T4] |

TABLE 3

T3 Structures

| Label | T3 Structure |
|---|---|
| T3A | -alkylene-arylene-alkylene-T4 (substituted or unsubstituted) |
| T3B | -alkylene-carbocyclylene-alkylene-T4 (substituted or unsubstituted) |
| T3C | -alkylene-heteroarylene-alkylene-T4 (substituted or unsubstituted) |
| T3D | -alkylene-heterocyclene-alkylene-T4 (substituted or unsubstituted) |

TABLE 4

T4 Structures

| Label | T4 Structure |
|---|---|
| T4A | —N(alkyl)S(O)₂-alkyl |
| T4B | —N(cycloalkylalkyl)C(O)O-alkyl |
| T4C | —N(cycloalkylalkyl)C(O)N(alkyl)₂ |
| T4D | —N(cycloalkylalkyl)₂ |
| T4E | —NH(cycloalkylalkyl) |
| T4F | —NH(carbocyclyl) |
| T4G | —NH(heterocyclyl) |
| T4H | Nitrogen containing heterocycle attached at nitrogen |

TABLE 5

List of Compound Structures of Formula III

T1A.T2A.T3A.T4A, T1A.T2A.T3A.T4B, T1A.T2A.T3A.T4C, T1A.T2A.T3A.T4D,
T1A.T2A.T3A.T4E, T1A.T2A.T3A.T4F, T1A.T2A.T3A.T4G, T1A.T2A.T3A.T4H,
T1A.T2A.T3B.T4A, T1A.T2A.T3B.T4B, T1A.T2A.T3B.T4C, T1A.T2A.T3B.T4D,
T1A.T2A.T3B.T4E, T1A.T2A.T3B.T4F, T1A.T2A.T3B.T4G, T1A.T2A.T3B.T4H,
T1A.T2A.T3C.T4A, T1A.T2A.T3C.T4B, T1A.T2A.T3C.T4C, T1A.T2A.T3C.T4D,
T1A.T2A.T3C.T4E, T1A.T2A.T3C.T4F, T1A.T2A.T3C.T4G, T1A.T2A.T3C.T4H,
T1A.T2A.T3D.T4A, T1A.T2A.T3D.T4B, T1A.T2A.T3D.T4C, T1A.T2A.T3D.T4D,
T1A.T2A.T3D.T4E, T1A.T2A.T3D.T4F, T1A.T2A.T3D.T4G, T1A.T2A.T3D.T4H,
T1A.T2B.T3A.T4A, T1A.T2B.T3A.T4B, T1A.T2B.T3A.T4C, T1A.T2B.T3A.T4D,
T1A.T2B.T3A.T4E, T1A.T2B.T3A.T4F, T1A.T2B.T3A.T4G, T1A.T2B.T3A.T4H,
T1A.T2B.T3B.T4A, T1A.T2B.T3B.T4B, T1A.T2B.T3B.T4C, T1A.T2B.T3B.T4D,
T1A.T2B.T3B.T4E, T1A.T2B.T3B.T4F, T1A.T2B.T3B.T4G, T1A.T2B.T3B.T4H,
T1A.T2B.T3C.T4A, T1A.T2B.T3C.T4B, T1A.T2B.T3C.T4C, T1A.T2B.T3C.T4D,
T1A.T2B.T3C.T4E, T1A.T2B.T3C.T4F, T1A.T2B.T3C.T4G, T1A.T2B.T3C.T4H,
T1A.T2B.T3D.T4A, T1A.T2B.T3D.T4B, T1A.T2B.T3D.T4C, T1A.T2B.T3D.T4D,
T1A.T2B.T3D.T4E, T1A.T2B.T3D.T4F, T1A.T2B.T3D.T4G, T1A.T2B.T3D.T4H,
T1A.T2C.T3A.T4A, T1A.T2C.T3A.T4B, T1A.T2C.T3A.T4C, T1A.T2C.T3A.T4D,
T1A.T2C.T3A.T4E, T1A.T2C.T3A.T4F, T1A.T2C.T3A.T4G, T1A.T2C.T3A.T4H,
T1A.T2C.T3B.T4A, T1A.T2C.T3B.T4B, T1A.T2C.T3B.T4C, T1A.T2C.T3B.T4D,
T1A.T2C.T3B.T4E, T1A.T2C.T3B.T4F, T1A.T2C.T3B.T4G, T1A.T2C.T3B.T4H,
T1A.T2C.T3C.T4A, T1A.T2C.T3C.T4B, T1A.T2C.T3C.T4C, T1A.T2C.T3C.T4D,

TABLE 5-continued

List of Compound Structures of Formula III

T1A.T2C.T3C.T4E, T1A.T2C.T3C.T4F, T1A.T2C.T3C.T4G, T1A.T2C.T3C.T4H,
T1A.T2C.T3D.T4A, T1A.T2C.T3D.T4B, T1A.T2C.T3D.T4C, T1A.T2C.T3D.T4D,
T1A.T2C.T3D.T4E, T1A.T2C.T3D.T4F, T1A.T2C.T3D.T4G, T1A.T2C.T3D.T4H,
T1A.T2D.T3A.T4A, T1A.T2D.T3A.T4B, T1A.T2D.T3A.T4C, T1A.T2D.T3A.T4D,
T1A.T2D.T3A.T4E, T1A.T2D.T3A.T4F, T1A.T2D.T3A.T4G, T1A.T2D.T3A.T4H,
T1A.T2D.T3B.T4A, T1A.T2D.T3B.T4B, T1A.T2D.T3B.T4C, T1A.T2D.T3B.T4D,
T1A.T2D.T3B.T4E, T1A.T2D.T3B.T4F, T1A.T2D.T3B.T4G, T1A.T2D.T3B.T4H,
T1A.T2D.T3C.T4A, T1A.T2D.T3C.T4B, T1A.T2D.T3C.T4C, T1A.T2D.T3C.T4D,
T1A.T2D.T3C.T4E, T1A.T2D.T3C.T4F, T1A.T2D.T3C.T4G, T1A.T2D.T3C.T4H,
T1A.T2D.T3D.T4A, T1A.T2D.T3D.T4B, T1A.T2D.T3D.T4C, T1A.T2D.T3D.T4D,
T1A.T2D.T3D.T4E, T1A.T2D.T3D.T4F, T1A.T2D.T3D.T4G, T1A.T2D.T3D.T4H,
T1B.T2A.T3A.T4A, T1B.T2A.T3A.T4B, T1B.T2A.T3A.T4C, T1B.T2A.T3A.T4D,
T1B.T2A.T3A.T4E, T1B.T2A.T3A.T4F, T1B.T2A.T3A.T4G, T1B.T2A.T3A.T4H,
T1B.T2A.T3B.T4A, T1B.T2A.T3B.T4B, T1B.T2A.T3B.T4C, T1B.T2A.T3B.T4D,
T1B.T2A.T3B.T4E, T1B.T2A.T3B.T4F, T1B.T2A.T3B.T4G, T1B.T2A.T3B.T4H,
T1B.T2A.T3C.T4A, T1B.T2A.T3C.T4B, T1B.T2A.T3C.T4C, T1B.T2A.T3C.T4D,
T1B.T2A.T3C.T4E, T1B.T2A.T3C.T4F, T1B.T2A.T3C.T4G, T1B.T2A.T3C.T4H,
T1B.T2A.T3D.T4A, T1B.T2A.T3D.T4B, T1B.T2A.T3D.T4C, T1B.T2A.T3D.T4D,
T1B.T2A.T3D.T4E, T1B.T2A.T3D.T4F, T1B.T2A.T3D.T4G, T1B.T2A.T3D.T4H,
T1B.T2B.T3A.T4A, T1B.T2B.T3A.T4B, T1B.T2B.T3A.T4C, T1B.T2B.T3A.T4D,
T1B.T2B.T3A.T4E, T1B.T2B.T3A.T4F, T1B.T2B.T3A.T4G, T1B.T2B.T3A.T4H,
T1B.T2B.T3B.T4A, T1B.T2B.T3B.T4B, T1B.T2B.T3B.T4C, T1B.T2B.T3B.T4D,
T1B.T2B.T3B.T4E, T1B.T2B.T3B.T4F, T1B.T2B.T3B.T4G, T1B.T2B.T3B.T4H,
T1B.T2B.T3C.T4A, T1B.T2B.T3C.T4B, T1B.T2B.T3C.T4C, T1B.T2B.T3C.T4D,
T1B.T2B.T3C.T4E, T1B.T2B.T3C.T4F, T1B.T2B.T3C.T4G, T1B.T2B.T3C.T4H,
T1B.T2B.T3D.T4A, T1B.T2B.T3D.T4B, T1B.T2B.T3D.T4C, T1B.T2B.T3D.T4D,
T1B.T2B.T3D.T4E, T1B.T2B.T3D.T4F, T1B.T2B.T3D.T4G, T1B.T2B.T3D.T4H,
T1B.T2C.T3A.T4A, T1B.T2C.T3A.T4B, T1B.T2C.T3A.T4C, T1B.T2C.T3A.T4D,
T1B.T2C.T3A.T4E, T1B.T2C.T3A.T4F, T1B.T2C.T3A.T4G, T1B.T2C.T3A.T4H,
T1B.T2C.T3B.T4A, T1B.T2C.T3B.T4B, T1B.T2C.T3B.T4C, T1B.T2C.T3B.T4D,
T1B.T2C.T3B.T4E, T1B.T2C.T3B.T4F, T1B.T2C.T3B.T4G, T1B.T2C.T3B.T4H,
T1B.T2C.T3C.T4A, T1B.T2C.T3C.T4B, T1B.T2C.T3C.T4C, T1B.T2C.T3C.T4D,
T1B.T2C.T3C.T4E, T1B.T2C.T3C.T4F, T1B.T2C.T3C.T4G, T1B.T2C.T3C.T4H,
T1B.T2C.T3D.T4A, T1B.T2C.T3D.T4B, T1B.T2C.T3D.T4C, T1B.T2C.T3D.T4D,
T1B.T2C.T3D.T4E, T1B.T2C.T3D.T4F, T1B.T2C.T3D.T4G, T1B.T2C.T3D.T4H,
T1B.T2D.T3A.T4A, T1B.T2D.T3A.T4B, T1B.T2D.T3A.T4C, T1B.T2D.T3A.T4D,
T1B.T2D.T3A.T4E, T1B.T2D.T3A.T4F, T1B.T2D.T3A.T4G, T1B.T2D.T3A.T4H,
T1B.T2D.T3B.T4A, T1B.T2D.T3B.T4B, T1B.T2D.T3B.T4C, T1B.T2D.T3B.T4D,
T1B.T2D.T3B.T4E, T1B.T2D.T3B.T4F, T1B.T2D.T3B.T4G, T1B.T2D.T3B.T4H,
T1B.T2D.T3C.T4A, T1B.T2D.T3C.T4B, T1B.T2D.T3C.T4C, T1B.T2D.T3C.T4D,
T1B.T2D.T3C.T4E, T1B.T2D.T3C.T4F, T1B.T2D.T3C.T4G, T1B.T2D.T3C.T4H,
T1B.T2D.T3D.T4A, T1B.T2D.T3D.T4B, T1B.T2D.T3D.T4C, T1B.T2D.T3D.T4D,
T1B.T2D.T3D.T4E, T1B.T2D.T3D.T4F, T1B.T2D.T3D.T4G, T1B.T2D.T3D.T4H,
T1C.T2A.T3A.T4A, T1C.T2A.T3A.T4B, T1C.T2A.T3A.T4C, T1C.T2A.T3A.T4D,
T1C.T2A.T3A.T4E, T1C.T2A.T3A.T4F, T1C.T2A.T3A.T4G, T1C.T2A.T3A.T4H,
T1C.T2A.T3B.T4A, T1C.T2A.T3B.T4B, T1C.T2A.T3B.T4C, T1C.T2A.T3B.T4D,
T1C.T2A.T3B.T4E, T1C.T2A.T3B.T4F, T1C.T2A.T3B.T4G, T1C.T2A.T3B.T4H,
T1C.T2A.T3C.T4A, T1C.T2A.T3C.T4B, T1C.T2A.T3C.T4C, T1C.T2A.T3C.T4D,
T1C.T2A.T3C.T4E, T1C.T2A.T3C.T4F, T1C.T2A.T3C.T4G, T1C.T2A.T3C.T4H,
T1C.T2A.T3D.T4A, T1C.T2A.T3D.T4B, T1C.T2A.T3D.T4C, T1C.T2A.T3D.T4D,
T1C.T2A.T3D.T4E, T1C.T2A.T3D.T4F, T1C.T2A.T3D.T4G, T1C.T2A.T3D.T4H,
T1C.T2B.T3A.T4A, T1C.T2B.T3A.T4B, T1C.T2B.T3A.T4C, T1C.T2B.T3A.T4D,
T1C.T2B.T3A.T4E, T1C.T2B.T3A.T4F, T1C.T2B.T3A.T4G, T1C.T2B.T3A.T4H,
T1C.T2B.T3B.T4A, T1C.T2B.T3B.T4B, T1C.T2B.T3B.T4C, T1C.T2B.T3B.T4D,
T1C.T2B.T3B.T4E, T1C.T2B.T3B.T4F, T1C.T2B.T3B.T4G, T1C.T2B.T3B.T4H,
T1C.T2B.T3C.T4A, T1C.T2B.T3C.T4B, T1C.T2B.T3C.T4C, T1C.T2B.T3C.T4D,
T1C.T2B.T3C.T4E, T1C.T2B.T3C.T4F, T1C.T2B.T3C.T4G, T1C.T2B.T3C.T4H,
T1C.T2B.T3D.T4A, T1C.T2B.T3D.T4B, T1C.T2B.T3D.T4C, T1C.T2B.T3D.T4D,
T1C.T2B.T3D.T4E, T1C.T2B.T3D.T4F, T1C.T2B.T3D.T4G, T1C.T2B.T3D.T4H,
T1C.T2C.T3A.T4A, T1C.T2C.T3A.T4B, T1C.T2C.T3A.T4C, T1C.T2C.T3A.T4D,
T1C.T2C.T3A.T4E, T1C.T2C.T3A.T4F, T1C.T2C.T3A.T4G, T1C.T2C.T3A.T4H,
T1C.T2C.T3B.T4A, T1C.T2C.T3B.T4B, T1C.T2C.T3B.T4C, T1C.T2C.T3B.T4D,
T1C.T2C.T3B.T4E, T1C.T2C.T3B.T4F, T1C.T2C.T3B.T4G, T1C.T2C.T3B.T4H,
T1C.T2C.T3C.T4A, T1C.T2C.T3C.T4B, T1C.T2C.T3C.T4C, T1C.T2C.T3C.T4D,
T1C.T2C.T3C.T4E, T1C.T2C.T3C.T4F, T1C.T2C.T3C.T4G, T1C.T2C.T3C.T4H,
T1C.T2C.T3D.T4A, T1C.T2C.T3D.T4B, T1C.T2C.T3D.T4C, T1C.T2C.T3D.T4D,
T1C.T2C.T3D.T4E, T1C.T2C.T3D.T4F, T1C.T2C.T3D.T4G, T1C.T2C.T3D.T4H,
T1C.T2D.T3A.T4A, T1C.T2D.T3A.T4B, T1C.T2D.T3A.T4C, T1C.T2D.T3A.T4D,
T1C.T2D.T3A.T4E, T1C.T2D.T3A.T4F, T1C.T2D.T3A.T4G, T1C.T2D.T3A.T4H,

TABLE 5-continued

List of Compound Structures of Formula III

T1C.T2D.T3B.T4A, T1C.T2D.T3B.T4B, T1C.T2D.T3B.T4C, T1C.T2D.T3B.T4D,
T1C.T2D.T3B.T4E, T1C.T2D.T3B.T4F, T1C.T2D.T3B.T4G, T1C.T2D.T3B.T4H,
T1C.T2D.T3C.T4A, T1C.T2D.T3C.T4B, T1C.T2D.T3C.T4C, T1C.T2D.T3C.T4D,
T1C.T2D.T3C.T4E, T1C.T2D.T3C.T4F, T1C.T2D.T3C.T4G, T1C.T2D.T3C.T4H,
T1C.T2D.T3D.T4A, T1C.T2D.T3D.T4B, T1C.T2D.T3D.T4C, T1C.T2D.T3D.T4D,
T1C.T2D.T3D.T4E, T1C.T2D.T3D.T4F, T1C.T2D.T3D.T4G, T1C.T2D.T3D.T4H,
T1D.T2A.T3A.T4A, T1D.T2A.T3A.T4B, T1D.T2A.T3A.T4C, T1D.T2A.T3A.T4D,
T1D.T2A.T3A.T4E, T1D.T2A.T3A.T4F, T1D.T2A.T3A.T4G, T1D.T2A.T3A.T4H,
T1D.T2A.T3B.T4A, T1D.T2A.T3B.T4B, T1D.T2A.T3B.T4C, T1D.T2A.T3B.T4D,
T1D.T2A.T3B.T4E, T1D.T2A.T3B.T4F, T1D.T2A.T3B.T4G, T1D.T2A.T3B.T4H,
T1D.T2A.T3C.T4A, T1D.T2A.T3C.T4B, T1D.T2A.T3C.T4C, T1D.T2A.T3C.T4D,
T1D.T2A.T3C.T4E, T1D.T2A.T3C.T4F, T1D.T2A.T3C.T4G, T1D.T2A.T3C.T4H,
T1D.T2A.T3D.T4A, T1D.T2A.T3D.T4B, T1D.T2A.T3D.T4C, T1D.T2A.T3D.T4D,
T1D.T2A.T3D.T4E, T1D.T2A.T3D.T4F, T1D.T2A.T3D.T4G, T1D.T2A.T3D.T4H,
T1D.T2B.T3A.T4A, T1D.T2B.T3A.T4B, T1D.T2B.T3A.T4C, T1D.T2B.T3A.T4D,
T1D.T2B.T3A.T4E, T1D.T2B.T3A.T4F, T1D.T2B.T3A.T4G, T1D.T2B.T3A.T4H,
T1D.T2B.T3B.T4A, T1D.T2B.T3B.T4B, T1D.T2B.T3B.T4C, T1D.T2B.T3B.T4D,
T1D.T2B.T3B.T4E, T1D.T2B.T3B.T4F, T1D.T2B.T3B.T4G, T1D.T2B.T3B.T4H,
T1D.T2B.T3C.T4A, T1D.T2B.T3C.T4B, T1D.T2B.T3C.T4C, T1D.T2B.T3C.T4D,
T1D.T2B.T3C.T4E, T1D.T2B.T3C.T4F, T1D.T2B.T3C.T4G, T1D.T2B.T3C.T4H,
T1D.T2B.T3D.T4A, T1D.T2B.T3D.T4B, T1D.T2B.T3D.T4C, T1D.T2B.T3D.T4D,
T1D.T2B.T3D.T4E, T1D.T2B.T3D.T4F, T1D.T2B.T3D.T4G, T1D.T2B.T3D.T4H,
T1D.T2C.T3A.T4A, T1D.T2C.T3A.T4B, T1D.T2C.T3A.T4C, T1D.T2C.T3A.T4D,
T1D.T2C.T3A.T4E, T1D.T2C.T3A.T4F, T1D.T2C.T3A.T4G, T1D.T2C.T3A.T4H,
T1D.T2C.T3B.T4A, T1D.T2C.T3B.T4B, T1D.T2C.T3B.T4C, T1D.T2C.T3B.T4D,
T1D.T2C.T3B.T4E, T1D.T2C.T3B.T4F, T1D.T2C.T3B.T4G, T1D.T2C.T3B.T4H,
T1D.T2C.T3C.T4A, T1D.T2C.T3C.T4B, T1D.T2C.T3C.T4C, T1D.T2C.T3C.T4D,
T1D.T2C.T3C.T4E, T1D.T2C.T3C.T4F, T1D.T2C.T3C.T4G, T1D.T2C.T3C.T4H,
T1D.T2C.T3D.T4A, T1D.T2C.T3D.T4B, T1D.T2C.T3D.T4C, T1D.T2C.T3D.T4D,
T1D.T2C.T3D.T4E, T1D.T2C.T3D.T4F, T1D.T2C.T3D.T4G, T1D.T2C.T3D.T4H,
T1D.T2D.T3A.T4A, T1D.T2D.T3A.T4B, T1D.T2D.T3A.T4C, T1D.T2D.T3A.T4D,
T1D.T2D.T3A.T4E, T1D.T2D.T3A.T4F, T1D.T2D.T3A.T4G, T1D.T2D.T3A.T4H,
T1D.T2D.T3B.T4A, T1D.T2D.T3B.T4B, T1D.T2D.T3B.T4C, T1D.T2D.T3B.T4D,
T1D.T2D.T3B.T4E, T1D.T2D.T3B.T4F, T1D.T2D.T3B.T4G, T1D.T2D.T3B.T4H,
T1D.T2D.T3C.T4A, T1D.T2D.T3C.T4B, T1D.T2D.T3C.T4C, T1D.T2D.T3C.T4D,
T1D.T2D.T3C.T4E, T1D.T2D.T3C.T4F, T1D.T2D.T3C.T4G, T1D.T2D.T3C.T4H,
T1D.T2D.T3D.T4A, T1D.T2D.T3D.T4B, T1D.T2D.T3D.T4C, T1D.T2D.T3D.T4D,
T1D.T2D.T3D.T4E, T1D.T2D.T3D.T4F, T1D.T2D.T3D.T4G, T1D.T2D.T3D.T4H,
T1E.T2A.T3A.T4A, T1E.T2A.T3A.T4B, T1E.T2A.T3A.T4C, T1E.T2A.T3A.T4D,
T1E.T2A.T3A.T4E, T1E.T2A.T3A.T4F, T1E.T2A.T3A.T4G, T1E.T2A.T3A.T4H,
T1E.T2A.T3B.T4A, T1E.T2A.T3B.T4B, T1E.T2A.T3B.T4C, T1E.T2A.T3B.T4D,
T1E.T2A.T3B.T4E, T1E.T2A.T3B.T4F, T1E.T2A.T3B.T4G, T1E.T2A.T3B.T4H,
T1E.T2A.T3C.T4A, T1E.T2A.T3C.T4B, T1E.T2A.T3C.T4C, T1E.T2A.T3C.T4D,
T1E.T2A.T3C.T4E, T1E.T2A.T3C.T4F, T1E.T2A.T3C.T4G, T1E.T2A.T3C.T4H,
T1E.T2A.T3D.T4A, T1E.T2A.T3D.T4B, T1E.T2A.T3D.T4C, T1E.T2A.T3D.T4D,
T1E.T2A.T3D.T4E, T1E.T2A.T3D.T4F, T1E.T2A.T3D.T4G, T1E.T2A.T3D.T4H,
T1E.T2B.T3A.T4A, T1E.T2B.T3A.T4B, T1E.T2B.T3A.T4C, T1E.T2B.T3A.T4D,
T1E.T2B.T3A.T4E, T1E.T2B.T3A.T4F, T1E.T2B.T3A.T4G, T1E.T2B.T3A.T4H,
T1E.T2B.T3B.T4A, T1E.T2B.T3B.T4B, T1E.T2B.T3B.T4C, T1E.T2B.T3B.T4D,
T1E.T2B.T3B.T4E, T1E.T2B.T3B.T4F, T1E.T2B.T3B.T4G, T1E.T2B.T3B.T4H,
T1E.T2B.T3C.T4A, T1E.T2B.T3C.T4B, T1E.T2B.T3C.T4C, T1E.T2B.T3C.T4D,
T1E.T2B.T3C.T4E, T1E.T2B.T3C.T4F, T1E.T2B.T3C.T4G, T1E.T2B.T3C.T4H,
T1E.T2B.T3D.T4A, T1E.T2B.T3D.T4B, T1E.T2B.T3D.T4C, T1E.T2B.T3D.T4D,
T1E.T2B.T3D.T4E, T1E.T2B.T3D.T4F, T1E.T2B.T3D.T4G, T1E.T2B.T3D.T4H,
T1E.T2C.T3A.T4A, T1E.T2C.T3A.T4B, T1E.T2C.T3A.T4C, T1E.T2C.T3A.T4D,
T1E.T2C.T3A.T4E, T1E.T2C.T3A.T4F, T1E.T2C.T3A.T4G, T1E.T2C.T3A.T4H,
T1E.T2C.T3B.T4A, T1E.T2C.T3B.T4B, T1E.T2C.T3B.T4C, T1E.T2C.T3B.T4D,
T1E.T2C.T3B.T4E, T1E.T2C.T3B.T4F, T1E.T2C.T3B.T4G, T1E.T2C.T3B.T4H,
T1E.T2C.T3C.T4A, T1E.T2C.T3C.T4B, T1E.T2C.T3C.T4C, T1E.T2C.T3C.T4D,
T1E.T2C.T3C.T4E, T1E.T2C.T3C.T4F, T1E.T2C.T3C.T4G, T1E.T2C.T3C.T4H,
T1E.T2C.T3D.T4A, T1E.T2C.T3D.T4B, T1E.T2C.T3D.T4C, T1E.T2C.T3D.T4D,
T1E.T2C.T3D.T4E, T1E.T2C.T3D.T4F, T1E.T2C.T3D.T4G, T1E.T2C.T3D.T4H,
T1E.T2D.T3A.T4A, T1E.T2D.T3A.T4B, T1E.T2D.T3A.T4C, T1E.T2D.T3A.T4D,
T1E.T2D.T3A.T4E, T1E.T2D.T3A.T4F, T1E.T2D.T3A.T4G, T1E.T2D.T3A.T4H,
T1E.T2D.T3B.T4A, T1E.T2D.T3B.T4B, T1E.T2D.T3B.T4C, T1E.T2D.T3B.T4D,
T1E.T2D.T3B.T4E, T1E.T2D.T3B.T4F, T1E.T2D.T3B.T4G, T1E.T2D.T3B.T4H,
T1E.T2D.T3C.T4A, T1E.T2D.T3C.T4B, T1E.T2D.T3C.T4C, T1E.T2D.T3C.T4D,
T1E.T2D.T3C.T4E, T1E.T2D.T3C.T4F, T1E.T2D.T3C.T4G, T1E.T2D.T3C.T4H,
T1E.T2D.T3D.T4A, T1E.T2D.T3D.T4B, T1E.T2D.T3D.T4C, T1E.T2D.T3D.T4D,
T1E.T2D.T3D.T4E, T1E.T2D.T3D.T4F, T1E.T2D.T3D.T4G, T1E.T2D.T3D.T4H,

TABLE 5-continued

List of Compound Structures of Formula III

T1F.T2A.T3A.T4A, T1F.T2A.T3A.T4B, T1F.T2A.T3A.T4C, T1F.T2A.T3A.T4D,
T1F.T2A.T3A.T4E, T1F.T2A.T3A.T4F, T1F.T2A.T3A.T4G, T1F.T2A.T3A.T4H,
T1F.T2A.T3B.T4A, T1F.T2A.T3B.T4B, T1F.T2A.T3B.T4C, T1F.T2A.T3B.T4D,
T1F.T2A.T3B.T4E, T1F.T2A.T3B.T4F, T1F.T2A.T3B.T4G, T1F.T2A.T3B.T4H,
T1F.T2A.T3C.T4A, T1F.T2A.T3C.T4B, T1F.T2A.T3C.T4C, T1F.T2A.T3C.T4D,
T1F.T2A.T3C.T4E, T1F.T2A.T3C.T4F, T1F.T2A.T3C.T4G, T1F.T2A.T3C.T4H,
T1F.T2A.T3D.T4A, T1F.T2A.T3D.T4B, T1F.T2A.T3D.T4C, T1F.T2A.T3D.T4D,
T1F.T2A.T3D.T4E, T1F.T2A.T3D.T4F, T1F.T2A.T3D.T4G, T1F.T2A.T3D.T4H,
T1F.T2B.T3A.T4A, T1F.T2B.T3A.T4B, T1F.T2B.T3A.T4C, T1F.T2B.T3A.T4D,
T1F.T2B.T3A.T4E, T1F.T2B.T3A.T4F, T1F.T2B.T3A.T4G, T1F.T2B.T3A.T4H,
T1F.T2B.T3B.T4A, T1F.T2B.T3B.T4B, T1F.T2B.T3B.T4C, T1F.T2B.T3B.T4D,
T1F.T2B.T3B.T4E, T1F.T2B.T3B.T4F, T1F.T2B.T3B.T4G, T1F.T2B.T3B.T4H,
T1F.T2B.T3C.T4A, T1F.T2B.T3C.T4B, T1F.T2B.T3C.T4C, T1F.T2B.T3C.T4D,
T1F.T2B.T3C.T4E, T1F.T2B.T3C.T4F, T1F.T2B.T3C.T4G, T1F.T2B.T3C.T4H,
T1F.T2B.T3D.T4A, T1F.T2B.T3D.T4B, T1F.T2B.T3D.T4C, T1F.T2B.T3D.T4D,
T1F.T2B.T3D.T4E, T1F.T2B.T3D.T4F, T1F.T2B.T3D.T4G, T1F.T2B.T3D.T4H,
T1F.T2C.T3A.T4A, T1F.T2C.T3A.T4B, T1F.T2C.T3A.T4C, T1F.T2C.T3A.T4D,
T1F.T2C.T3A.T4E, T1F.T2C.T3A.T4F, T1F.T2C.T3A.T4G, T1F.T2C.T3A.T4H,
T1F.T2C.T3B.T4A, T1F.T2C.T3B.T4B, T1F.T2C.T3B.T4C, T1F.T2C.T3B.T4D,
T1F.T2C.T3B.T4E, T1F.T2C.T3B.T4F, T1F.T2C.T3B.T4G, T1F.T2C.T3B.T4H,
T1F.T2C.T3C.T4A, T1F.T2C.T3C.T4B, T1F.T2C.T3C.T4C, T1F.T2C.T3C.T4D,
T1F.T2C.T3C.T4E, T1F.T2C.T3C.T4F, T1F.T2C.T3C.T4G, T1F.T2C.T3C.T4H,
T1F.T2C.T3D.T4A, T1F.T2C.T3D.T4B, T1F.T2C.T3D.T4C, T1F.T2C.T3D.T4D,
T1F.T2C.T3D.T4E, T1F.T2C.T3D.T4F, T1F.T2C.T3D.T4G, T1F.T2C.T3D.T4H,
T1F.T2D.T3A.T4A, T1F.T2D.T3A.T4B, T1F.T2D.T3A.T4C, T1F.T2D.T3A.T4D,
T1F.T2D.T3A.T4E, T1F.T2D.T3A.T4F, T1F.T2D.T3A.T4G, T1F.T2D.T3A.T4H,
T1F.T2D.T3B.T4A, T1F.T2D.T3B.T4B, T1F.T2D.T3B.T4C, T1F.T2D.T3B.T4D,
T1F.T2D.T3B.T4E, T1F.T2D.T3B.T4F, T1F.T2D.T3B.T4G, T1F.T2D.T3B.T4H,
T1F.T2D.T3C.T4A, T1F.T2D.T3C.T4B, T1F.T2D.T3C.T4C, T1F.T2D.T3C.T4D,
T1F.T2D.T3C.T4E, T1F.T2D.T3C.T4F, T1F.T2D.T3C.T4G, T1F.T2D.T3C.T4H,
T1F.T2D.T3D.T4A, T1F.T2D.T3D.T4B, T1F.T2D.T3D.T4C, T1F.T2D.T3D.T4D,
T1F.T2D.T3D.T4E, T1F.T2D.T3D.T4F, T1F.T2D.T3D.T4G, T1F.T2D.T3D.T4H,
T1G.T2A.T3A.T4A, T1G.T2A.T3A.T4B, T1G.T2A.T3A.T4C, T1G.T2A.T3A.T4D,
T1G.T2A.T3A.T4E, T1G.T2A.T3A.T4F, T1G.T2A.T3A.T4G, T1G.T2A.T3A.T4H,
T1G.T2A.T3B.T4A, T1G.T2A.T3B.T4B, T1G.T2A.T3B.T4C, T1G.T2A.T3B.T4D,
T1G.T2A.T3B.T4E, T1G.T2A.T3B.T4F, T1G.T2A.T3B.T4G, T1G.T2A.T3B.T4H,
T1G.T2A.T3C.T4A, T1G.T2A.T3C.T4B, T1G.T2A.T3C.T4C, T1G.T2A.T3C.T4D,
T1G.T2A.T3C.T4E, T1G.T2A.T3C.T4F, T1G.T2A.T3C.T4G, T1G.T2A.T3C.T4H,
T1G.T2A.T3D.T4A, T1G.T2A.T3D.T4B, T1G.T2A.T3D.T4C, T1G.T2A.T3D.T4D,
T1G.T2A.T3D.T4E, T1G.T2A.T3D.T4F, T1G.T2A.T3D.T4G, T1G.T2A.T3D.T4H,
T1G.T2B.T3A.T4A, T1G.T2B.T3A.T4B, T1G.T2B.T3A.T4C, T1G.T2B.T3A.T4D,
T1G.T2B.T3A.T4E, T1G.T2B.T3A.T4F, T1G.T2B.T3A.T4G, T1G.T2B.T3A.T4H,
T1G.T2B.T3B.T4A, T1G.T2B.T3B.T4B, T1G.T2B.T3B.T4C, T1G.T2B.T3B.T4D,
T1G.T2B.T3B.T4E, T1G.T2B.T3B.T4F, T1G.T2B.T3B.T4G, T1G.T2B.T3B.T4H,
T1G.T2B.T3C.T4A, T1G.T2B.T3C.T4B, T1G.T2B.T3C.T4C, T1G.T2B.T3C.T4D,
T1G.T2B.T3C.T4E, T1G.T2B.T3C.T4F, T1G.T2B.T3C.T4G, T1G.T2B.T3C.T4H,
T1G.T2B.T3D.T4A, T1G.T2B.T3D.T4B, T1G.T2B.T3D.T4C, T1G.T2B.T3D.T4D,
T1G.T2B.T3D.T4E, T1G.T2B.T3D.T4F, T1G.T2B.T3D.T4G, T1G.T2B.T3D.T4H,
T1G.T2C.T3A.T4A, T1G.T2C.T3A.T4B, T1G.T2C.T3A.T4C, T1G.T2C.T3A.T4D,
T1G.T2C.T3A.T4E, T1G.T2C.T3A.T4F, T1G.T2C.T3A.T4G, T1G.T2C.T3A.T4H,
T1G.T2C.T3B.T4A, T1G.T2C.T3B.T4B, T1G.T2C.T3B.T4C, T1G.T2C.T3B.T4D,
T1G.T2C.T3B.T4E, T1G.T2C.T3B.T4F, T1G.T2C.T3B.T4G, T1G.T2C.T3B.T4H,
T1G.T2C.T3C.T4A, T1G.T2C.T3C.T4B, T1G.T2C.T3C.T4C, T1G.T2C.T3C.T4D,
T1G.T2C.T3C.T4E, T1G.T2C.T3C.T4F, T1G.T2C.T3C.T4G, T1G.T2C.T3C.T4H,
T1G.T2C.T3D.T4A, T1G.T2C.T3D.T4B, T1G.T2C.T3D.T4C, T1G.T2C.T3D.T4D,
T1G.T2C.T3D.T4E, T1G.T2C.T3D.T4F, T1G.T2C.T3D.T4G, T1G.T2C.T3D.T4H,
T1G.T2D.T3A.T4A, T1G.T2D.T3A.T4B, T1G.T2D.T3A.T4C, T1G.T2D.T3A.T4D,
T1G.T2D.T3A.T4E, T1G.T2D.T3A.T4F, T1G.T2D.T3A.T4G, T1G.T2D.T3A.T4H,
T1G.T2D.T3B.T4A, T1G.T2D.T3B.T4B, T1G.T2D.T3B.T4C, T1G.T2D.T3B.T4D,
T1G.T2D.T3B.T4E, T1G.T2D.T3B.T4F, T1G.T2D.T3B.T4G, T1G.T2D.T3B.T4H,
T1G.T2D.T3C.T4A, T1G.T2D.T3C.T4B, T1G.T2D.T3C.T4C, T1G.T2D.T3C.T4D,
T1G.T2D.T3C.T4E, T1G.T2D.T3C.T4F, T1G.T2D.T3C.T4G, T1G.T2D.T3C.T4H,
T1G.T2D.T3D.T4A, T1G.T2D.T3D.T4B, T1G.T2D.T3D.T4C, T1G.T2D.T3D.T4D,
T1G.T2D.T3D.T4E, T1G.T2D.T3D.T4F, T1G.T2D.T3D.T4G, T1G.T2D.T3D.T4H,

In still another embodiment, selected compounds of Formula I and II are named below in tabular format (Table 10) as compounds of general Formula IV (below):

$$X\text{-}A\text{-}Y\text{---}Z \qquad \text{Formula IV}$$

where X, A, Y, and Z are defined in Tables 6-9, below. Each compound is designated in tabular form by combining the "code" representing each structural moiety using the following syntax: X.A.Y.Z. Thus, for example, X1.A1.Y1.Z1 represents the following structure:

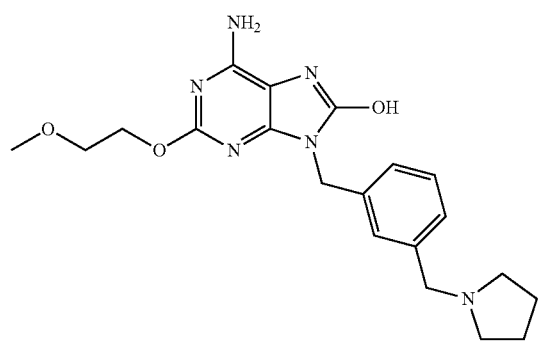 [SMILES: COCCOc1nc(N)c2nc(O)n(Cc3cccc(CN4CCCC4)c3)c2n1]

TABLE 6

"A" Structures

| Code | "A" Structure |
|---|---|
| A1 | (purine with NH₂, OH, X, Y-Z) |
| A2 | (purine with NH₂, ethyl, =O, X, Y-Z) |
| A3 | (purine with NH₂, O-C(=O)-O-iPr, X, Y-Z) |
| A4 | (purine with NH₂, O-C(=O)-NH-ethyl, X, Y-Z) |

TABLE 7

"X" Structures

| Code | "X" Structure |
|---|---|
| X1 | –O–CH₂CH₂–O–CH₃ |
| X2 | –O–CH₂CH₂CH₂CH₃ |
| X3 | –NH–CH₂CH₂CH₂CH₃ |
| X4 | –NH–CH₂–phenyl |
| X5 | –NH–CH₂CH₂–cyclopropyl |
| X6 | –NH–CH₂–CF₃ |

TABLE 8

"Y" Structures

| Code | "Y" Structure |
|---|---|
| Y1 | 1,3-bis(methylene)phenyl |
| Y2 | 1,3-phenylene with CH₂ and CH₂CH₂ |
| Y3 | cyclopropyl with CH₂ groups |
| Y4 | triazole linker |

TABLE 9

"Z" Structures

| Code | "Z" Structure |
|---|---|
| Z1 | Y–N(pyrrolidine) |

TABLE 9-continued

"Z" Structures

| Code | "Z" Structure |
|---|---|
| Z2 | Y—N(morpholine)O |
| Z3 | Y—N(piperazine)N—Me |
| Z4 | Y—N(piperazine)NH |
| Z5 | Y—NH—CH2-cyclopropyl |
| Z6 | Y-N(imidazole)N |
| Z7 | Y-N(diazepane)NH |
| Z8 | Y—NH-(2-pyridyl) |

TABLE 10

List of Compound Structures of Formula III

X1.A1.Y1.Z1, X1.A1.Y1.Z2, X1.A1.Y1.Z3, X1.A1.Y1.Z4, X1.A1.Y1.Z5, X1.A1.Y1.Z6,
X1.A1.Y1.Z7, X1.A1.Y1.Z8, X1.A1.Y2.Z1, X1.A1.Y2.Z2, X1.A1.Y2.Z3, X1.A1.Y2.Z4,
X1.A1.Y2.Z5, X1.A1.Y2.Z6, X1.A1.Y2.Z7, X1.A1.Y2.Z8, X1.A1.Y3.Z1, X1.A1.Y3.Z2,
X1.A1.Y3.Z3, X1.A1.Y3.Z4, X1.A1.Y3.Z5, X1.A1.Y3.Z6, X1.A1.Y3.Z7, X1.A1.Y3.Z8,
X1.A1.Y4.Z1, X1.A1.Y4.Z2, X1.A1.Y4.Z3, X1.A1.Y4.Z4, X1.A1.Y4.Z5, X1.A1.Y4.Z6,
X1.A1.Y4.Z7, X1.A1.Y4.Z8, X1.A2.Y1.Z1, X1.A2.Y1.Z2, X1.A2.Y1.Z3, X1.A2.Y1.Z4,
X1.A2.Y1.Z5, X1.A2.Y1.Z6, X1.A2.Y1.Z7, X1.A2.Y1.Z8, X1.A2.Y2.Z1, X1.A2.Y2.Z2,
X1.A2.Y2.Z3, X1.A2.Y2.Z4, X1.A2.Y2.Z5, X1.A2.Y2.Z6, X1.A2.Y2.Z7, X1.A2.Y2.Z8,
X1.A2.Y3.Z1, X1.A2.Y3.Z2, X1.A2.Y3.Z3, X1.A2.Y3.Z4, X1.A2.Y3.Z5, X1.A2.Y3.Z6,
X1.A2.Y3.Z7, X1.A2.Y3.Z8, X1.A2.Y4.Z1, X1.A2.Y4.Z2, X1.A2.Y4.Z3, X1.A2.Y4.Z4,
X1.A2.Y4.Z5, X1.A2.Y4.Z6, X1.A2.Y4.Z7, X1.A2.Y4.Z8, X1.A3.Y1.Z1, X1.A3.Y1.Z2,
X1.A3.Y1.Z3, X1.A3.Y1.Z4, X1.A3.Y1.Z5, X1.A3.Y1.Z6, X1.A3.Y1.Z7, X1.A3.Y1.Z8,
X1.A3.Y2.Z1, X1.A3.Y2.Z2, X1.A3.Y2.Z3, X1.A3.Y2.Z4, X1.A3.Y2.Z5, X1.A3.Y2.Z6,
X1.A3.Y2.Z7, X1.A3.Y2.Z8, X1.A3.Y3.Z1, X1.A3.Y3.Z2, X1.A3.Y3.Z3, X1.A3.Y3.Z4,
X1.A3.Y3.Z5, X1.A3.Y3.Z6, X1.A3.Y3.Z7, X1.A3.Y3.Z8, X1.A3.Y4.Z1, X1.A3.Y4.Z2,
X1.A3.Y4.Z3, X1.A3.Y4.Z4, X1.A3.Y4.Z5, X1.A3.Y4.Z6, X1.A3.Y4.Z7, X1.A3.Y4.Z8,
X1.A4.Y1.Z1, X1.A4.Y1.Z2, X1.A4.Y1.Z3, X1.A4.Y1.Z4, X1.A4.Y1.Z5, X1.A4.Y1.Z6,
X1.A4.Y1.Z7, X1.A4.Y1.Z8, X1.A4.Y2.Z1, X1.A4.Y2.Z2, X1.A4.Y2.Z3, X1.A4.Y2.Z4,
X1.A4.Y2.Z5, X1.A4.Y2.Z6, X1.A4.Y2.Z7, X1.A4.Y2.Z8, X1.A4.Y3.Z1, X1.A4.Y3.Z2,
X1.A4.Y3.Z3, X1.A4.Y3.Z4, X1.A4.Y3.Z5, X1.A4.Y3.Z6, X1.A4.Y3.Z7, X1.A4.Y3.Z8,
X1.A4.Y4.Z1, X1.A4.Y4.Z2, X1.A4.Y4.Z3, X1.A4.Y4.Z4, X1.A4.Y4.Z5, X1.A4.Y4.Z6,
X1.A4.Y4.Z7, X1.A4.Y4.Z8, X2.A1.Y1.Z1, X2.A1.Y1.Z2, X2.A1.Y1.Z3, X2.A1.Y1.Z4,
X2.A1.Y1.Z5, X2.A1.Y1.Z6, X2.A1.Y1.Z7, X2.A1.Y1.Z8, X2.A1.Y2.Z1, X2.A1.Y2.Z2,
X2.A1.Y2.Z3, X2.A1.Y2.Z4, X2.A1.Y2.Z5, X2.A1.Y2.Z6, X2.A1.Y2.Z7, X2.A1.Y2.Z8,
X2.A1.Y3.Z1, X2.A1.Y3.Z2, X2.A1.Y3.Z3, X2.A1.Y3.Z4, X2.A1.Y3.Z5, X2.A1.Y3.Z6,
X2.A1.Y3.Z7, X2.A1.Y3.Z8, X2.A1.Y4.Z1, X2.A1.Y4.Z2, X2.A1.Y4.Z3, X2.A1.Y4.Z4,
X2.A1.Y4.Z5, X2.A1.Y4.Z6, X2.A1.Y4.Z7, X2.A1.Y4.Z8, X2.A2.Y1.Z1, X2.A2.Y1.Z2,
X2.A2.Y1.Z3, X2.A2.Y1.Z4, X2.A2.Y1.Z5, X2.A2.Y1.Z6, X2.A2.Y1.Z7, X2.A2.Y1.Z8,
X2.A2.Y2.Z1, X2.A2.Y2.Z2, X2.A2.Y2.Z3, X2.A2.Y2.Z4, X2.A2.Y2.Z5, X2.A2.Y2.Z6,
X2.A2.Y2.Z7, X2.A2.Y2.Z8, X2.A2.Y3.Z1, X2.A2.Y3.Z2, X2.A2.Y3.Z3, X2.A2.Y3.Z4,
X2.A2.Y3.Z5, X2.A2.Y3.Z6, X2.A2.Y3.Z7, X2.A2.Y3.Z8, X2.A2.Y4.Z1, X2.A2.Y4.Z2,
X2.A2.Y4.Z3, X2.A2.Y4.Z4, X2.A2.Y4.Z5, X2.A2.Y4.Z6, X2.A2.Y4.Z7, X2.A2.Y4.Z8,
X2.A3.Y1.Z1, X2.A3.Y1.Z2, X2.A3.Y1.Z3, X2.A3.Y1.Z4, X2.A3.Y1.Z5, X2.A3.Y1.Z6,
X2.A3.Y1.Z7, X2.A3.Y1.Z8, X2.A3.Y2.Z1, X2.A3.Y2.Z2, X2.A3.Y2.Z3, X2.A3.Y2.Z4,
X2.A3.Y2.Z5, X2.A3.Y2.Z6, X2.A3.Y2.Z7, X2.A3.Y2.Z8, X2.A3.Y3.Z1, X2.A3.Y3.Z2,
X2.A3.Y3.Z3, X2.A3.Y3.Z4, X2.A3.Y3.Z5, X2.A3.Y3.Z6, X2.A3.Y3.Z7, X2.A3.Y3.Z8,
X2.A3.Y4.Z1, X2.A3.Y4.Z2, X2.A3.Y4.Z3, X2.A3.Y4.Z4, X2.A3.Y4.Z5, X2.A3.Y4.Z6,
X2.A3.Y4.Z7, X2.A3.Y4.Z8, X2.A4.Y1.Z1, X2.A4.Y1.Z2, X2.A4.Y1.Z3, X2.A4.Y1.Z4,
X2.A4.Y1.Z5, X2.A4.Y1.Z6, X2.A4.Y1.Z7, X2.A4.Y1.Z8, X2.A4.Y2.Z1, X2.A4.Y2.Z2,
X2.A4.Y2.Z3, X2.A4.Y2.Z4, X2.A4.Y2.Z5, X2.A4.Y2.Z6, X2.A4.Y2.Z7, X2.A4.Y2.Z8,
X2.A4.Y3.Z1, X2.A4.Y3.Z2, X2.A4.Y3.Z3, X2.A4.Y3.Z4, X2.A4.Y3.Z5, X2.A4.Y3.Z6,
X2.A4.Y3.Z7, X2.A4.Y3.Z8, X2.A4.Y4.Z1, X2.A4.Y4.Z2, X2.A4.Y4.Z3, X2.A4.Y4.Z4,
X2.A4.Y4.Z5, X2.A4.Y4.Z6, X2.A4.Y4.Z7, X2.A4.Y4.Z8, X3.A1.Y1.Z1, X3.A1.Y1.Z2,
X3.A1.Y1.Z3, X3.A1.Y1.Z4, X3.A1.Y1.Z5, X3.A1.Y1.Z6, X3.A1.Y1.Z7, X3.A1.Y1.Z8,
X3.A1.Y2.Z1, X3.A1.Y2.Z2, X3.A1.Y2.Z3, X3.A1.Y2.Z4, X3.A1.Y2.Z5, X3.A1.Y2.Z6,

TABLE 10-continued

List of Compound Structures of Formula III

X3.A1.Y2.Z7, X3.A1.Y2.Z8, X3.A1.Y3.Z1, X3.A1.Y3.Z2, X3.A1.Y3.Z3, X3.A1.Y3.Z4,
X3.A1.Y3.Z5, X3.A1.Y3.Z6, X3.A1.Y3.Z7, X3.A1.Y3.Z8, X3.A1.Y4.Z1, X3.A1.Y4.Z2,
X3.A1.Y4.Z3, X3.A1.Y4.Z4, X3.A1.Y4.Z5, X3.A1.Y4.Z6, X3.A1.Y4.Z7, X3.A1.Y4.Z8,
X3.A2.Y1.Z1, X3.A2.Y1.Z2, X3.A2.Y1.Z3, X3.A2.Y1.Z4, X3.A2.Y1.Z5, X3.A2.Y1.Z6,
X3.A2.Y1.Z7, X3.A2.Y1.Z8, X3.A2.Y2.Z1, X3.A2.Y2.Z2, X3.A2.Y2.Z3, X3.A2.Y2.Z4,
X3.A2.Y2.Z5, X3.A2.Y2.Z6, X3.A2.Y2.Z7, X3.A2.Y2.Z8, X3.A2.Y3.Z1, X3.A2.Y3.Z2,
X3.A2.Y3.Z3, X3.A2.Y3.Z4, X3.A2.Y3.Z5, X3.A2.Y3.Z6, X3.A2.Y3.Z7, X3.A2.Y3.Z8,
X3.A2.Y4.Z1, X3.A2.Y4.Z2, X3.A2.Y4.Z3, X3.A2.Y4.Z4, X3.A2.Y4.Z5, X3.A2.Y4.Z6,
X3.A2.Y4.Z7, X3.A2.Y4.Z8, X3.A3.Y1.Z1, X3.A3.Y1.Z2, X3.A3.Y1.Z3, X3.A3.Y1.Z4,
X3.A3.Y1.Z5, X3.A3.Y1.Z6, X3.A3.Y1.Z7, X3.A3.Y1.Z8, X3.A3.Y2.Z1, X3.A3.Y2.Z2,
X3.A3.Y2.Z3, X3.A3.Y2.Z4, X3.A3.Y2.Z5, X3.A3.Y2.Z6, X3.A3.Y2.Z7, X3.A3.Y2.Z8,
X3.A3.Y3.Z1, X3.A3.Y3.Z2, X3.A3.Y3.Z3, X3.A3.Y3.Z4, X3.A3.Y3.Z5, X3.A3.Y3.Z6,
X3.A3.Y3.Z7, X3.A3.Y3.Z8, X3.A3.Y4.Z1, X3.A3.Y4.Z2, X3.A3.Y4.Z3, X3.A3.Y4.Z4,
X3.A3.Y4.Z5, X3.A3.Y4.Z6, X3.A3.Y4.Z7, X3.A3.Y4.Z8, X3.A4.Y1.Z1, X3.A4.Y1.Z2,
X3.A4.Y1.Z3, X3.A4.Y1.Z4, X3.A4.Y1.Z5, X3.A4.Y1.Z6, X3.A4.Y1.Z7, X3.A4.Y1.Z8,
X3.A4.Y2.Z1, X3.A4.Y2.Z2, X3.A4.Y2.Z3, X3.A4.Y2.Z4, X3.A4.Y2.Z5, X3.A4.Y2.Z6,
X3.A4.Y2.Z7, X3.A4.Y2.Z8, X3.A4.Y3.Z1, X3.A4.Y3.Z2, X3.A4.Y3.Z3, X3.A4.Y3.Z4,
X3.A4.Y3.Z5, X3.A4.Y3.Z6, X3.A4.Y3.Z7, X3.A4.Y3.Z8, X3.A4.Y4.Z1, X3.A4.Y4.Z2,
X3.A4.Y4.Z3, X3.A4.Y4.Z4, X3.A4.Y4.Z5, X3.A4.Y4.Z6, X3.A4.Y4.Z7, X3.A4.Y4.Z8,
X4.A1.Y1.Z1, X4.A1.Y1.Z2, X4.A1.Y1.Z3, X4.A1.Y1.Z4, X4.A1.Y1.Z5, X4.A1.Y1.Z6,
X4.A1.Y1.Z7, X4.A1.Y1.Z8, X4.A1.Y2.Z1, X4.A1.Y2.Z2, X4.A1.Y2.Z3, X4.A1.Y2.Z4,
X4.A1.Y2.Z5, X4.A1.Y2.Z6, X4.A1.Y2.Z7, X4.A1.Y2.Z8, X4.A1.Y3.Z1, X4.A1.Y3.Z2,
X4.A1.Y3.Z3, X4.A1.Y3.Z4, X4.A1.Y3.Z5, X4.A1.Y3.Z6, X4.A1.Y3.Z7, X4.A1.Y3.Z8,
X4.A1.Y4.Z1, X4.A1.Y4.Z2, X4.A1.Y4.Z3, X4.A1.Y4.Z4, X4.A1.Y4.Z5, X4.A1.Y4.Z6,
X4.A1.Y4.Z7, X4.A1.Y4.Z8, X4.A2.Y1.Z1, X4.A2.Y1.Z2, X4.A2.Y1.Z3, X4.A2.Y1.Z4,
X4.A2.Y1.Z5, X4.A2.Y1.Z6, X4.A2.Y1.Z7, X4.A2.Y1.Z8, X4.A2.Y2.Z1, X4.A2.Y2.Z2,
X4.A2.Y2.Z3, X4.A2.Y2.Z4, X4.A2.Y2.Z5, X4.A2.Y2.Z6, X4.A2.Y2.Z7, X4.A2.Y2.Z8,
X4.A2.Y3.Z1, X4.A2.Y3.Z2, X4.A2.Y3.Z3, X4.A2.Y3.Z4, X4.A2.Y3.Z5, X4.A2.Y3.Z6,
X4.A2.Y3.Z7, X4.A2.Y3.Z8, X4.A2.Y4.Z1, X4.A2.Y4.Z2, X4.A2.Y4.Z3, X4.A2.Y4.Z4,
X4.A2.Y4.Z5, X4.A2.Y4.Z6, X4.A2.Y4.Z7, X4.A2.Y4.Z8, X4.A3.Y1.Z1, X4.A3.Y1.Z2,
X4.A3.Y1.Z3, X4.A3.Y1.Z4, X4.A3.Y1.Z5, X4.A3.Y1.Z6, X4.A3.Y1.Z7, X4.A3.Y1.Z8,
X4.A3.Y2.Z1, X4.A3.Y2.Z2, X4.A3.Y2.Z3, X4.A3.Y2.Z4, X4.A3.Y2.Z5, X4.A3.Y2.Z6,
X4.A3.Y2.Z7, X4.A3.Y2.Z8, X4.A3.Y3.Z1, X4.A3.Y3.Z2, X4.A3.Y3.Z3, X4.A3.Y3.Z4,
X4.A3.Y3.Z5, X4.A3.Y3.Z6, X4.A3.Y3.Z7, X4.A3.Y3.Z8, X4.A3.Y4.Z1, X4.A3.Y4.Z2,
X4.A3.Y4.Z3, X4.A3.Y4.Z4, X4.A3.Y4.Z5, X4.A3.Y4.Z6, X4.A3.Y4.Z7, X4.A3.Y4.Z8,
X4.A4.Y1.Z1, X4.A4.Y1.Z2, X4.A4.Y1.Z3, X4.A4.Y1.Z4, X4.A4.Y1.Z5, X4.A4.Y1.Z6,
X4.A4.Y1.Z7, X4.A4.Y1.Z8, X4.A4.Y2.Z1, X4.A4.Y2.Z2, X4.A4.Y2.Z3, X4.A4.Y2.Z4,
X4.A4.Y2.Z5, X4.A4.Y2.Z6, X4.A4.Y2.Z7, X4.A4.Y2.Z8, X4.A4.Y3.Z1, X4.A4.Y3.Z2,
X4.A4.Y3.Z3, X4.A4.Y3.Z4, X4.A4.Y3.Z5, X4.A4.Y3.Z6, X4.A4.Y3.Z7, X4.A4.Y3.Z8,
X4.A4.Y4.Z1, X4.A4.Y4.Z2, X4.A4.Y4.Z3, X4.A4.Y4.Z4, X4.A4.Y4.Z5, X4.A4.Y4.Z6,
X4.A4.Y4.Z7, X4.A4.Y4.Z8, X5.A1.Y1.Z1, X5.A1.Y1.Z2, X5.A1.Y1.Z3, X5.A1.Y1.Z4,
X5.A1.Y1.Z5, X5.A1.Y1.Z6, X5.A1.Y1.Z7, X5.A1.Y1.Z8, X5.A1.Y2.Z1, X5.A1.Y2.Z2,
X5.A1.Y2.Z3, X5.A1.Y2.Z4, X5.A1.Y2.Z5, X5.A1.Y2.Z6, X5.A1.Y2.Z7, X5.A1.Y2.Z8,
X5.A1.Y3.Z1, X5.A1.Y3.Z2, X5.A1.Y3.Z3, X5.A1.Y3.Z4, X5.A1.Y3.Z5, X5.A1.Y3.Z6,
X5.A1.Y3.Z7, X5.A1.Y3.Z8, X5.A1.Y4.Z1, X5.A1.Y4.Z2, X5.A1.Y4.Z3, X5.A1.Y4.Z4,
X5.A1.Y4.Z5, X5.A1.Y4.Z6, X5.A1.Y4.Z7, X5.A1.Y4.Z8, X5.A2.Y1.Z1, X5.A2.Y1.Z2,
X5.A2.Y1.Z3, X5.A2.Y1.Z4, X5.A2.Y1.Z5, X5.A2.Y1.Z6, X5.A2.Y1.Z7, X5.A2.Y1.Z8,
X5.A2.Y2.Z1, X5.A2.Y2.Z2, X5.A2.Y2.Z3, X5.A2.Y2.Z4, X5.A2.Y2.Z5, X5.A2.Y2.Z6,
X5.A2.Y2.Z7, X5.A2.Y2.Z8, X5.A2.Y3.Z1, X5.A2.Y3.Z2, X5.A2.Y3.Z3, X5.A2.Y3.Z4,
X5.A2.Y3.Z5, X5.A2.Y3.Z6, X5.A2.Y3.Z7, X5.A2.Y3.Z8, X5.A2.Y4.Z1, X5.A2.Y4.Z2,
X5.A2.Y4.Z3, X5.A2.Y4.Z4, X5.A2.Y4.Z5, X5.A2.Y4.Z6, X5.A2.Y4.Z7, X5.A2.Y4.Z8,
X5.A3.Y1.Z1, X5.A3.Y1.Z2, X5.A3.Y1.Z3, X5.A3.Y1.Z4, X5.A3.Y1.Z5, X5.A3.Y1.Z6,
X5.A3.Y1.Z7, X5.A3.Y1.Z8, X5.A3.Y2.Z1, X5.A3.Y2.Z2, X5.A3.Y2.Z3, X5.A3.Y2.Z4,
X5.A3.Y2.Z5, X5.A3.Y2.Z6, X5.A3.Y2.Z7, X5.A3.Y2.Z8, X5.A3.Y3.Z1, X5.A3.Y3.Z2,
X5.A3.Y3.Z3, X5.A3.Y3.Z4, X5.A3.Y3.Z5, X5.A3.Y3.Z6, X5.A3.Y3.Z7, X5.A3.Y3.Z8,
X5.A3.Y4.Z1, X5.A3.Y4.Z2, X5.A3.Y4.Z3, X5.A3.Y4.Z4, X5.A3.Y4.Z5, X5.A3.Y4.Z6,
X5.A3.Y4.Z7, X5.A3.Y4.Z8, X5.A4.Y1.Z1, X5.A4.Y1.Z2, X5.A4.Y1.Z3, X5.A4.Y1.Z4,
X5.A4.Y1.Z5, X5.A4.Y1.Z6, X5.A4.Y1.Z7, X5.A4.Y1.Z8, X5.A4.Y2.Z1, X5.A4.Y2.Z2,
X5.A4.Y2.Z3, X5.A4.Y2.Z4, X5.A4.Y2.Z5, X5.A4.Y2.Z6, X5.A4.Y2.Z7, X5.A4.Y2.Z8,
X5.A4.Y3.Z1, X5.A4.Y3.Z2, X5.A4.Y3.Z3, X5.A4.Y3.Z4, X5.A4.Y3.Z5, X5.A4.Y3.Z6,
X5.A4.Y3.Z7, X5.A4.Y3.Z8, X5.A4.Y4.Z1, X5.A4.Y4.Z2, X5.A4.Y4.Z3, X5.A4.Y4.Z4,
X5.A4.Y4.Z5, X5.A4.Y4.Z6, X5.A4.Y4.Z7, X5.A4.Y4.Z8, X6.A1.Y1.Z1, X6.A1.Y1.Z2,
X6.A1.Y1.Z3, X6.A1.Y1.Z4, X6.A1.Y1.Z5, X6.A1.Y1.Z6, X6.A1.Y1.Z7, X6.A1.Y1.Z8,
X6.A1.Y2.Z1, X6.A1.Y2.Z2, X6.A1.Y2.Z3, X6.A1.Y2.Z4, X6.A1.Y2.Z5, X6.A1.Y2.Z6,
X6.A1.Y2.Z7, X6.A1.Y2.Z8, X6.A1.Y3.Z1, X6.A1.Y3.Z2, X6.A1.Y3.Z3, X6.A1.Y3.Z4,
X6.A1.Y3.Z5, X6.A1.Y3.Z6, X6.A1.Y3.Z7, X6.A1.Y3.Z8, X6.A1.Y4.Z1, X6.A1.Y4.Z2,
X6.A1.Y4.Z3, X6.A1.Y4.Z4, X6.A1.Y4.Z5, X6.A1.Y4.Z6, X6.A1.Y4.Z7, X6.A1.Y4.Z8,
X6.A2.Y1.Z1, X6.A2.Y1.Z2, X6.A2.Y1.Z3, X6.A2.Y1.Z4, X6.A2.Y1.Z5, X6.A2.Y1.Z6,
X6.A2.Y1.Z7, X6.A2.Y1.Z8, X6.A2.Y2.Z1, X6.A2.Y2.Z2, X6.A2.Y2.Z3, X6.A2.Y2.Z4,
X6.A2.Y2.Z5, X6.A2.Y2.Z6, X6.A2.Y2.Z7, X6.A2.Y2.Z8, X6.A2.Y3.Z1, X6.A2.Y3.Z2,
X6.A2.Y3.Z3, X6.A2.Y3.Z4, X6.A2.Y3.Z5, X6.A2.Y3.Z6, X6.A2.Y3.Z7, X6.A2.Y3.Z8,

TABLE 10-continued

List of Compound Structures of Formula III

X6.A2.Y4.Z1, X6.A2.Y4.Z2, X6.A2.Y4.Z3, X6.A2.Y4.Z4, X6.A2.Y4.Z5, X6.A2.Y4.Z6,
X6.A2.Y4.Z7, X6.A2.Y4.Z8, X6.A3.Y1.Z1, X6.A3.Y1.Z2, X6.A3.Y1.Z3, X6.A3.Y1.Z4,
X6.A3.Y1.Z5, X6.A3.Y1.Z6, X6.A3.Y1.Z7, X6.A3.Y1.Z8, X6.A3.Y2.Z1, X6.A3.Y2.Z2,
X6.A3.Y2.Z3, X6.A3.Y2.Z4, X6.A3.Y2.Z5, X6.A3.Y2.Z6, X6.A3.Y2.Z7, X6.A3.Y2.Z8,
X6.A3.Y3.Z1, X6.A3.Y3.Z2, X6.A3.Y3.Z3, X6.A3.Y3.Z4, X6.A3.Y3.Z5, X6.A3.Y3.Z6,
X6.A3.Y3.Z7, X6.A3.Y3.Z8, X6.A3.Y4.Z1, X6.A3.Y4.Z2, X6.A3.Y4.Z3, X6.A3.Y4.Z4,
X6.A3.Y4.Z5, X6.A3.Y4.Z6, X6.A3.Y4.Z7, X6.A3.Y4.Z8, X6.A4.Y1.Z1, X6.A4.Y1.Z2,
X6.A4.Y1.Z3, X6.A4.Y1.Z4, X6.A4.Y1.Z5, X6.A4.Y1.Z6, X6.A4.Y1.Z7, X6.A4.Y1.Z8,
X6.A4.Y2.Z1, X6.A4.Y2.Z2, X6.A4.Y2.Z3, X6.A4.Y2.Z4, X6.A4.Y2.Z5, X6.A4.Y2.Z6,
X6.A4.Y2.Z7, X6.A4.Y2.Z8, X6.A4.Y3.Z1, X6.A4.Y3.Z2, X6.A4.Y3.Z3, X6.A4.Y3.Z4,
X6.A4.Y3.Z5, X6.A4.Y3.Z6, X6.A4.Y3.Z7, X6.A4.Y3.Z8, X6.A4.Y4.Z1, X6.A4.Y4.Z2,
X6.A4.Y4.Z3, X6.A4.Y4.Z4, X6.A4.Y4.Z5, X6.A4.Y4.Z6, X6.A4.Y4.Z7, X6.A4.Y4.Z8,

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 10 mg/kg body weight per day, typically from about 0.001 to about 1 mg/kg body weight per day, more typically from about 0.01 to about 1 mg/kg body weight per day, even more typically from about 0.05 to about 0.5 mg/kg body weight per day. For example, the daily candidate dose for an adult human of approximately 70 kg body weight will range from about 0.05 mg to about 100 mg, or between about 0.1 mg and about 25 mg, or between about 0.4 mg and about 4 mg, and may take the form of single or multiple doses.

In yet another embodiment, the present application discloses pharmaceutical compositions comprising a compound of Formula I, Ia, Ib, II, IIa, III, or IV, or a pharmaceutically acceptable salt, solvate, and/or ester thereof, and a pharmaceutically acceptable carrier or excipient.

In yet another embodiment, the present application discloses pharmaceutical compositions comprising a compound of Formula I, Ia, Ib, II, IIa, III, or IV, or a pharmaceutically acceptable salt, solvate, and/or ester thereof, in combination with at least one additional active agent, and a pharmaceutically acceptable carrier or excipient.

In yet another embodiment, the present application discloses pharmaceutical compositions comprising a compound of Formula I, Ia, Ib, II, IIa, III, or IV, or a pharmaceutically acceptable salt, solvate, and/or ester thereof, in combination with at least one additional active agent, and a pharmaceutically acceptable carrier or excipient. Examples of the additional active agent also include, but are not limited to interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

More specifically, one or more compounds of the present invention may be combined with one or more compounds selected from the group consisting of:

(1) interferons selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), belerofon, and mixtures thereof;

(2) ribavirin and its analogs selected from the group consisting of ribavirin (Rebetol, Copegus), taribavirin (Viramidine), and mixtures thereof;

(3) HCV NS3 protease inhibitors selected from the group consisting of boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, ITMN-191, and mixtures thereof;

(4) alpha-glucosidase 1 inhibitors selected from the group consisting of celgosivir (MX-3253), Miglitol, UT-231B, and mixtures thereof;

(5) hepatoprotectants selected from the group consisting of IDN-6556, ME 3738, LB-84451, silibilin, MitoQ, and mixtures thereof;

(6) nucleoside or nucleotide inhibitors of HCV NS5B polymerase selected from the group consisting of R1626, R7128 (R4048), IDX184, IDX-102, BCX-4678, valopicitabine (NM-283), MK-0608, and mixtures thereof;

(7) non-nucleoside inhibitors of HCV NS5B polymerase selected from the group consisting of PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, GS-9190, and mixtures thereof;

(8) HCV NS5A inhibitors selected from the group consisting of AZD-2836 (A-831), A-689, and mixtures thereof;

(9) TLR-7 agonists selected from the group consisting of ANA-975, SM-360320, and mixtures thereof;

(10) cyclophillin inhibitors selected from the group consisting of DEBIO-025, SCY-635, NIM811, and mixtures thereof;

(11) HCV IRES inhibitors selected from the group consisting of MCI-067,

(12) pharmacokinetic enhancers selected from the group consisting of BAS-100, SPI-452, PF-4194477, TMC-41629, roxythromycin, and mixtures thereof; and

(13) other drugs for treating HCV selected from the group consisting of thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib), and mixtures thereof.

In yet another embodiment, the present application provides a combination pharmaceutical agent comprising:

a) a first pharmaceutical composition comprising a compound of Formula I, Ia, Ib, II, IIa, III, or IV, or a pharmaceutically acceptable salt, solvate, or ester thereof; and b) a second pharmaceutical composition comprising at least one additional active agent selected from the group consisting of interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention are used in combination with other active therapeutic ingredients or agents. Combinations of the compounds of Formula I, Ia, Ib, II, IIa, III, or IV, and additional active agents may be selected to treat patients with a viral infection, e.g., HBV, HCV, or HIV infection.

Preferably, the other active therapeutic ingredients or agents are interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof. Combinations of the compounds of Formula I, Ia, Ib, II, IIa, III, or IV, are typically selected based on the condition to be treated, cross-reactivities of ingredients and pharmaco-properties of the combination. For example, when treating an infection (e.g., HCV), the compositions of the invention are combined with other active agents (such as those described herein).

Suitable active agents or ingredients which can be combined with the compounds of Formula I, Ia, Ib, II, IIa, III, or IV, can include one or more compounds selected from the group consisting of:

(1) interferons selected from the group consisting of pegylated rIFN-alpha 2b (PEG-Intron), pegylated rIFN-alpha 2a (Pegasys), rIFN-alpha 2b (IntronA), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), belerofon, and mixtures thereof;

(2) ribavirin and its analogs selected from the group consisting of ribavirin (Rebetol, Copegus), taribavirin (Viramidine), and mixtures thereof;

(3) HCV NS3 protease inhibitors selected from the group consisting of boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, ITMN-191, and mixtures thereof;

(4) alpha-glucosidase 1 inhibitors selected from the group consisting of celgosivir (MX-3253), Miglitol, UT-231B, and mixtures thereof;

(5) hepatoprotectants selected from the group consisting of IDN-6556, ME 3738, LB-84451, silibilin, MitoQ, and mixtures thereof;

(6) nucleoside or nucleotide inhibitors of HCV NS5B polymerase selected from the group consisting of R1626, R7128 (R4048), IDX184, IDX-102, BCX-4678, valopicitabine (NM-283), MK-0608, and mixtures thereof;

(7) non-nucleoside inhibitors of HCV NS5B polymerase selected from the group consisting of PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, GS-9190, and mixtures thereof;

(8) HCV NS5A inhibitors selected from the group consisting of AZD-2836 (A-831), A-689, and mixtures thereof;

(9) TLR-7 agonists selected from the group consisting of ANA-975, SM-360320, and mixtures thereof;

(10) cyclophillin inhibitors selected from the group consisting of DEBIO-025, SCY-635, NIM811, and mixtures thereof;

(11) HCV IRES inhibitors selected from the group consisting of MCI-067,

(12) pharmacokinetic enhancers selected from the group consisting of BAS-100, SPI-452, PF-4194477, TMC-41629, roxythromycin, and mixtures thereof; and

(13) other drugs for treating HCV selected from the group consisting of thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib), and mixtures thereof.

In yet another embodiment, the present application discloses pharmaceutical compositions comprising a compound of the present invention, or a pharmaceutically acceptable salt, solvate, and/or ester thereof, in combination with at least one additional active agent, and a pharmaceutically acceptable carrier or excipient.

According to the present invention, the active agent used in combination with the compound of the present invention can be any agent having a therapeutic effect when used in combination with the compound of the present invention. For example, the active agent used in combination with the compound of the present invention can be interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

In another embodiment, the present application provides pharmaceutical compositions comprising a compound of the present invention, or a pharmaceutically acceptable salt, solvate, and/or ester thereof, in combination with at least one additional active agent selected from the group consisting of:

(1) interferons selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), belerofon, and mixtures thereof;

(2) ribavirin and its analogs selected from the group consisting of ribavirin (Rebetol, Copegus), taribavirin (Viramidine), and mixtures thereof;

(3) HCV NS3 protease inhibitors selected from the group consisting of boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, ITMN-191, and mixtures thereof;

(4) alpha-glucosidase 1 inhibitors selected from the group consisting of celgosivir (MX-3253), Miglitol, UT-231B, and mixtures thereof;

(5) hepatoprotectants selected from the group consisting of IDN-6556, ME 3738, LB-84451, silibilin, MitoQ, and mixtures thereof;

(6) nucleoside or nucleotide inhibitors of HCV NS5B polymerase selected from the group consisting of R1626, R7128 (R4048), IDX184, IDX-102, BCX-4678, valopicitabine (NM-283), MK-0608, and mixtures thereof;

(7) non-nucleoside inhibitors of HCV NS5B polymerase selected from the group consisting of PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, GS-9190, and mixtures thereof;

(8) HCV NS5A inhibitors selected from the group consisting of AZD-2836 (A-831), A-689, and mixtures thereof;

(9) TLR-7 agonists selected from the group consisting of ANA-975, SM-360320, and mixtures thereof;

(10) cyclophillin inhibitors selected from the group consisting of DEBIO-025, SCY-635, NIM811, and mixtures thereof;

(11) HCV IRES inhibitors selected from the group consisting of MCI-067,

(12) pharmacokinetic enhancers selected from the group consisting of BAS-100, SPI-452, PF-4194477, TMC-41629, roxythromycin, and mixtures thereof; and

(13) other drugs for treating HCV selected from the group consisting of thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib), and mixtures thereof.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional active agent selected from the group consisting of interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In still yet another embodiment, the present application provides for methods of treating a viral infection in a patient, comprising: administering to the patient a therapeutically effective amount of a compound of Formula I, Ia, Ib, II, IIa, III, or IV, or a pharmaceutically acceptable salt, solvate, and/or ester thereof.

In still yet another embodiment, the present application provides for methods of treating a viral infection in a patient, comprising: administering to the patient a therapeutically effective amount of a compound of Formula I, Ia, Ib, II, IIa, III, or IV, or a pharmaceutically acceptable salt, solvate, and/or ester thereof, and at least one additional active agent.

In still yet another embodiment, the present application provides for methods of treating HCV in a patient, comprising: administering to the patient a therapeutically effective amount of a compound of Formula I, Ia, Ib, II, IIa, III, or IV, or a pharmaceutically acceptable salt, solvate, and/or ester thereof.

In still yet another embodiment, the present application provides for methods of treating HCV in a patient, comprising: administering to the patient a therapeutically effective amount of a compound of Formula I, Ia, Ib, II, IIa, III, or IV, or a pharmaceutically acceptable salt, solvate, and/or ester thereof, and at least one additional active agent which inhibits HCV polymerase.

In still yet another embodiment, the present application provides for methods of treating HCV in a patient, comprising: administering to the patient a therapeutically effective amount of a compound of Formula I, Ia, Ib, II, IIa, III, or IV, or a pharmaceutically acceptable salt, solvate, and/or ester thereof, and at least one additional active agent selected from the group consisting of interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

In still yet another embodiment, the present application provides for the use of a compound of the present invention, or a pharmaceutically acceptable salt, solvate, and/or ester thereof, for the preparation of a medicament for treating a viral infection, e.g., an HBV/HCV infection.

In yet another embodiment, the present application provides a method for treating or preventing a viral infection comprising co-administering, to a patient in need thereof, a therapeutically effective amount of at least one compound of Formula I, Ia, Ib, II, IIa, III, or IV, and at least one additional active agent selected from the group consisting of:

(1) interferons selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), belerofon, and mixtures thereof;

(2) ribavirin and its analogs selected from the group consisting of ribavirin (Rebetol, Copegus), taribavirin (Viramidine), and mixtures thereof;

(3) HCV NS3 protease inhibitors selected from the group consisting of boceprevir (SCH-503034, SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, ITMN-191, and mixtures thereof;

(4) alpha-glucosidase 1 inhibitors selected from the group consisting of celgosivir (MX-3253), Miglitol, UT-231B, and mixtures thereof;

(5) hepatoprotectants selected from the group consisting of IDN-6556, ME 3738, LB-84451, silibilin, MitoQ, and mixtures thereof;

(6) nucleoside or nucleotide inhibitors of HCV NS5B polymerase selected from the group consisting of R1626, R7128 (R4048), IDX184, IDX-102, BCX-4678, valopicitabine (NM-283), MK-0608, and mixtures thereof;

(7) non-nucleoside inhibitors of HCV NS5B polymerase selected from the group consisting of PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, GS-9190, and mixtures thereof;

(8) HCV NS5A inhibitors selected from the group consisting of AZD-2836 (A-831), A-689, and mixtures thereof;

(9) TLR-7 agonists selected from the group consisting of ANA-975, SM-360320, and mixtures thereof;

(10) cyclophillin inhibitors selected from the group consisting of DEBIO-025, SCY-635, NIM811, and mixtures thereof;

(11) HCV IRES inhibitors selected from the group consisting of MCI-067,

(12) pharmacokinetic enhancers selected from the group consisting of BAS-100, SPI-452, PF-4194477, TMC-41629, roxythromycin, and mixtures thereof; and

(13) other drugs for treating HCV selected from the group consisting of thymosin alpha 1 (Zadaxin), nitazoxanide (Alinea, NTZ), BIVN-401 (virostat), PYN-17 (altirex), KPE02003002, actilon (CPG-10101), KRN-7000, civacir, GI-5005, XTL-6865, BIT225, PTX-111, ITX2865, TT-033i, ANA 971, NOV-205, tarvacin, EHC-18, VGX-410C, EMZ- 702, AVI 4065, BMS-650032, BMS-791325, Bavituximab, MDX-1106 (ONO-4538), Oglufanide, VX-497 (merimepodib), and mixtures thereof.

In yet another embodiment, the present application provides a method for modulating toll-like receptor 7, comprising contacting a cell having a toll-like receptor 7 with an effective amount of a compound of Formula I, Ia, Ib, II, IIa, III, or IV or a pharmaceutically acceptable salt, solvate, and/or ester thereof. The term "modulating" refers to contacting the toll-like receptor 7 with a compound of Formula I, Ia, Ib, II, III, or IV which is e.g., an agonist or partial agonist of toll-like receptor 7.

In yet another embodiment, the present application provides a method for inducing interferon (or IFN-a) production in a patient in need thereof, comprising administering to the patient, a therapeutically effective amount of at least one compound of Formula I, Ia, Ib, II, IIa, III, or IV, or a pharmaceutically acceptable salt, solvate, and/or ester thereof.

EXAMPLES

Synthesis of Example A

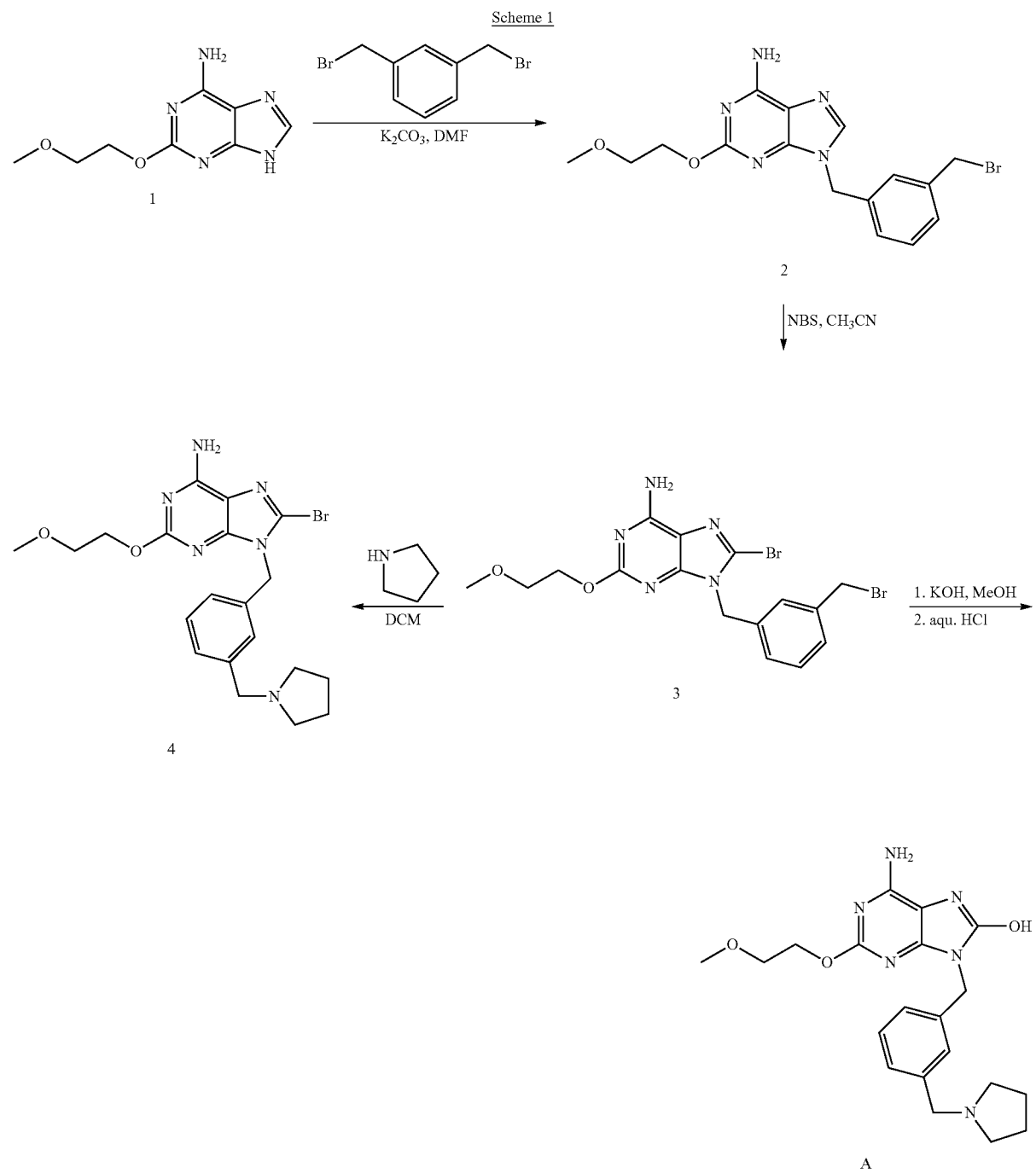

Compound 2

2-(2-Methoxy-ethoxy)-9H-purin-6-ylamine (1 g, 4.78 mmol) (1), α,α'-dibromo-m-xylene (2.52 g, 9.56 mmol) and anhydrous potassium carbonate (1.32 g, 9.56 mmol) were combined in DMF (10 mL) and stirred at ambient temperature for 5 hours. The reaction mixture was diluted with ethyl acetate (120 mL), washed with water (2×), brine, dried with Na$_2$SO$_4$, and evaporated under vacuum. The crude product was purified by chromatography on silica gel with 0-10% methanol in ethyl acetate as eluent. Evaporation of the appropriate fractions gave 9-(3-Bromomethyl-benzyl)-2-(2-methoxy-ethoxy)-9H-purin-6-ylamine (2) (1.1 g, 2.80 mmol, 59%). MS: 392/394 (MH$^+$).

Compound 3

9-(3-Bromomethyl-benzyl)-2-(2-methoxy-ethoxy)-9H-purin-6-ylamine (2) (1 g, 2.54 mmol) was dissolved in acetonitrile (10 mL). N-bromosuccinimide (1.5 g, 8.4 mmol) was added in portions over 5 min. The mixture was stirred at ambient temperature for 1 hour, then diluted with ethyl acetate (100 mL), washed with 10% aqueous Na$_2$S$_2$O$_3$ solution, and brine, dried with Na$_2$SO$_4$, and evaporated under vacuum. The crude 8-Bromo-9-(3-bromomethyl-benzyl)-2-(2-methoxy-ethoxy)-9H-purin-6-ylamine (3) (~1 g) was used in the next step without further purification.

Example A

Crude 8-Bromo-9-(3-bromomethyl-benzyl)-2-(2-methoxy-ethoxy)-9H-purin-6-ylamine (3) (~1 g) was dissolved in dichloromethane (10 mL) and pyrrolidine (1 mL) was added. The reaction mixture was stirred at ambient temperature overnight and then evaporated under vacuum. The residue (4) was dissolved in methanol (20 mL) and 50% aqueous KOH (2 mL) was added. The mixture was heated under reflux until HPLC analysis indicated complete disappearance of starting material (~3 hours). Then the mixture was cooled to ambient temperature and concentrated aq. HCl was added (5 mL). Heating under reflux was continued for 1 hour after which the reaction mixture was evaporated to dryness under vacuum. The solid residue was extracted 3× with methanol to separate from salts. The methanol solution was evaporated under vacuum and the crude product was purified by reverse phase preparative HPLC (5-45% acetonitrile/40 mM aqueous HCl) giving 6-Amino-2-(2-methoxy-ethoxy)-9-(3-pyrrolidin-1-ylmethyl-benzyl)-9H-purin-8-ol (Example A) (450 mg, 1.13 mmol) as yellowish solid as the HCl salt.

$^1$H-NMR (DMSO) δ: 10.09 (s, 1H), 9.78 (br, 1H), 7.47-7.33 (m, 4H), 6.54 (br, 2H), 4.87 (s, 2H), 4.32 (d, J=5.1, 2H), 4.23 (t, J=4.5 Hz, 2H), 3.56 (t, J=4.5 Hz, 2H), 3.25 (s, 3H), 3.38-3.00 (m, 4H), 2.05-1.75 (m, 4H). MS: 399 (MH$^+$).

Examples B, C, D, E, F, G, H, I, J, K, L, M, and N were prepared using procedures similar to those used to prepare Example A except that pyrrolidine was replaced with the appropriate amine for each of these examples.

Example B

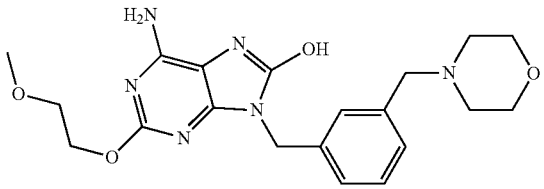

B

6-Amino-2-(2-methoxy-ethoxy)-9-(3-morpholin-4-ylmethyl-benzyl)-9H-purin-8-ol $^1$H-NMR (DMSO) δ: 10.08 (s, 1H), 9.85 (br, 1H), 7.55-7.35 (m, 4H), 6.53 (br, 2H), 4.89 (s, 2H), 4.32 (s, 2H), 4.23 (t, J=4.5 Hz, 2H), 3.98-3.89 (m, 2H), 3.66-3.52 (m, 4H), 3.25 (s, 3H), 3.25-3.02 (m, 4H). MS: 415 (MH$^+$).

Example C

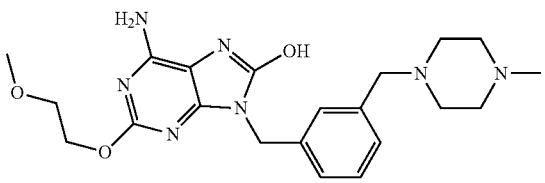

C

6-Amino-2-(2-methoxy-ethoxy)-9-[3-(4-methyl-piperazin-1-ylmethyl)-benzyl]-9H-purin-8-ol $^1$H-NMR (DMSO) δ: 11.6 (br, 2H), 10.75 (s, 1H), 7.59-7.33 (m, 4H), 4.89 (s, 2H), 4.37-4.28 (m, 4H), 3.60-3.27 (m, 10H), 3.26 (s, 3H), 2.80 (s, 3H). MS: 428 (MH$^+$).

Example D

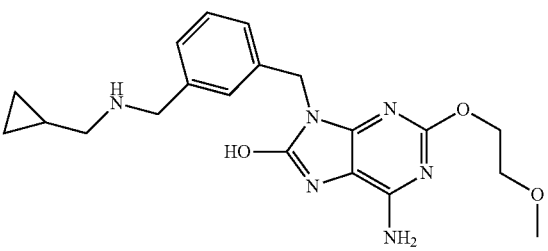

D

6-Amino-9-{3-[(cyclopropylmethyl-amino)-methyl]-benzyl}-2-(2-methoxy-ethoxy)-9H-purin-8-ol $^1$H-NMR (DMSO) δ: 10.89 (s, 1H), 9.18 (br, 2H), 7.50-7.32 (m, 4H), 5.58 (br, 2H), 4.89 (s, 2H), 4.32 (t, J=4 Hz, 2H), 4.09 (t, J=4.5 Hz, 2H), 3.59 (t, J=4.5 Hz, 2H), 3.26 (s, 3H), 2.80-2.74 (m, 2H), 1.10-1.03 (m, 1H), 0.57-0.52 (m, 2H), 0.34-0.30 (m, 2H). MS: 399 (MH$^+$).

Example E

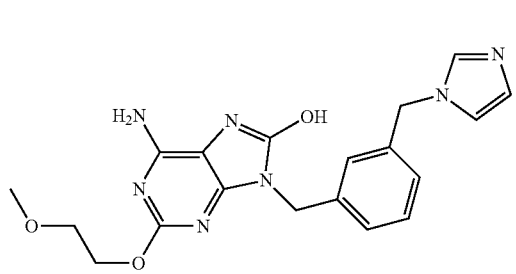

6-Amino-9-(3-imidazol-1-ylmethyl-benzyl)-2-(2-methoxy-ethoxy)-9H-purin-8-ol $^1$H-NMR (DMSO) δ: 10.85 (s, 1H), 9.28 (s, 1H), 7.76 (s, 1H), 7.68 (s, 1H), 7.40-7.26 (m, 4H), 5.42 (s, 2H), 5.40 (br, 2H), 4.87 (s, 2H), 4.29 (t, J=4.5 Hz, 2H), 3.59 (t, J=4.5 Hz, 2H), 3.26 (s, 3H). MS: 396 (MH$^+$).

Example F

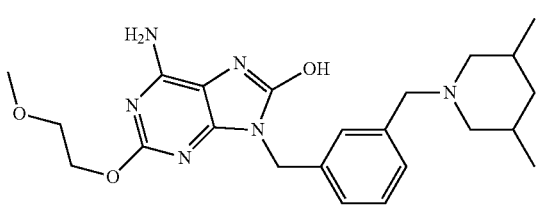

6-Amino-9-[3-(3,5-dimethyl-piperidin-1-ylmethyl)-benzyl]-2-(2-methoxy-ethoxy)-9H-purin-8-ol (mixture of cis and trans); MS: 441 (MH$^+$).

Example G

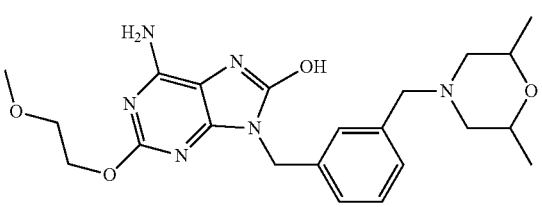

6-Amino-9-[3-(2,6-dimethyl-morpholin-4-ylmethyl)-benzyl]-2-(2-methoxy-ethoxy)-9H-purin-8-ol $^1$H-NMR (DMSO) δ: 11.31 (br, 1H), 10.90 (s, 1H), 7.60-7.36 (m, 4H), 5.10 (br, 2H), 4.91 (s, 2H), 4.33 (t, J=4.5 Hz, 2H), 4.26 (m, 2H), 3.98-3.89 (m, 2H), 3.59 (t, J=4.5 Hz, 2H), 3.26 (s, 3H), 3.18 (d, J=11.7 Hz, 2H), 2.65-2.50 (m, 2H), 1.07 (d, J=6.3 Hz, 6H). MS: 443 (MH$^+$).

Example H

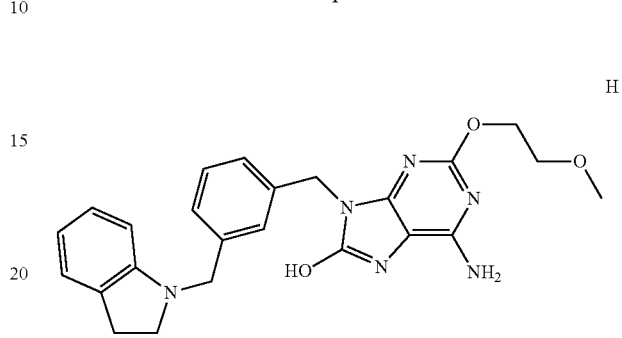

6-Amino-9-[3-(2,3-dihydro-indol-1-ylmethyl)-benzyl]-2-(2-methoxy-ethoxy)-9H-purin-8-ol $^1$H-NMR (DMSO) δ: 9.94 (s, 1H), 7.32-7.15 (m, 4H), 7.01 (d, J=6.9 Hz, 1H), 6.93 (t, J=7.2 Hz, 1H), 6.59-6.49 (m, 2H), 6.46 (s, 2H), 4.84 (s, 2H), 4.23 (t, J=4.5 Hz, 2H), 4.21 (s, 2H), 3.55 (t, J=4.5 Hz, 2H), 3.25 (s, 3H), 3.19 (t, J=8.4 Hz, 2H), 2.85 (t, J=8.4 Hz, 2H). MS: 447 (MH$^+$).

Example I

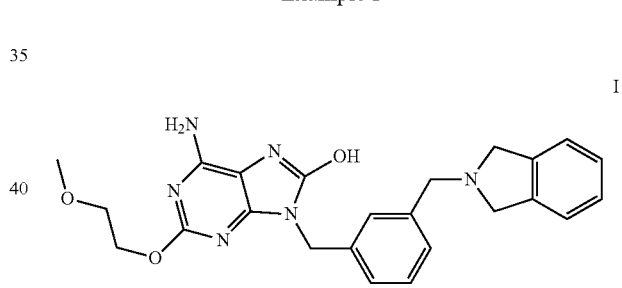

6-Amino-9-[3-(1,3-dihydro-isoindol-2-ylmethyl)-benzyl]-2-(2-methoxy-ethoxy)-9H-purin-8-ol $^1$H-NMR (DMSO) δ: 11.31 (br, 1H), 10.42 (s, 1H), 7.63-7.34 (m, 8H), 6.77 (br, 2H), 4.91 (s, 2H), 4.60-4.52 (m, 6H), 4.26 (t, J=4.5 Hz, 2H), 3.56 (t, J=4.5 Hz, 2H), 3.24 (s, 3H). MS: 447 (MH$^+$).

Example J

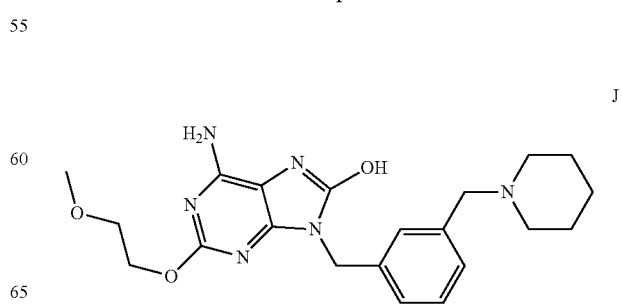

6-Amino-2-(2-methoxy-ethoxy)-9-(3-piperidin-1-ylmethyl-benzyl)-9H-purin-8-ol

¹H-NMR (DMSO) δ: 10.67 (s, 1H), 10.08 (br, 1H), 7.51-7.34 (m, 4H), 4.90 (s, 2H), 4.51 (br, 2H), 4.30-4.20 (m, 4H), 3.57 (t, J=4.5 Hz, 2H), 3.25 (s, 3H), 3.30-3.20 (m, 2H), 2.87-2.74 (m, 2H), 1.80-1.25 (m, 6H). MS: 413 (MH⁺).

Example K

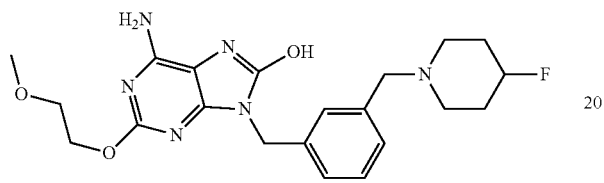

6-Amino-9-[3-(4-fluoro-piperidin-1-ylmethyl)-benzyl]-2-(2-methoxy-ethoxy)-9H-purin-8-ol ¹H-NMR (DMSO) δ: 10.90 (s, 1H), 10.85 (br, 1H), 7.58-7.34 (m, 4H), 4.91 (s, 2H), 4.30-4.20 (m, 4H), 3.59 (t, J=4.5 Hz, 2H), 3.26 (s, 3H), 3.30-2.90 (m, 5H), 2.25-1.95 (m, 4H). MS: 431 (MH⁺).

Example L

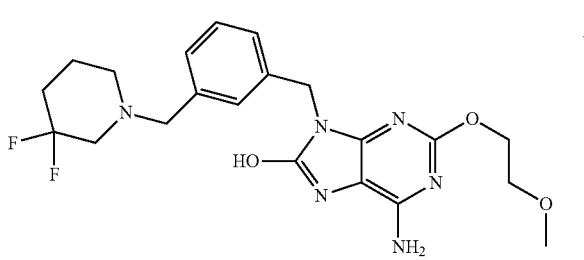

6-Amino-9-[3-(3,3-difluoro-piperidin-1-ylmethyl)-benzyl]-2-(2-methoxy-ethoxy)-9H-purin-8-ol ¹H-NMR (DMSO) δ: 11.05 (br, 1H), 11.00 (s, 1H), 7.53-7.38 (m, 4H), 4.92 (s, 2H), 4.38-4.29 (m, 4H), 3.59 (t, J=4.5 Hz, 2H), 3.55-3.45 (m, 2H), 3.26 (s, 3H), 3.05-2.90 (m, 2H), 2.20-1.85 (m, 4H). MS: 449 (MH⁺).

Example M

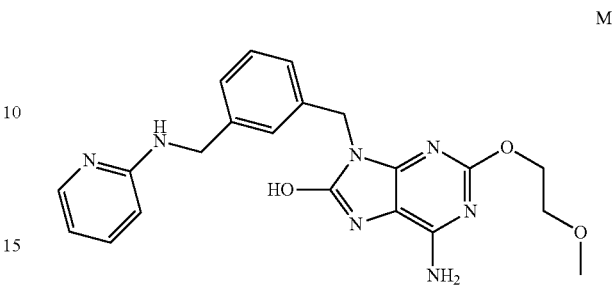

9-(3-((pyridin-2-ylamino)methyl)benzyl)-6-amino-2-(2-methoxyethoxy)-9H-purin-8-ol ¹H-NMR (DMSO) δ: 10.47 (s, 1H), 8.53 (br, 2H), 8.09 (d, J=6.3 Hz, 1H), 7.90 (t, J=7.5 Hz, 1H), 7.37 (t, J=8 Hz, 1H) 7.28 (d, J=7.5 Hz, 1H) 7.12-7.03 (m, 3H), 6.91 (t, J=7.5 Hz, 1H), 5.42 (s, 2H), 4.84 (s, 2H), 4.25 (t, J=4.5 Hz, 2H), 3.59 (t, J=4.5 Hz, 2H), 3.27 (s, 3H). MS: 422 (MH⁺).

Example N

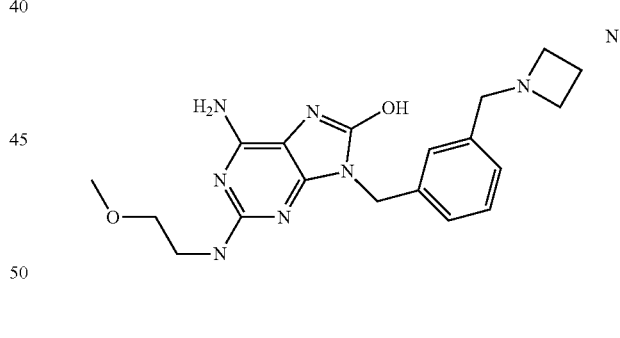

9-(3-(azetidin-1-ylmethyl)benzyl)-6-amino-2-(2-methoxyethoxy)-9H-purin-8-ol

¹H NMR (DMSO) δ: 2.17-2.41 (m, 2H), 3.25 (s, 3H), 3.59 (t, 3H, J=4.5 Hz), 3.82-4.02 (m, 4H), 4.28 (d, 2H, J=6 Hz), 4.39 (t, 2H, J=4.5 Hz), 4.90 (s, 2H), 7.35-7.44 (m, 4H), 11.32 (s, 1H). LCMS: m/z for $C_{19}H_{24}N_6O_3^+$+H observed 385.2 at 1.61 minutes of a 3.5 minute run, gradient 5-95% $CH_3CN$ in $H_2O$.

Synthesis of Example O

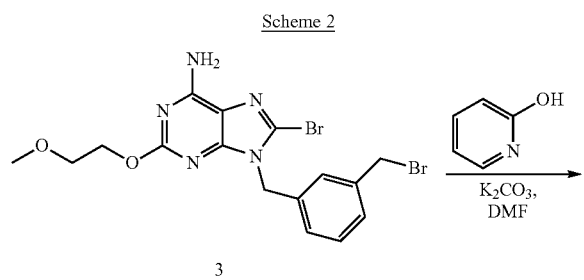

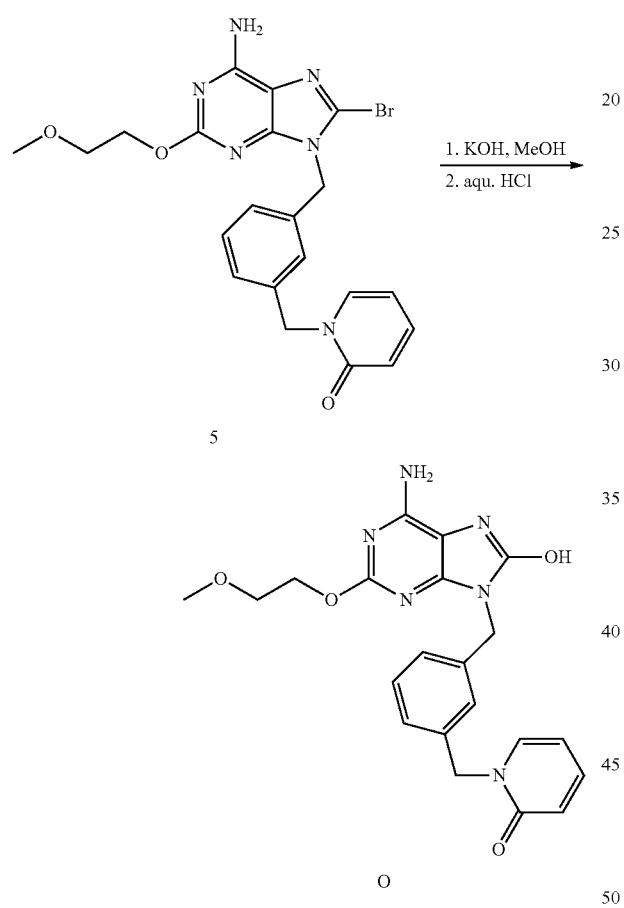

Compound 5

Crude 8-Bromo-9-(3-bromomethyl-benzyl)-2-(2-methoxy-ethoxy)-9H-purin-6-ylamine (~70 mg) was dissolved in DMF (2 mL). 2-Hydroxypyridine (100 mg) and anhydrous potassium carbonate (100 mg) was added and the reaction mixture was stirred overnight. After dilution with ethyl acetate (100 mL), the solution was washed with water and brine, dried with Na$_2$SO$_4$ and evaporated under vacuum. The crude product (5) was converted to 1-((3-((6-amino-8-hydroxy-2-(2-methoxyethoxy)-9H-purin-9-yl)methyl)phenyl)methyl)pyridin-2(1H)-one (Example O, 41 mg) using procedures similar to those used to convert Compound 4 to Example A $^1$H-NMR (DMSO) δ: 10.54 (s, 1H), 7.72 (d, J=7 Hz, 1H), 7.40 (t, J=7 Hz, 1H), 7.29 (t, J=7.2 Hz, 1H), 7.22-7.11 (m, 3H), 6.38 (d, J=9 Hz, 1H), 6.20 (t, J=6.6 Hz, 1H), 5.06 (s, 2H), 4.84 (s, 2H), 4.31 (t, J=4.5 Hz, 2H), 3.60 (t, J=4.5 Hz, 2H), 3.27 (s, 3H). MS: 423 (MH$^+$).

Synthesis of Example P

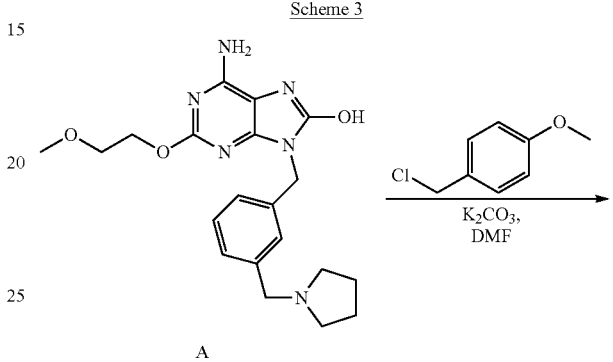

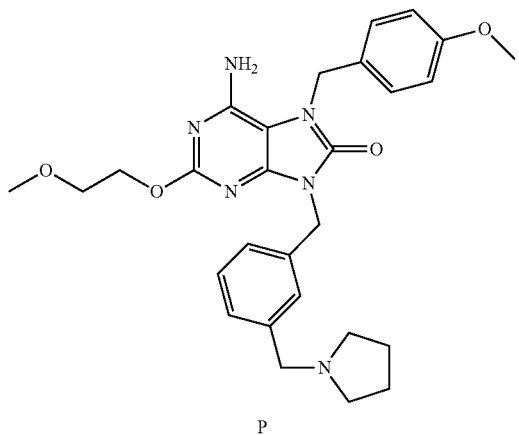

Example P

6-Amino-2-(2-methoxy-ethoxy)-9-(3-pyrrolidin-1-ylmethyl-benzyl)-9H-purin-8-ol (Example A) (31 mg, 0.078 mmol) was dissolved in DMF (2 mL). Anhydrous potassium carbonate (50 mg) was added followed by p-methoxybenzyl chloride (13.7 μL, 0.101 mmol). The mixture was stirred at ambient temperature overnight. The reaction mixture was diluted with dichloromethane, washed with water and brine, dried with Na$_2$SO$_4$ and evaporated under vacuum. Purification by preparative HPLC (5-60% acetonitrile/40 mM aqueous HCl) gave 6-amino-7-(4-methoxy-benzyl)-2-(2-methoxy-ethoxy)-9-(3-pyrrolidin-1-ylmethyl-benzyl)-7,9-dihydro-purin-8-one (Example P) (6 mg) as the HCl salt.

¹H-NMR (CDCl₃) δ: 12.54 (br, 1H), 7.85-6.88 (m, 10H), 5.24 (s, 2H), 5.14 (s, 2H), 4.66 (s, 2H), 4.20 (br, 2H), 3.81 (s, 3H), 3.72 (br, 2H), 3.58 (br, 2H), 3.36 (s, 3H), 2.85 (br, 2H), 2.25-2.00 (m, 4H). MS: 519 (MH⁺).

Synthesis of Example Q

Scheme 4

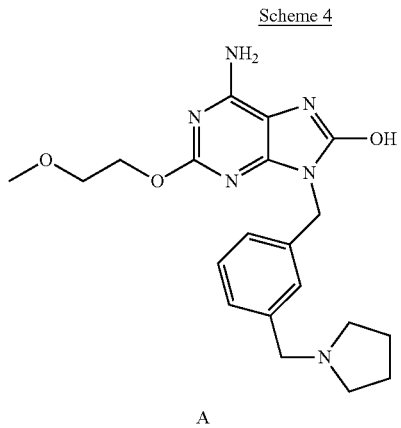

A

EtOC(O)Cl
DIPEA, DCM

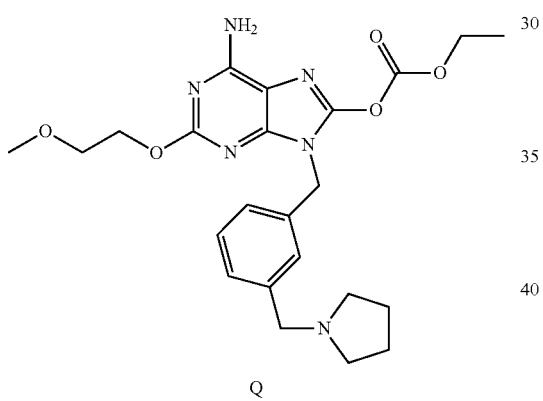

Q

6-Amino-2-(2-methoxy-ethoxy)-9-(3-pyrrolidin-1-ylmethyl-benzyl)-9H-purin-8-ol (Example A) (60 mg, 0.15 mmol) was dissolved in dichloromethane (2 mL). N,N-diisopropylethylamine (0.1 mL) was added and the mixture was cooled to 0° C. Ethylchloroformate (0.04 mL, 0.42 mmol) was added. After stirring for 30 minutes, the reaction was quenched with water and concentrated under vacuum. Purification by preparative reverse phase HPLC (5-45% acetonitrile/40 mM aqueous HCl) gave 9-(3-(pyrrolidin-1-ylmethyl)benzyl)-6-amino-2-(2-methoxyethoxy)-9H-purin-8-yl ethyl carbonate (Example Q) (24 mg) as a white glassy solid, HCl salt.

¹H-NMR (DMSO) δ: 9.99 (br, 1H), 7.45-7.32 (m, 4H), 7.08 (br, 2H), 4.89 (s, 2H), 4.37 (q, J=6.9 Hz, 2H), 4.29 (t, J=4.5 Hz, 2H), 4.20 (br, 2H), 3.58 (t, J=4.5 Hz, 2H), 3.26 (s, 3H), 3.15-2.85 (m, 4H), 1.92-1.78 (m, 4H), 1.31 (t, J=6.9 Hz, 3H). MS: 471 (MH⁺).

Examples R, S, T, U, and V were prepared using procedures similar to those used to prepare Example Q except that ethyl chloroformate was replaced with isopropyl chloroformate and the appropriate starting material was utilized for each of these examples.

Example R

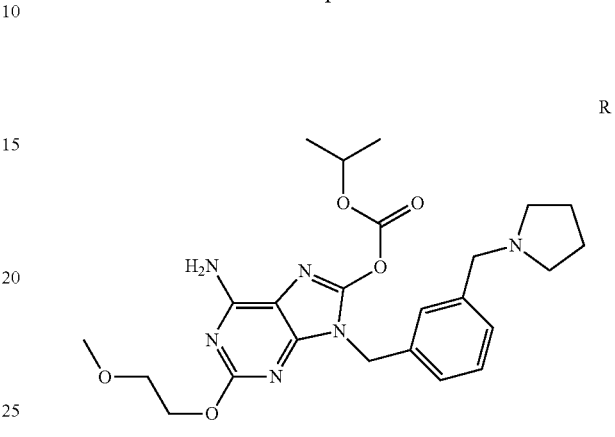

R 9-(3-(pyrrolidin-1-ylmethyl)benzyl)-6-amino-2-(2-methoxyethoxy)-9H-purin-8-yl isopropyl carbonate prepared from Example A.

¹H-NMR (DMSO) δ: 10.65 (br, 1H), 7.55-7.37 (m, 4H), 7.10 (br, 2H), 5.11 (sept, J=6.3 Hz, 1H), 4.89 (s, 2H), 4.33-4.25 (m, 4H), 3.58 (t, J=4.5 Hz, 2H), 3.36-3.26 (m, 2H), 3.26 (s, 3H), 3.08-2.95 (m, 2H), 2.05-1.80 (m, 4H), 1.33 (d, J=6.3 Hz, 6H). MS: 485 (MH⁺).

Example S

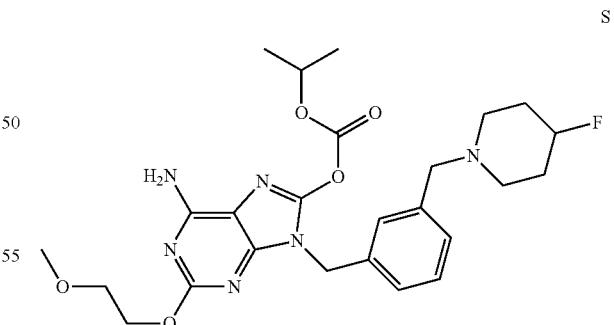

S 9-(3-((4-fluoropiperidin-1-yl)methyl)benzyl)-6-amino-2-(2-methoxyethoxy)-9H-purin-8-yl isopropyl carbonate prepared from Example K.

¹H-NMR (DMSO) δ: 10.95 (br, 1H), 7.59-7.38 (m, 4H), 7.10 (br, 2H), 5.10 (sept, J=6.3 Hz, 1H), 4.89 (s, 2H), 4.33-

4.23 (m, 4H), 3.58 (t, J=4.5 Hz, 2H), 3.36-2.87 (m, 5H), 3.26 (s, 3H), 2.25-1.95 (m, 4H), 1.33 (d, J=6.3 Hz, 6H). MS: 517 (MH+).

Example T

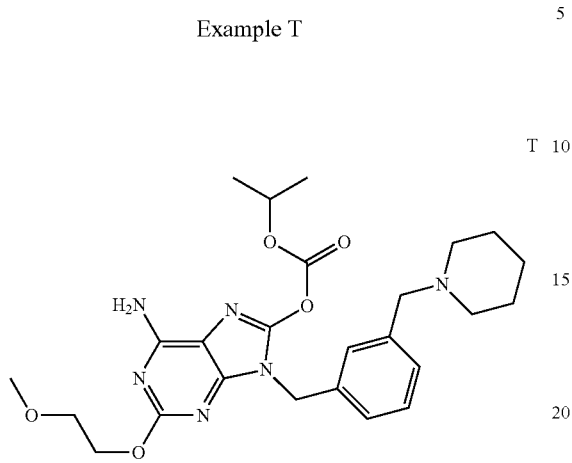

9-(3-(piperidin-1-ylmethyl)benzyl)-6-amino-2-(2-methoxyethoxy)-9H-purin-8-yl isopropyl carbonate prepared from Example J.

$^1$H NMR (CD$_3$OD) δ: 1.43 (d, 6H, J=6 Hz), 1.72-1.97 (m, 6H), 2.95 (t, 4H, J=9.3 Hz), 3.38 (s, 3H), 3.75 (t, 2H, J=4.5, 9 Hz), 4.28 (s, 2H), 4.62 (t, 2H, J=4.5, 9 Hz), 5.11 (s, 2H), 5.21-5.31 (m, 1H), 7.48 (d, 2H, J=4.2 Hz), 7.56 (d, 1H, J=3.6 Hz), 7.66 (s, 1H). LCMS: m/z for C$_{25}$H$_{34}$N$_6$O$_5$$^+$+H observed 499.2 at 2.31 minutes of a 3.5 minute run, gradient 5-95% CH$_3$CN in H$_2$O.

Example U 9-(3-((4-methylpiperazin-1-yl)methyl)benzyl)-6-amino-2-(2-methoxyethoxy)-9H-purin-8-yl isopropyl carbonate prepared from Example C.

$^1$H NMR (CD$_3$OD) δ: 1.43 (d, 6H, J=6 Hz), 3.0 (s, 4H), 3.39 (s, 3H), 3.64 (s, 2H), 3.77 (t, 2H, J=4.5 Hz), 4.49 (s, 2H), 4.63 (t, 2H, J=4.5 Hz), 5.11 (s, 2H), 5.23-5.31 (m, 1H), 7.46-7.62 (m, 3H), 7.72 (s, 1H). LCMS: m/z for C$_{25}$H$_{35}$N$_7$O$_5$$^+$+H observed 514.2 at 2.09 minutes of a 3.5 minute run, gradient 5-95% CH$_3$CN in H$_2$O.

Example V

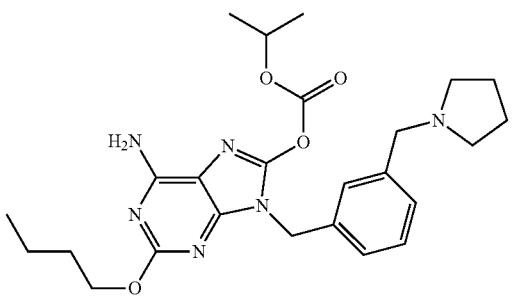

9-(3-(pyrrolidin-1-ylmethyl)benzyl)-6-amino-2-butoxy-9H-purin-8-yl isopropyl carbonate prepared from Example W.

$^1$H NMR (DMSO) δ: 0.89 (t, 3H, J=7.2 Hz), 3.17 (d, 6H), 1.29-42 (m, 2H), 1.62 (q, 2H, J=7.5), 1.79-2.02 (m, 4H), 2.91-3.08 (m, 2H), 3.21-3.36 (m, 2H), 4.17 (t, 2H, J=6.6), 4.29 (d, 2H, J=6), 4.89 (s, 2H), 5.06-5.15 (m, 1H), 7.38-7.57 (m, 4H), 10.95 (s, 1H). LCMS: m/z for C$_{25}$H$_{34}$N$_6$O$_4$$^+$+H observed 483.2 at 2.64 minutes of a 3.5 minute run, gradient 5-95% CH$_3$CN in H$_2$O.

Synthesis of Example W

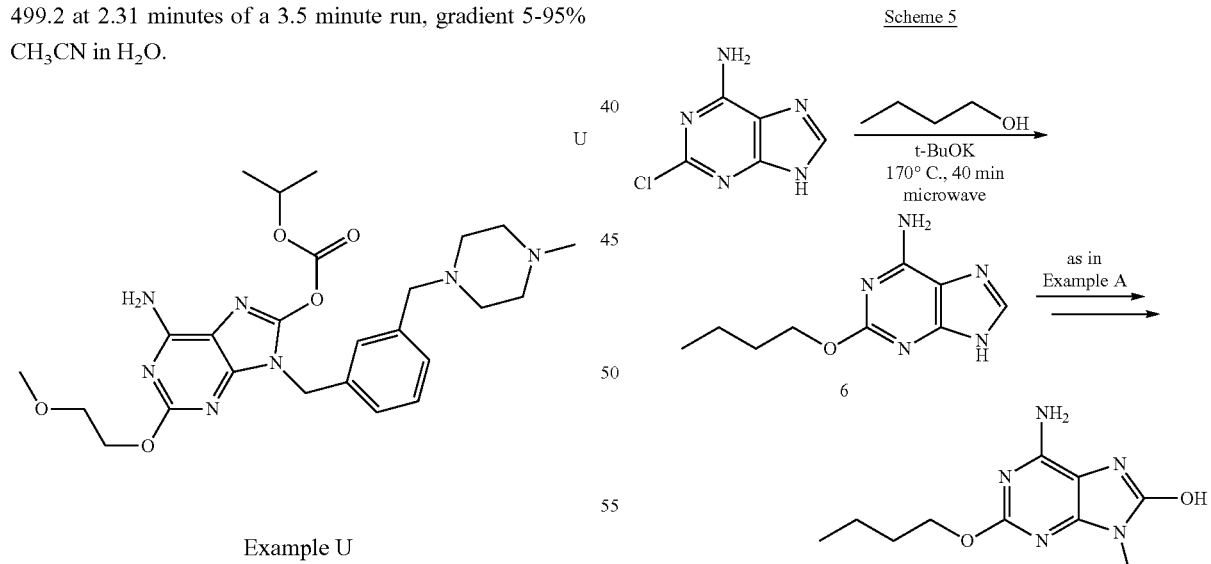

Compound 6

2-chloroadenine (1.53 g, 9.03 mmol) was divided among three microwave vials (10-20 mL), each containing 1-butanol (10 mL) and t-BuOK (5 mL, 1M in THF). Each vial was heated to 170° C. for 40 minutes. The three reaction mixtures were combined, the solvent was removed by rotary evaporation and the product was purified on flash column eluting 10% methanol in ethylacetate. Evaporation of solvent gave 1.33 g (70%) of 2-butoxy-9H-purin-6-amine (6) as an off white solid. $^1$H NMR (DMSO) δ: 0.919 (t, 3H), 1.39 (m, 2H), 1.62 (m, 2H), 4.09 (t, 2H), 6.00 (s, 2H), 7.44 (s, 1H). LCMS: m/z for $C_9H_{13}N_5O^+$+H observed 208.1 at 1.34 minutes of a 3.5 minute run, gradient 5-95% $CH_3CN$ in $H_2O$.

Example W was prepared from Compound 6 using procedures similar to those used to prepare Example A.

$^1$H NMR (DMSO) δ: 0.89 (t, 3H, J=7.2 Hz), 1.29-1.42 (m, 2H), 1.60 (q, 2H, J=7.2), 1.77-2.04 (m, 4H), 2.97-3.10 (m, 2H), 3.26-3.37 (m, 2H), 4.12 (t, 2H, J=7), 4.30 (d, 2H, J=6), 4.89 (s, 2H), 7.30-7.50 (m, 4H), 10.26 (s, 1H). LCMS: m/z for $C_{21}H_{28}N_6O_2^+$+H observed 397.2 at 2.50 minutes of a 3.5 minute run, gradient 5-95% $CH_3CN$ in $H_2O$.

Synthesis of Example X

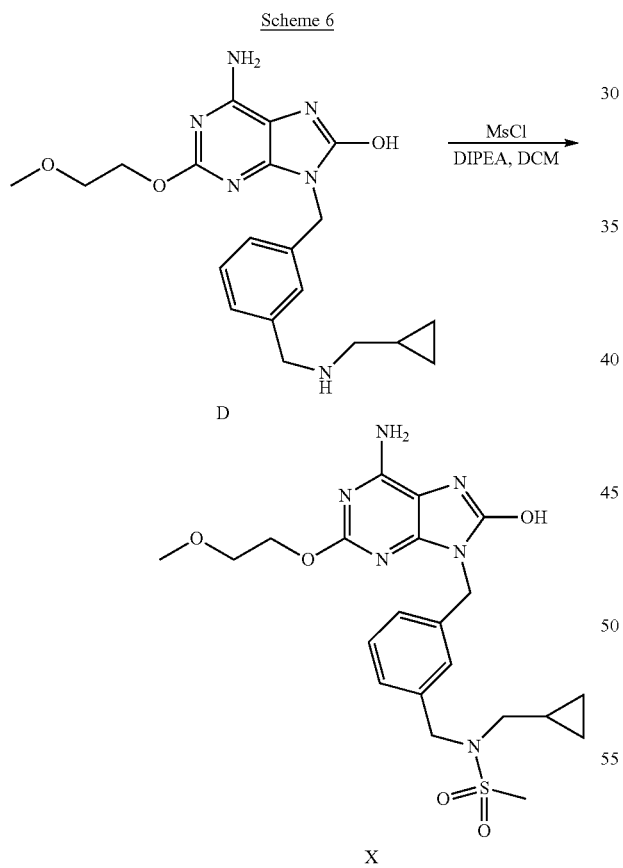

Example X

Example D (40 mg, 0.100 mmol) was dissolved in dichloromethane (2 mL) and cooled to 0° C. Diisopropylethylamine (0.1 mL) and then methanesulfonyl chloride (0.012 mL, 0.154 mmol) was added sequentially. After stirring for 1 hour at 0° C., the reaction mixture was quenched with water (1 mL) and evaporated to dryness. Purification by reverse phase preparative HPLC (5-60% acetonitrile/40 mM aqueous HCl) gave Example X (23 mg).

$^1$H NMR (DMSO) δ: 9.96 (s, 1H), 7.34-7.18 (m, 4H), 6.45 (br, 2H), 4.85 (s, 2H), 4.37 (s, 2H), 4.24 (t, J=4.5 Hz, 2H), 3.57 (t, J=4.5 Hz, 2H), 3.26 (s, 3H), 2.94 (s, 3H), 2.91 (d, J=6.9 Hz, 2H), 0.88-0.78 (m, 1H), 0.35-0.29 (m, 2H), 0.04-0.00 (m, 2H). MS: 477 (MH$^+$).

Synthesis of Example Y

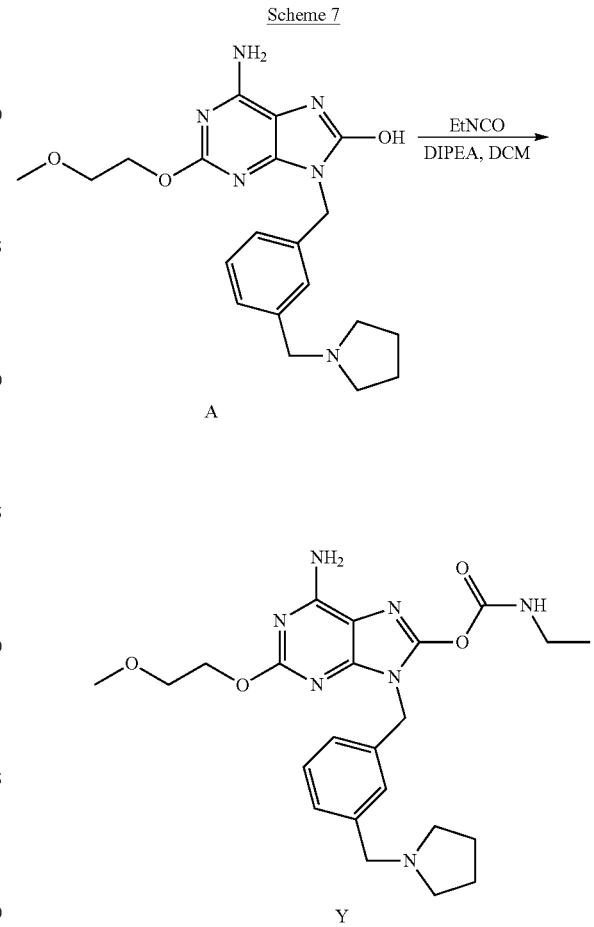

Example Y

Example A (30 mg, 0.075 mmol) was dissolved in dichloromethane (2 mL). Diisopropylethylamine (0.1 mL) and then ethyl isocyanate (0.05 mL) was added. After stirring at ambient temperature overnight, the reaction mixture was evaporated to dryness under vacuum. Purification by reverse phase preparative HPLC (5-60% acetonitrile/40 mM aqueous HCl) gave Example Y (23 mg) as a white solid as the HCl salt.

$^1$H NMR (DMSO) δ: 10.96 (br, 1H), 8.87 (t, J=5.7 Hz, 1H), 7.57-7.36 (m, 4H), 4.95 (s, 2H), 4.32-4.25 (m, 4H), 3.58 (t,

J=4.5 Hz, 2H), 3.25 (s, 3H), 3.36-3.25 (m, 4H), 3.05-2.92 (m, 2H), 2.02-1.80 (m, 4H), 1.13 (t, J=7.2 Hz, 3H). MS: 470 (MH$^+$).

Synthesis of Example Z

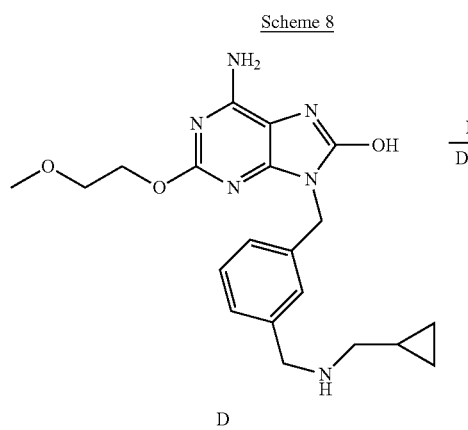

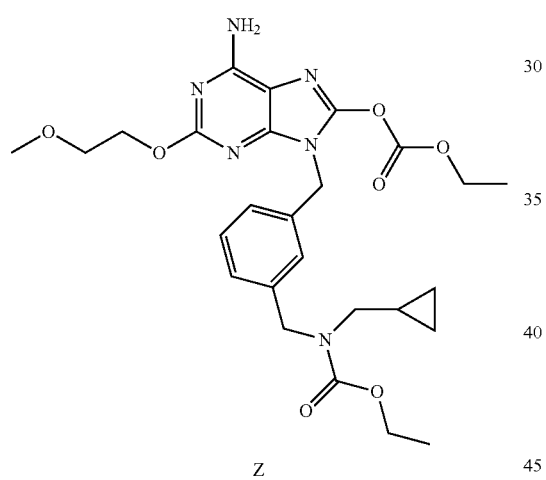

Example Z

Example D (40 mg, 0.10 mmol) was dissolved in dichloromethane (2 mL).

N,N-diisopropylethylamine (0.1 mL) was added and the mixture was cooled to 0° C. Ethylchloroformate (0.021 mL, 0.22 mmol) was added. After stirring for 30 minutes, the reaction was quenched with water and concentrated under vacuum. Purification by preparative reverse phase HPLC (5-60% acetonitrile/40 mM aqueous HCl) gave Example Z (17 mg) as a white solid.

$^1$H-NMR (DMSO) δ: 7.32-7.11 (m, 4H), 7.06 (br, 2H), 4.85 (s, 2H), 4.45 (s, 2H), 4.36 (q, J=7.5 Hz, 2H), 4.28 (t, J=4.5 Hz, 2H), 4.02 (br, 2H), 3.58 (t, J=4.5 Hz, 2H), 3.26 (s, 3H), 3.06-2.97 (m, 2H), 1.30 (t, J=6.9 Hz, 3H), 1.22-1.02 (m, 3H), 0.93-0.81 (m, 1H), 0.38-0.29 (m, 2H), 0.12-0.05 (m, 2H). MS: 543 (MH$^+$)

Synthesis of Example AA and Example AB

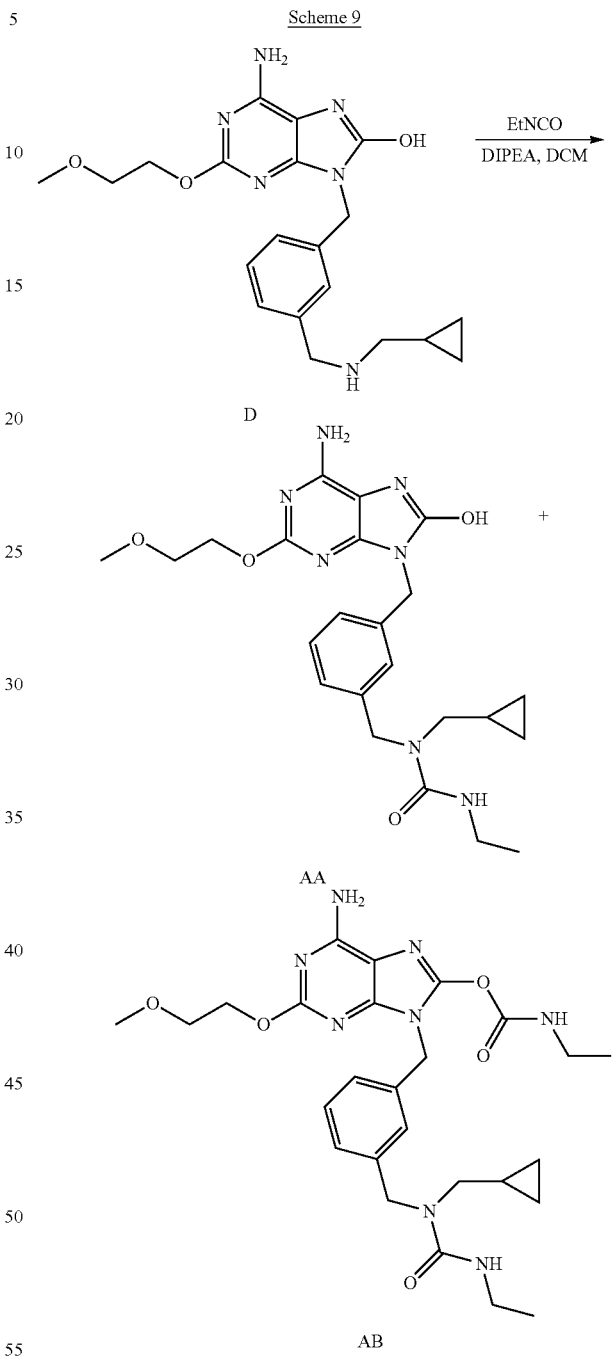

Examples AA and AB

Example D (40 mg, 0.10 mmol) was dissolved in dichloromethane (2 mL). N,N-diisopropylethylamine (0.1 mL) was added and then ethyl isocyanate (0.05 mL). After stirring at ambient temperature for 30 minutes, the reaction mixture was evaporated to dryness under vacuum. Purification by reverse phase preparative HPLC (5-60% acetonitrile/40 mM aqueous HCl) gave Example AA (4 mg) and Example AB (6.5 mg) as white solids.

Example AA

¹H NMR (DMSO) δ: 9.93 (s, 1H), 7.30-7.09 (m, 4H), 6.44 (br, 2H), 6.30 (m, 1H), 4.82 (s, 2H), 4.46 (s, 2H), 4.24 (t, J=4.5 Hz, 2H), 3.57 (t, J=4.5 Hz, 2H), 3.26 (s, 3H), 3.10-2.94 (m, 4H), 0.96 (t, J=6.9 Hz, 3H), 0.93-0.81 (m, 1H), 0.34-0.25 (m, 2H), 0.08-0.01 (m, 2H). MS: 470 (MH⁺).

Example AB

¹H NMR (DMSO) δ: 8.88 (m, 1H), 7.30-7.05 (m, 4H), 6.29 (m, 1H), 4.90 (s, 2H), 4.46 (s, 2H), 4.29 (t, J=4.5 Hz, 2H), 3.59 (t, J=4.5 Hz, 2H), 3.30 (m, 2H), 3.26 (s, 3H), 3.08-2.94 (m, 4H), 1.13 (t, J=6.9 Hz, 3H), 0.95 (t, J=6.9 Hz, 3H), 0.90-0.80 (m, 1H), 0.34-0.25 (m, 2H), 0.08-0.01 (m, 2H). MS: 541 (MH⁺).

Synthesis of AC

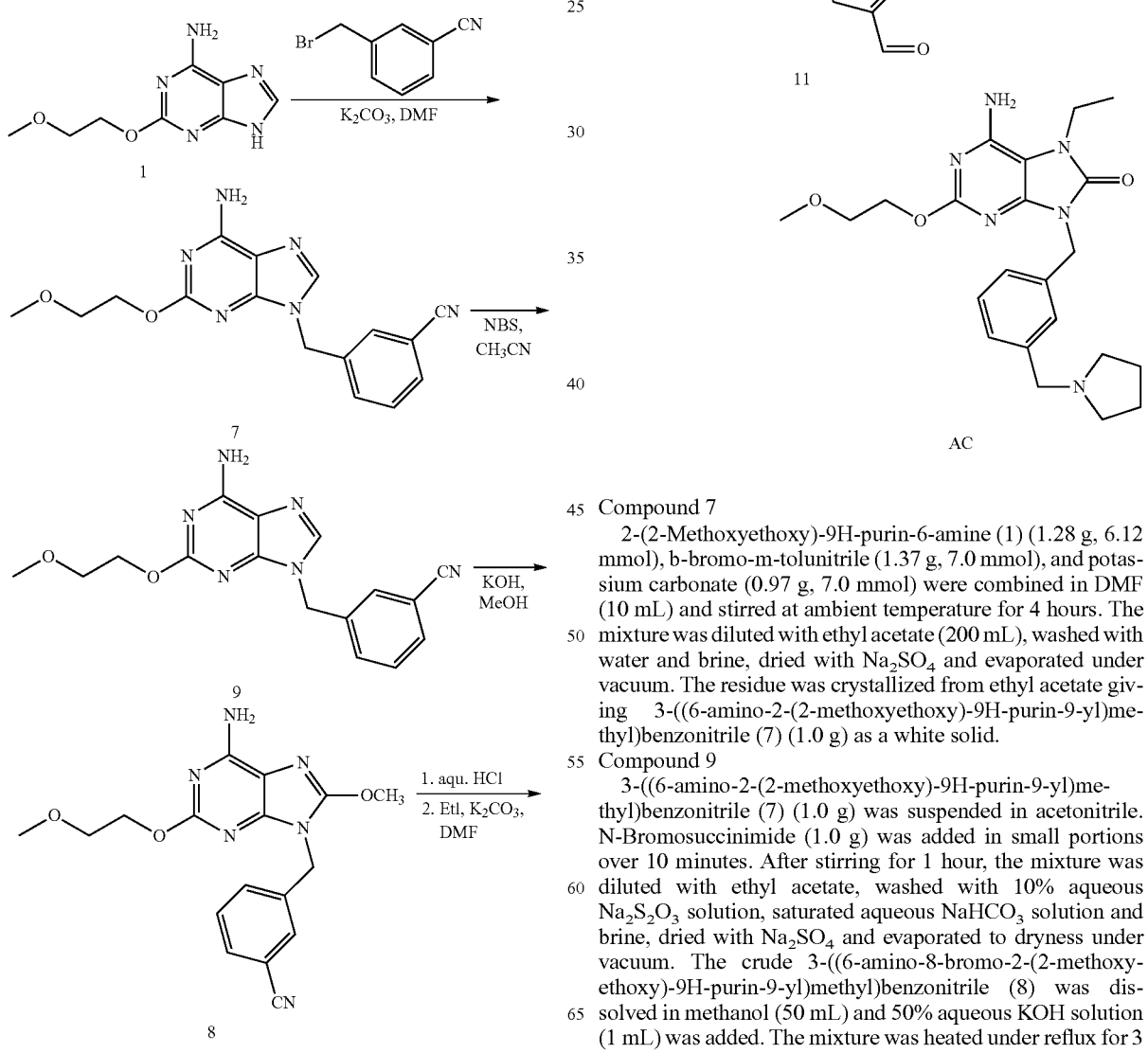

Compound 7

2-(2-Methoxyethoxy)-9H-purin-6-amine (1) (1.28 g, 6.12 mmol), b-bromo-m-tolunitrile (1.37 g, 7.0 mmol), and potassium carbonate (0.97 g, 7.0 mmol) were combined in DMF (10 mL) and stirred at ambient temperature for 4 hours. The mixture was diluted with ethyl acetate (200 mL), washed with water and brine, dried with Na₂SO₄ and evaporated under vacuum. The residue was crystallized from ethyl acetate giving 3-((6-amino-2-(2-methoxyethoxy)-9H-purin-9-yl)methyl)benzonitrile (7) (1.0 g) as a white solid.

Compound 9

3-((6-amino-2-(2-methoxyethoxy)-9H-purin-9-yl)methyl)benzonitrile (7) (1.0 g) was suspended in acetonitrile. N-Bromosuccinimide (1.0 g) was added in small portions over 10 minutes. After stirring for 1 hour, the mixture was diluted with ethyl acetate, washed with 10% aqueous Na₂S₂O₃ solution, saturated aqueous NaHCO₃ solution and brine, dried with Na₂SO₄ and evaporated to dryness under vacuum. The crude 3-((6-amino-8-bromo-2-(2-methoxyethoxy)-9H-purin-9-yl)methyl)benzonitrile (8) was dissolved in methanol (50 mL) and 50% aqueous KOH solution (1 mL) was added. The mixture was heated under reflux for 3 hours and then concentrated under vacuum. The product was extracted with ethyl acetate, the combined organic layers were washed with water and brine, dried with Na₂SO₄ and evaporated under vacuum. Purification by flash chromatography on silica gel (eluent: 0-10% MeOH in ethyl acetate) gave 3-((6-amino-8-methoxy-2-(2-methoxyethoxy)-9H-purin-9-yl)methyl)benzonitrile (9) (0.45 g) as a pinkish solid.

Compound 10

3-((6-Amino-8-methoxy-2-(2-methoxyethoxy)-9H-purin-9-yl)methyl)benzonitrile (9) (50 mg) was dissolved in acetonitrile (2 mL). A 6N aqueous HCl solution (2 mL) was added and the mixture was stirred at ambient temperature overnight. After evaporation to dryness, the residue was dissolved in DMF (1 mL). Potassium carbonate (100 mg) and ethyl iodide (0.02 mL) were added and the mixture was stirred at ambient temperature for 5 hours. After dilution with water (20 mL) the product was extracted with dichloromethane. The combined organic layers were washed with water and brine, dried with Na₂SO₄ and evaporated under vacuum. Purification by flash chromatography on silica gel (eluent: 0-10% MeOH in ethyl acetate) gave 3-((6-amino-7-ethyl-2-(2-methoxyethoxy)-8-oxo-7,8-dihydropurin-9-yl)methyl)benzonitrile (10) (35 mg) as a colorless glass.

Example AC 3-((6-Amino-7-ethyl-2-(2-methoxyethoxy)-8-oxo-7,8-dihydropurin-9-yl)methyl)benzonitrile (35 mg) was dissolved in dichloromethane (2 mL) and cooled to 0° C. 1M DIBAL solution in toluene (0.5 mL) was added. After stirring for 1 hour, the reaction was quenched with water and a saturated solution of Rochelle salt was added. After vigorous stirring for 30 minutes, the mixture was extracted with dichloromethane. The combined organic layers were washed with water and brine, dried with Na₂SO₄ and evaporated under vacuum. The crude product (11) was dissolved in methanol (1 mL) and acetic acid (0.5 mL). Pyrrolidine (0.1 mL) was added followed by sodium triacetoxy borohydride (100 mg). The mixture was stirred for 1 hour at ambient temperature and then evaporated to dryness. The residue was dissolved in aqueous HCl/acetonitrile and purified by preparative reverse phase HPLC (5-60% acetonitrile/40 mM aqueous HCl) which gave Example AC (9 mg) as the HCl salt as a colorless glass.

¹H NMR (DMSO) δ: 10.66 (br, 1H), 7.54-7.29 (m, 4H), 6.74 (br, 2H), 4.92 (s, 2H), 4.31-4.25 (m, 4H), 3.97 (m, 2H, under the water peak), 3.58 (t, J=4.5 Hz, 2H), 3.26 (s, 3H), 3.35-3.25 (m, 2H), 3.07-2.95 (m, 2H), 2.05-1.80 (m, 4H), 1.12 (t, J=6.9 Hz, 3H). MS: 427 (MH⁺).

Synthesis of Example AD

Scheme 11

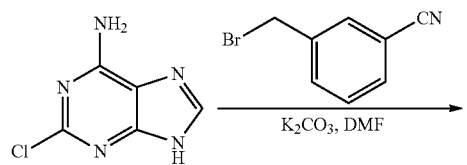

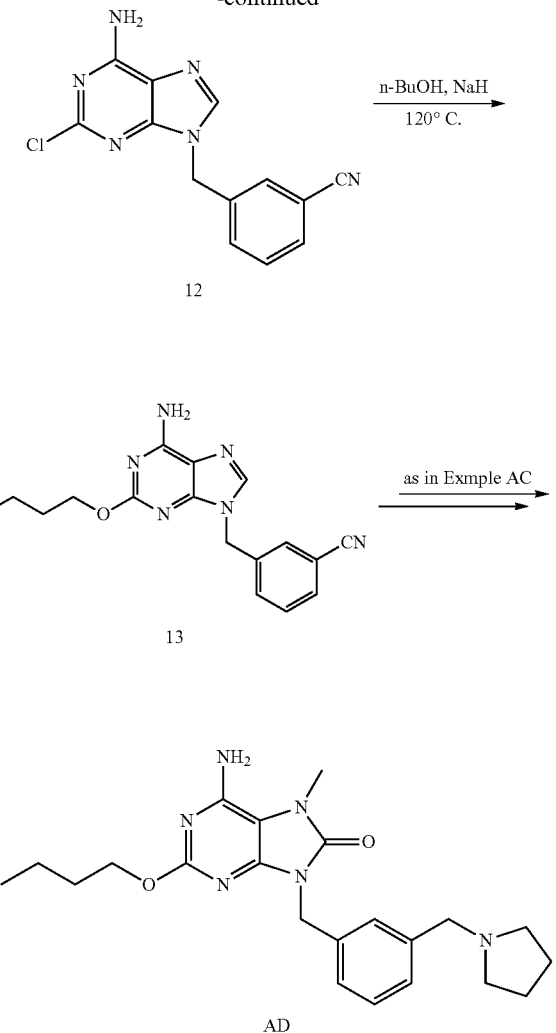

Compound 12

To a suspension of 2-chloroadenine (1.7 g, 10.18 mmol) in DMF (10 mL) was added K₂CO₃ (1.4 g, 10.18 mmol), 2-bromomethylbenzonitrile (2 g, 10.18 mmol). The reaction was reacted at 80° C. After the reaction was complete, the reaction mixture was diluted with water, and then the precipitate was collected. The solid was washed by water, then ether ester. The product (12) was dried under high vacuum. MS: 285 (MH⁺).

Compound 13

To a flask with n-BuOH (10 ml), was added NaH (60%, 840 mg, 21 mmol) at room temperature. The reaction mixture was stirred at ambient temperature for 5 min. Then compound 12 (2.4 g, 8.4 mmol) was added. The mixture was allowed to react at 120° C. for about half an hour. Then the reaction mixture was cooled, washed with saturated NH₄Cl solution and extracted with DCM. The organic layer was dried over Na₂SO₄ and filtered. The filtrate was concentrated down, and the residue (13) was purified by silica gel column, using DCM/MeOH as solvent. ¹H NMR (d₆-DMSO) δ: 0.90 (t, 3H), 1.33-1.41 (m, 2H), 1.58-1.67 (m, 2H), 4.19 (t, 2H), 5.32 (s, 2H), 7.22 (s, 2H), 7.52-7.84 (m, 4H), 8.06 (s, 1H); 323 (MH⁺).

Example AD was prepared from Compound 13 using procedures similar to those used to prepare Example AC except that Compound 10 was replaced with Compound 13.

¹H NMR (CD₃OD) δ: 0.99 (t, 3H), 1.46-1.54 (m, 2H), 1.76-1.1.83 (m, 2H), 2.01-2.11 (m, 2H), 2.15-2.17 (m, 2H), 3.16-3.18 (m, 2H), 3.45-3.47 (m, 2H), 3.61 (s, 3H), 4.36 (s, 2H), 4.54 (t, 2H), 5.14 (s, 2H), 7.48-7.60 (m, 4H); MS: 411 (MH⁺).

Examples AE, AF, AG and AH were prepared using procedures similar to those used to prepare Example AD except that the appropriate iodide was used during the 7-N alkylation step to make the corresponding compounds.

Example AE

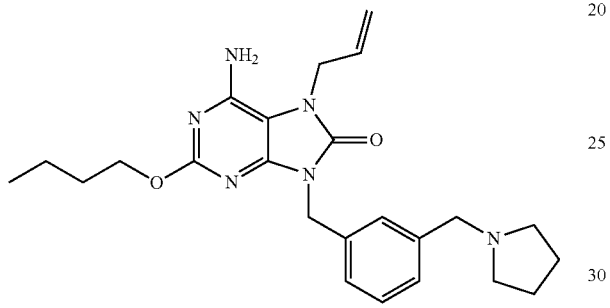

AE

¹H NMR (CD₃OD) δ: 0.99 (t, 3H), 1.47-1.54 (m, 2H), 1.77-1.86 (m, 2H), 2.02-2.07 (m, 2H), 2.10-2.16 (m, 2H), 3.15-3.19 (m, 2H), 3.44-3.47 (m, 2H), 4.37 (s, 2H), 4.56 (t, 2H), 4.70 (s, 2H), 5.08-5.26 (m, 4H), 5.98-6.07 (m, 1H), 7.44-7.63 (m, 4H); MS: 437 (MH⁺).

Example AF

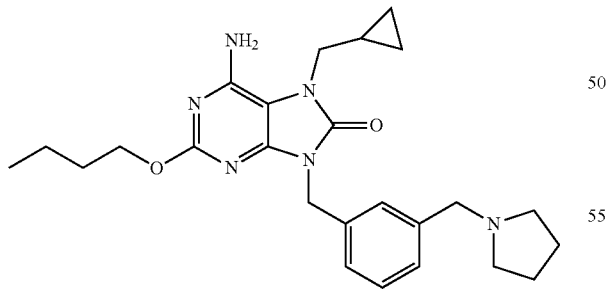

AF

¹H NMR (CD₃OD) δ: 0.41-0.42 (m, 2H), 0.53-0.56 (m, 2H), 0.99 (t, 3H), 1.53-1.57 (m, 1H), 1.47-1.55 (m, 2H), 1.78-1.84 (m, 2H), 2.01-2.04 (m, 2H), 2.14-2.17 (m, 2H), 3.15-3.19 (m, 2H), 3.44-3.47 (m, 2H), 3.97 (d, 2H), 4.38 (s, 2H), 4.55 (t, 2H), 5.16 (s, 2H), 7.50-7.61 (m, 4H); MS: 451 (MH⁺).

Example AG

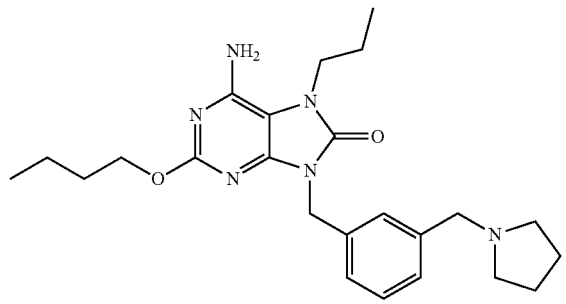

AG

¹H (CD₃OD) δ: 0.90-1.01 (m, 6H), 1.46-1.54 (m, 2H), 1.69-1.84 (m, 4H), 2.00-2.04 (m, 2H), 2.15-2.17 (m, 2H), 3.16-3.19 (m, 2H), 3.44-3.47 (m, 2H), 4.04 (m, 2H), 4.37 (s, 2H), 4.56 (t, 2H), 5.16 (s, 2H), 7.46-7.61 (m, 2H); MS: 439 (MH⁺).

Example AH

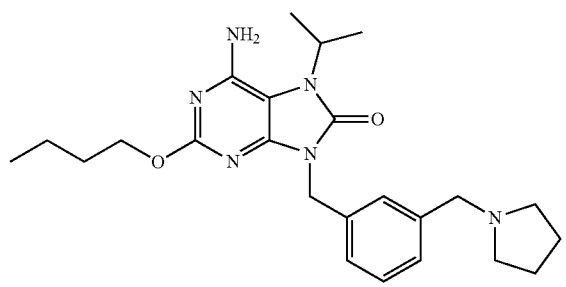

AH

¹H NMR (CD₃OD) δ: 0.99 (t, 3H), 1.46-1.54 (m, 2H), 1.59 (d, 6H), 1.77-1.82 (m, 2H), 2.00-2.04 (m, 2H), 2.15-2.18 (m, 2H), 3.16-3.20 (m, 2H), 3.45-3.49 (m, 2H), 4.38 (s, 2H), 4.55 (t, 3H), 5.11 (s, 2H), 7.48-7.60 (m, 4H); MS: 439 (MH⁺).

Synthesis of Example AI

-continued

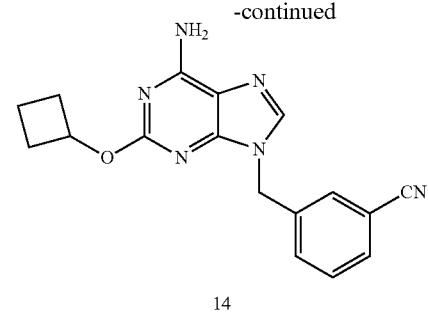

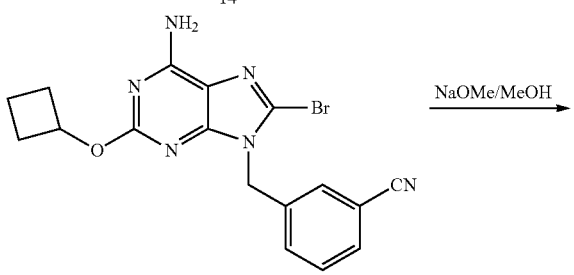

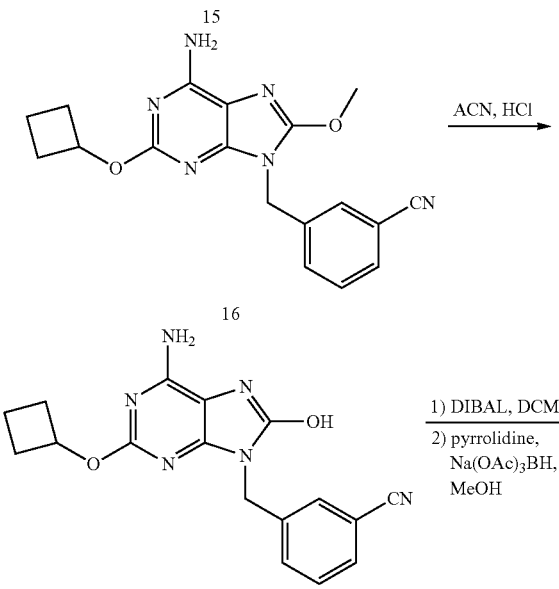

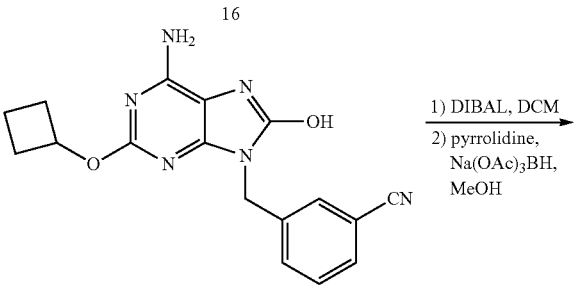

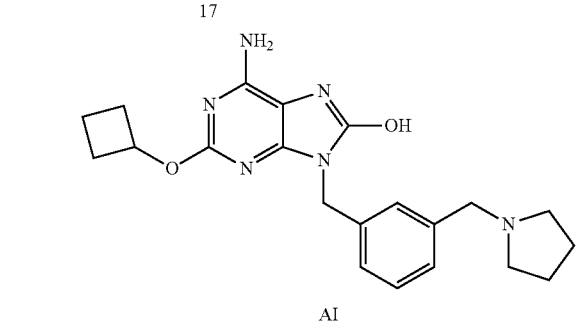

Compound 14 was prepared using the procedures similar to those used to prepare Compound 13 except that cyclobutanol was used instead of n-BuOH. $^1$H NMR (CDCl$_3$) δ: 1.61-1.95 (m, 2H), 2.14-2.44 (m, 4H), 5.13-5.18 (m, 1H), 5.30 (s, 2H), 5.94 (s, 2H), 7.44-7.64 (m, 5H); MS: 321 (MH$^+$).

Example AI was prepared using the procedures shown in Scheme 12, and similar to those used to prepare Example AC. The spectral data of the intermediates and Example AC are shown below.

Compound 15
$^1$H NMR (CDCl$_3$) δ: 1.62-1.88 (m, 2H), 2.11-2.45 (m, 4H), 5.14-5.16 (m, 1H), 5.30 (s, 2H), 6.23 (s, 2H), 7.44-7.65 (m, 4H); MS: 399 (MH$^+$).

Compounds 16
$^1$H NMR (CDCl$_3$) δ: 1.52-1.77 (m, 2H), 1.96-2.17 (m, 2H), 2.29-2.38 (m, 2H), 4.02 (s, 3H), 5.01-5.08 (m, 3H), 5.91 (s, 2H), 7.32-7.56 (m, 4H); MS: 351 (MH$^+$).

Compound 17
$^1$H NMR (CDCl$_3$) δ: 1.68-1.88 (m, 2H), 3.20-3.37 (m, 4H), 5.00-5.02 (m, 2H), 5.19-5.20 (m, 1H), 7.45-7.68 (m, 4H); MS: 337 (MH$^+$).

Example AI $^1$H NMR (CD$_3$OD) δ: 1.73-2.28 (m, 8H), 2.44-2.48 (m, 2H), 3.15-3.20 (m, 2H), 4.44-4.48 (m, 2H), 4.37 (s, 2H), 5.10 (s, 2H), 5.25-5.34 (m, 1H), 7.49-7.59 (m, 4H); MS: 395 (MH$^+$).

Synthesis of Example AJ

Scheme 13

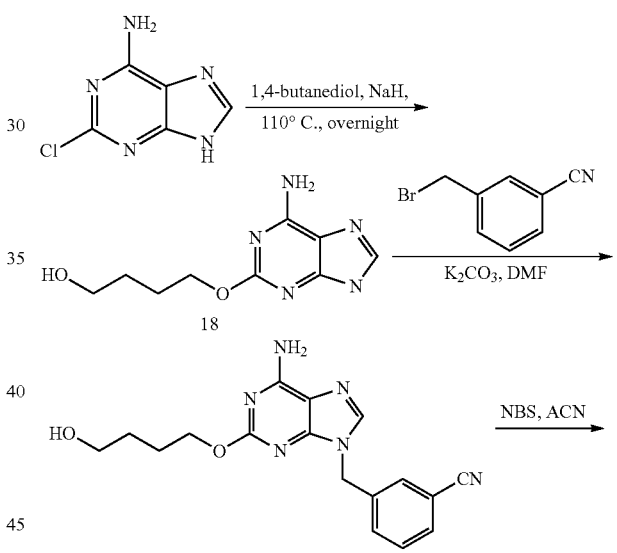

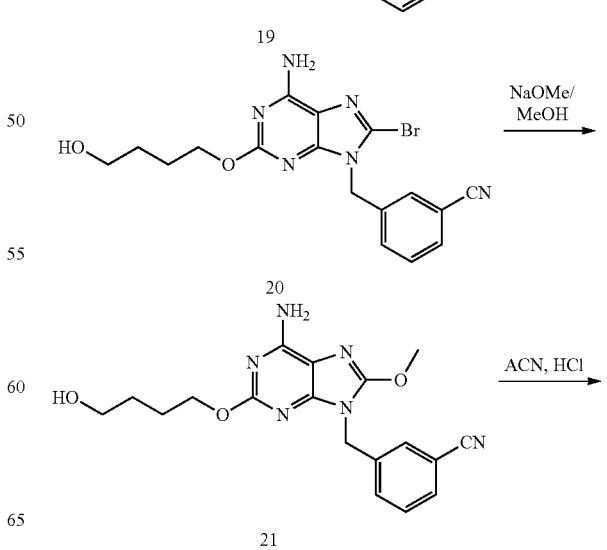

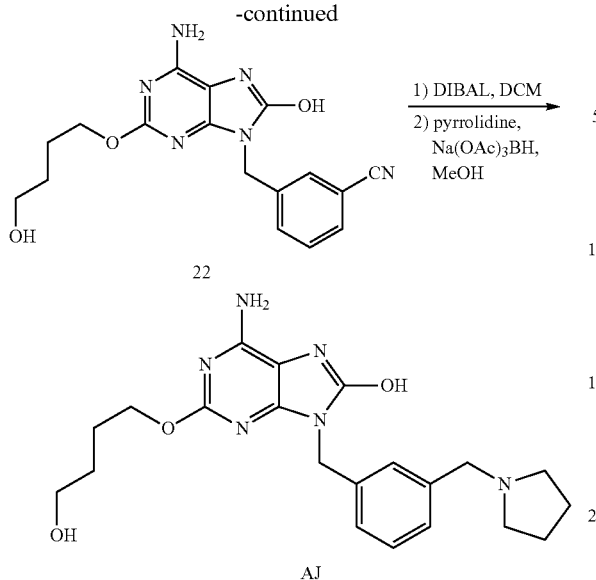

Example AJ was prepared using the procedures shown in scheme 13, and similar to those used to prepare Example AC. The spectral data of the intermediates and Example AJ are listed below.

Compound 18
$^1$H NMR (DMSO) δ: 1.47-1.56 (m, 2H), 1.64-1.74 (m, 2H), 3.33-3.43 (m, 2H), 4.16 (t, 2H), 7.05 (s, 2H), 7.87 (s, 1H), 12.55 (bs, 1H); MS: 224 (MH$^+$).

Compound 19
$^1$H NMR (CDCl$_3$) δ: 1.65-1.74 (m, 2H), 1.81-1.87 (m, 2H), 3.69 (t, 2H), 5.27 (s, 2H), 6.52 (s, 2H), 7.39-7.68 (m, 5H); MS: 339 (MH$^+$).

Compound 20
$^1$H NMR (CDCl$_3$) δ: 1.70-1.76 (m, 2H), 1.82-1.87 (m, 2H), 3.69 (t, 2H), 4.32 (t, 2H), 5.28 (s, 2H), 6.57 (s, 2H), 7.39-7.63 (m, 4H); MS: 419 (MH$^+$).

Compound 21
$^1$H NMR (CDCl$_3$) δ: 1.70-1.74 (m, 2H), 1.81-1.87 (m, 2H), 3.69 (t, 2H), 4.07 (s, 3H), 4.29 (t, 2H), 5.08 (s, 2H), 5.81 (s, 2H), 7.37-7.61 (m, 4H); MS: 369 (MH$^+$).

Compound 22
$^1$H NMR (CD$_3$OD) δ: 1.69-1.70 (m. 2H), 1.87-1.91 (m, 2H), 3.63 (t, 2H), 4.56 (t, 2H), 5.11 (s, 2H), 7.56-7.82 (4H); MS: 355 (MH$^+$).

Example AJ $^1$H NMR (CD$_3$OD) δ: 1.66-1.72 (m, 2H), 1.87-1.93 (m, 2H), 2.01-2.04 (m, 2H), 2.15-2.18 (m, 2H), 3.15-3.19 (m, 2H), 3.45-3.49 (m, 2H), 3.62 (t, 2H), 4.38 (t, 2H), 4.58 (t, 2H), 5.12 (s, 2H), 7.47-7.61 (m, 4H); MS: 413 (MH$^+$).

Synthesis of Example AK and Example AL

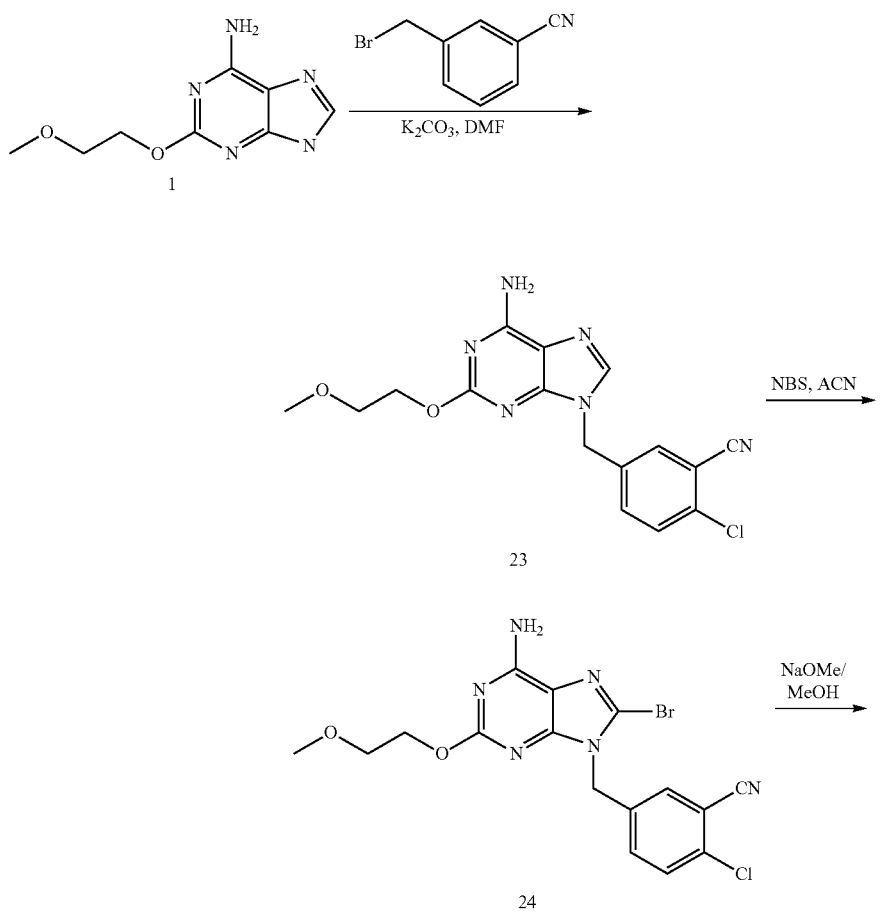

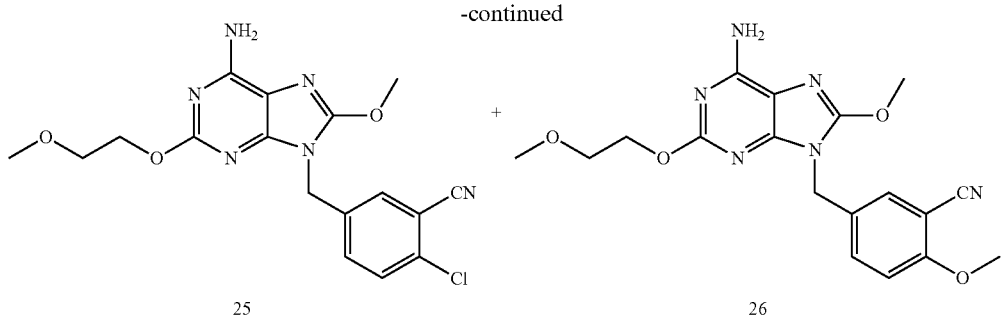

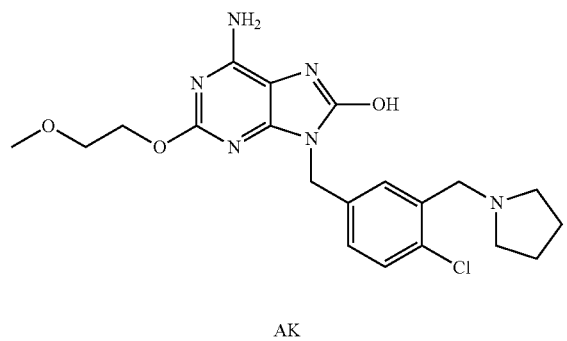

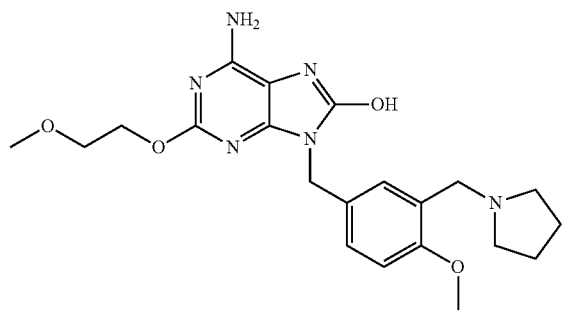

Example AK and Example AL were prepared using the procedures shown in Scheme 14, and similar to those used to prepare Example AC. The bromide (23) used in the first step was made by treating the corresponding benzenemethyl compound with NBS in acetonitrile at room temperature or at 40° C. The spectral data of intermediates and Example AK and Example AL are listed below.

Compound 23

$^1$H NMR (CDCl$_3$) δ: 3.43 (s, 3H), 3.75 (t, 2H), 4.47 (s, 2H), 5.28 (s, 2H), 5.85 (s, 2H), 7.47-7.65 (m, 4H); MS: 359 (MH$^+$).

Compound 24

$^1$H NMR (CD$_3$OD) δ: 3.40 (s, 3H), 3.73 (s, 2H), 4.47 (s, 2H), 5.38 (s, 2H), 7.58-7.62 (m, 2H), 7.84 (s, 1H); MS: 437 (MH$^+$).

Compound 25

$^1$H NMR (CDCl$_3$) δ: 3.41 (s, 3H), 3.74 (t, 2H), 4.09 (s, 3H), 4.44 (t, 2H), 5.06 (s, 2H), 5.48 (s, 2H), 7.42-7.61 (m, 3H); MS: 389 (MH$^+$).

Compound 26

$^1$H NMR (CDCl$_3$) δ: 3.41 (s, 3H), 3.72-3.76 (m, 2H), 3.89 (s, 3H), 4.09 (s, 3H), 3.42-3.47 (m, 2H), 5.00 (s, 2H), 5.48 (s, 2H), 7.45-7.62 (m, 3H); MS: 385 (MH$^+$).

Example AK $^1$H NMR (CD$_3$OD) δ: 2.02-2.06 (m, 2H), 2.20-2.23 (m, 2H), 3.10-3.16 (m, 2H), 3.40 (s, 3H), 3.54-3.58 (m, 2H), 3.76 (t, 2H), 4.63 (t, 2H), 5.10 (s, 2H), 7.52-7.59 (m, 2H), 7.74 (s, 1H); MS: 433 (MH$^+$).

Example AL $^1$H NMR (CD$_3$OD) δ: 2.01-2.03 (m, 2H), 2.15-2.19 (m, 2H), 3.18-3.23 (m, 2H), 3.41 (s, 3H), 4.44-3.49 (m, 2H), 3.77 (t, 2H), 3.93 (s, 3H), 4.36 (s, 2H), 4.66 (t, 2H), 5.03 (s, 2H), 7.11 (d, 1H), 7.52-7.58 (m, 2H); MS: 429 (MH$^+$).

Synthesis of Example AM

Scheme 15

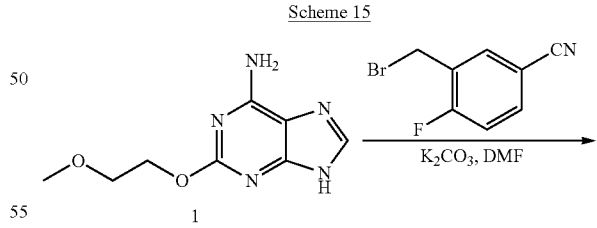

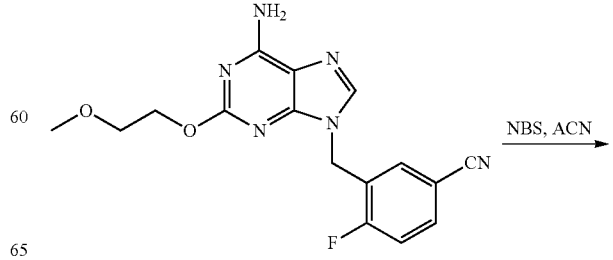

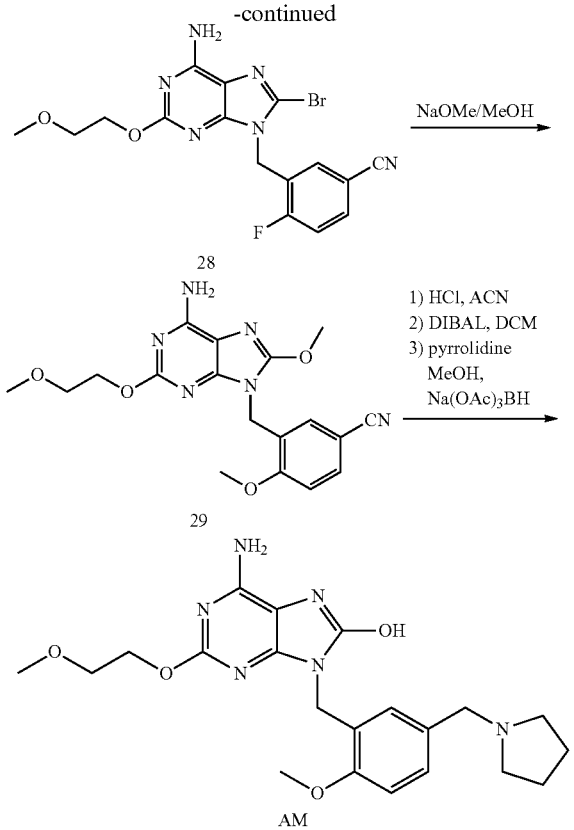

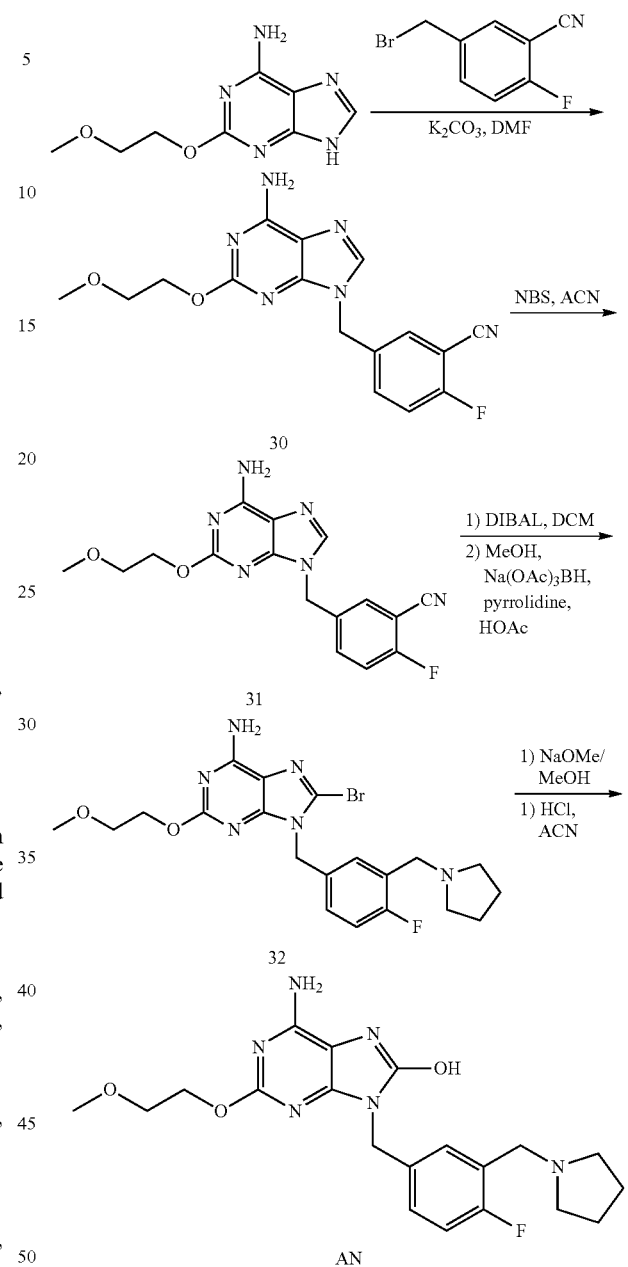

Example AM was prepared using the procedures shown in Scheme 15, and similar to the procedures used to prepare Example AC. The spectral data of the intermediates and Example AM are listed below.

Compound 27

$^1$H NMR (CD$_3$OD) δ: 3.39 (s, 3H), 3.73 (t, 2H), 4.45 (t, 2H), 5.44 (s, 2H), 7.36 (t, 1H), 7.78-7.87 (m, 2H), 8.01 (s, 1H); MS: 343 (MH$^+$).

Compound 28

$^1$H NMR (CD$_3$OD) δ: 3.39 (s, 3H), 3.72 (t, 2H), 4.44 (t, 2H), 5.44 (s, 2H), 7.37 (t, 1H), 7.67-7.79 (m, 2H); MS: 421 (MH$^+$).

Compound 29

$^1$H NMR (CDCl$_3$) δ: 3.40 (s, 3H), 3.73 (t, 2H), 3.92 (s, 3H), 4.11 (s, 3H), 4.46 (t, 2H), 5.12 (s, 2H), 6.94 (d, 1H), 7.14 (s, 1H), 7.60 (dd, 1H); MS: 385 (MH$^+$).

Example AM $^1$H NMR (CD$_3$OD) δ: 1.97-1.99 (m, 2H), 2.13-2.16 (m, 2H), 3.12-3.17 (m, 2H), 3.37 (s, 3H), 3.38-3.44 (m, 2H), 3.72 (t, 2H), 3.89 (s, 3H), 4.27 (s, 2H), 4.56 (t, 2H), 5.08 (s, 2H), 7.09 (d, 1H), 7.33 (s, 1H), 7.45 (dd, 1H); MS: 429 (MH$^+$).

Synthesis of Example AN

Example AN was prepared using the procedures shown in Scheme 16, and similar to those used to prepare Example AC. The spectral data of intermediates and Example AN are listed below.

Compound 30

$^1$H NMR (CD$_3$OD) δ: 3.40 (s, 3H), 3.73 (t, 2H), 4.47 (t, 2H), 5.36 (s, 2H), 7.35 (t, 1H), 7.72-7.86 (m, 2H), 8.03 (s, 1H); MS: 343 (MH$^+$).

Compound 31

$^1$H NMR (CDCl$_3$) δ: 3.44 (s, 3H), 3.77 (t, 2H), 4.53 (s, 2H), 5.30 (s, 2H), 6.11 (bs, 2H), 7.21-7.27 (m, 2H), 7.64-7.68 (m, 2H); MS: 421 (MH$^+$).

Compound 32

$^1$H NMR (CD$_3$OD) δ: 2.00-2.12 (m, 2H), 2.13-2.17 (m, 2H), 3.19-3.22 (m, 2H), 3.40 (s, 3H), 3.42-3.54 (m, 2H), 3.74 (t, 2H), 4.45 (s, 2H), 4.54 (t, 2H), 5.39 (s, 2H), 7.29 (t, 1H), 7.52-7.56 (m, 2H); MS: 479 (MH$^+$).

Example AN $^1$H NMR (CD$_3$OD) δ: 2.01-2.06 (m, 2H), 2.18-2.20 (m, 2H), 3.18-3.24 (m, 2H), 3.40 (s, 3H), 3.51-3.55 (m, 2H), 3.76-3.79 (m, 2H), 4.46 (s, 2H), 4.66-4.69 (m, 2H), 5.10 (s, 2H), 7.27 (t, 1H), 7.61-7.63 (m, 1H), 7.68-7.72 (m, 1H); MS: 417 (MH$^+$).

Example AO was prepared using procedures similar to those used to prepare Example AM (Scheme 15), except that in the first step, 1-bromo-(3-cyanophenyl)ethane was used to alkylate Compound 1. The product obtained from the first step was then taken through the remaining steps described in Scheme 15 to give Example AO. 1-Bromo-(3-cyanophenyl)ethane was synthesized using a two-step procedure by first reducing 3-acetylbenzonitrile to 1-(3-cyanophenyl)-ethanol, followed by conversion to 1-bromo-(3-cyanophenyl)ethane. Examples AP, AQ, AR, and AS were prepared using procedures similar to those used to prepare Example AN (Scheme 16) by using an appropriate bromide in the first alkylation step. For compound AP, Na(CN)$_3$BH was used instead of Na(OAc)$_3$BH during the reductive amination. The structure and spectral data of these compounds are listed below.

Example AO

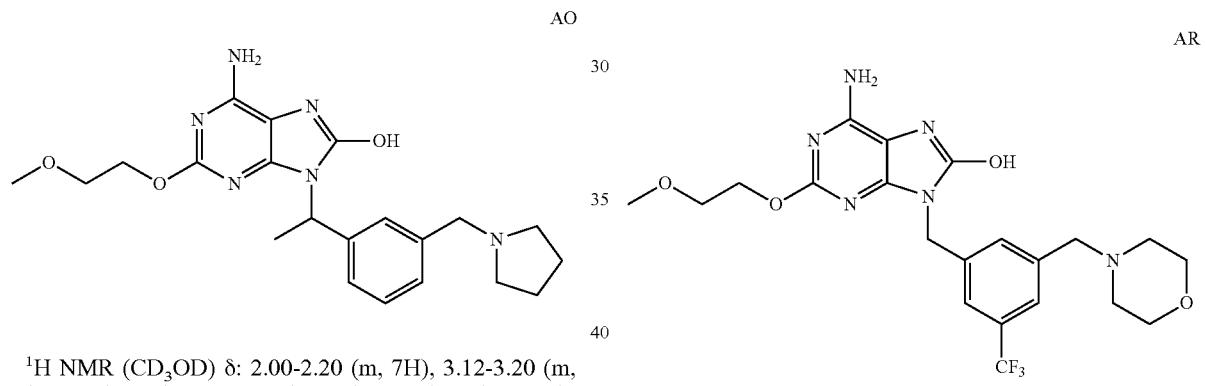

AO $^1$H NMR (CD$_3$OD) δ: 2.00-2.20 (m, 7H), 3.12-3.20 (m, 2H), 3.38 (S, 3H), 3.44-3.50 (m, 2H), 3.74 (t, 2H), 4.39 (s, 2H), 4.56-4.64 (m, 2H), 5.78 (q, 1H), 7.48-7.69 (m, 4H); MS: 413 (MH$^+$).

Example AP

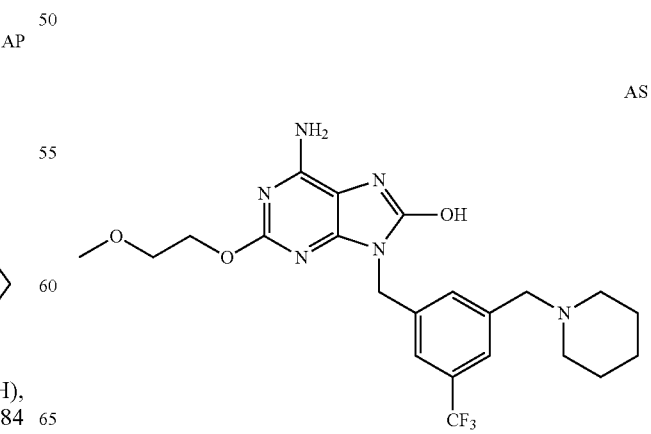

AP $^1$H NMR (CD$_3$OD) δ: 1.72 (d, 3H), 1.92-2.18 (m, 4H), 2.92-3.04 (m, 2H), 3.19-3.29 (m, 2H), 3.39 (s, 3H), 3.75-3.84 (m, 3H), 4.40 (q, 1H), 4.64-4.67 (m, 2H), 5.10-5.13 (m, 2H), 7.47-7.64 (m, 4H); MS: 413 (MH$^+$).

Example AQ

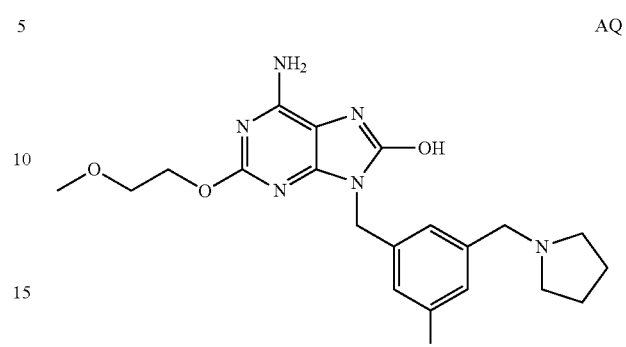

AQ $^1$H NMR (CD$_3$OD) δ: 2.00-2.05 (m, 2H), 2.08-2.19 (m, 2H), 3.16-3.21 (m, 2H), 3.38 (s, 3H), 3.47-3.52 (m, 2H), 3.74-3.77 (m, 2H), 4.49 (s, 2H), 4.65 (t, 2H), 5.20 (s, 2H), 7.90-7.92 (m, 3H); MS: 467 (MH$^+$).

Example AR

AR $^1$H NMR (CD$_3$OD) δ: 3.20-3.35 (m, 4H), 3.39 (s, 3H), 3.75-3.78 (m, 4H), 3.86-3.87 (m, 2H), 4.00-4.04 (m, 2H), 4.46 (s, 2H), 4.65-4.68 (m, 2H), 5.20 (s, 2H), 7.90-7.97 (m, 3H); MS: 483 (MH$^+$).

Example AS

AS

¹H NMR (CD₃OD) δ: 1.54-1.58 (m, 1H), 1.80-1.90 (m, 5H), 2.99 (t, 2H), 3.39 (s, 3H), 3.42 (s, 2H), 3.76 (m, 2H), 4.39 (s, 2H), 4.66 (t, 2H), 5.20 (2H), 7.87-7.93 (m, 3H); MS: 481 (MH⁺).

Examples AT, AU, AV, and AW were prepared using procedures similar to those used to prepare Example W except that NMP was used as the solvent and different alcohols were used instead of butanol. For Example AT, the first step was conducted at 200° C.

Example AT

AT

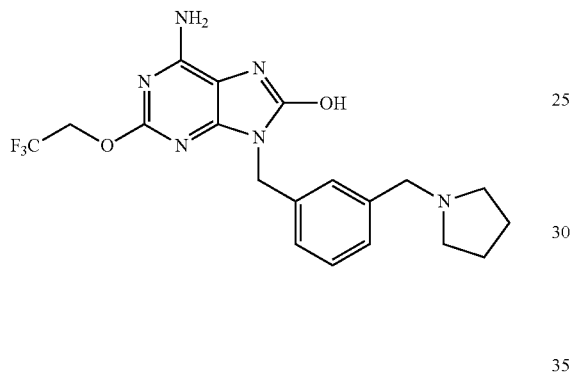

¹H NMR (DMSO) δ: 1.84-1.97 (m, 4H), 2.98-3.00 (m, 2H), 3.27-3.29 (m, 2H), 4.30 (dd, 2H), 4.80-4.90 (m, 4H), 7.33-7.54 (m, 4H); MS: 423 (MH⁺).

Example AU

AU

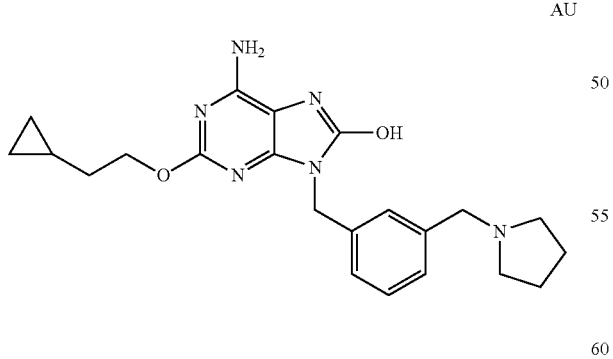

¹H NMR (DMSO) δ: 0.05-0.07 (m, 2H), 0.38-0.40 (m, 2H), 0.73-0.76 (m, 1H), 1.51-1.58 (m, 2H), 1.82-1.98 (m, 4H), 2.97-3.02 (m, 2H), 3.26-3.30 (m, 2H), 4.22-4.30 (m, 4H), 10.65 (s, 1H); MS: 409 (MH⁺).

Example AV

AV

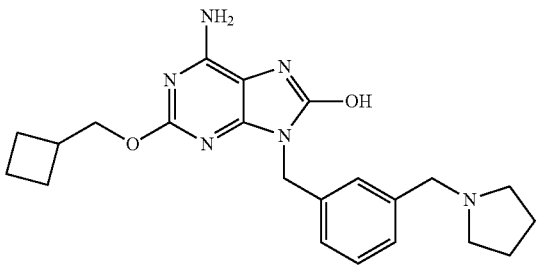

¹H NMR (CD₃OD) δ: 1.92-2.20 (m, 11H), 3.15-3.21 (m, 2H), 3.43-3.52 (m, 2H), 4.38 (s, 2H), 4.50 (d, 2H), 5.12 (s, 2H), 7.49-7.60 (m, 4H); MS: 409 (MH⁺).

Example AW

AW

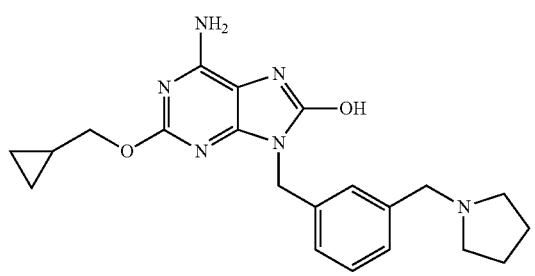

¹H NMR (DMSO) δ: 0.27-0.31 (m, 2H), 0.49-0.61 (m, 2H), 1.64-1.84 (m, 1H), 1.84-1.98 (m, 4H), 2.98-3.01 (m, 2H), 3.27-3.29 (m, 2H), 4.29-4.31 (m, 4H), 5.01 (s, 2H), 7.34-7.55 (m, 4H), 10.65 (s, 1H); MS: 395 (MH⁺).

Example AX

AX

Example AX was prepared using procedures similar to those used to prepare Example AC, except Compound 1 was replaced with Compound 6. ¹H NMR (DMSO) δ: 0.89 (t, J=7.5 Hz, 3H), 1.13 (t, J=7.2 Hz, 3H), 1.35 (sext, J=7.2 Hz, 2H), 1.63 (quint, J=7.5 Hz, 2H), 1.80-

2.02 (m, 4H), 2.91-3.04 (m, 2H), 3.20-3.31 (m, 2H), 4.00 (q, J=7.2 Hz, 2H), 4.21-4.30 (m, 4H), 4.94 (s, 2H), 7.00 (br, 2H), 7.30-7.58 (m, 4H), 11.23 (s, 1H); MS: 425 (MH⁺).

Examples AY, AZ and BA were prepared using the procedures similar to those used to prepare Example A, except that pyrrolidine was replaced with an appropriate amine. For example, pyrrolidine was replaced with cyclohexylmethanamine in Example AZ.

Example AY

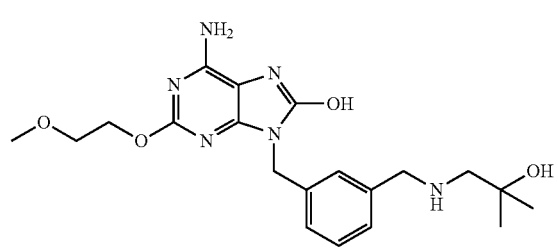

¹H NMR (DMSO) δ: 1.13 (s, 6H), 2.68-2.74 (m, 2H), 3.25 (s, 3H), 3.57 (t, J=4.5 Hz, 2H), 4.05-4.15 (m, 2H), 4.29 (t, J=4.5 Hz, 2H), 4.89 (s, 2H), 7.10 (br, 2H), 7.49-7.32 (m, 4H), 8.84 (br, 2H), 10.71 (s, 1H); MS: 417 (MH⁺).

Example AZ

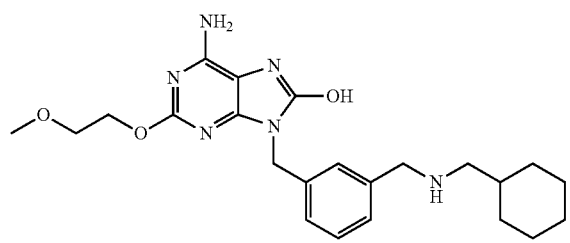

¹H NMR (DMSO) δ: 0.94-0.81 (m, 2H), 1.08-1.26 (m, 2H), 1.55-1.77 (m, 6H), 2.66-2.74 (m, 2H), 3.25 (s, 3H), 3.57 (t, J=4.5 Hz, 2H), 4.05-4.15 (m, 2H), 4.26 (t, J=4.5 Hz, 2H), 4.88 (s, 2H), 6.84 (br, 2H), 7.32-7.48 (m, 4H), 8.87 (br, 2H), 10.53 (s, 1H); MS: 441 (MH⁺).

Example BA

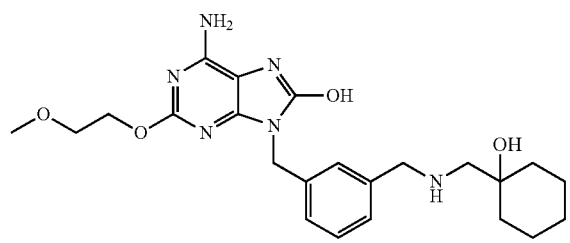

¹H NMR (DMSO) δ: 1.12-1.57 (m, 10H), 2.68-2.76 (m, 2H), 3.25 (s, 3H), 3.59 (t, J=4.5 Hz, 2H), 4.06-4.14 (m, 2H), 4.32 (t, J=4.5 Hz, 2H), 4.89 (s, 2H), 7.30 (br, 2H), 7.32-7.51 (m, 4H), 8.88 (br, 2H), 10.96 (s, 1H); MS: 457 (MH⁺).

Examples BB and BC were prepared using procedures similar to those used to prepare Example W, except that the appropriate amine was used for the different compounds.

Example BB

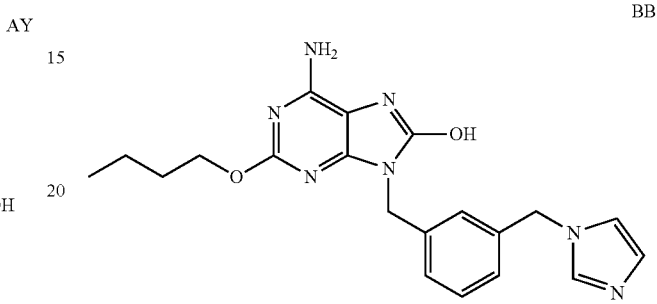

¹H NMR (DMSO) δ: 0.88 (t, J=7.2 Hz, 3H), 1.36 (sext, J=7.2 Hz, 2H), 1.64 (quint, J=6.6 Hz, 2H), 2.96-3.19 (m, 4H), 3.72-3.92 (m, 4H), 4.22-4.34 (m, 4H), 4.92 (s, 2H), 7.30 (br, 2H), 7.36-7.58 (m, 4H), 11.6 (s, 1H), 11.35 (br, 1H); MS: 314 (MH⁺).

Example BC

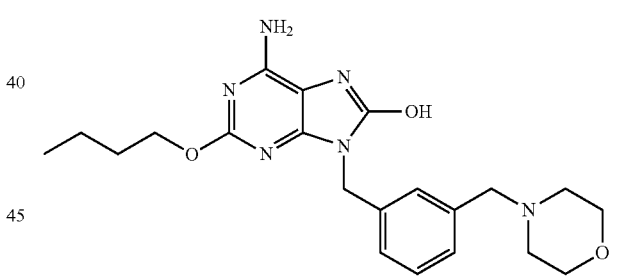

¹H NMR (DMSO) δ: 0.88 (t, J=7.2 Hz, 3H), 1.35 (sext, J=7.2 Hz, 2H), 1.62 (quint, J=6.6 Hz, 2H), 4.18 (t, J=6.6 Hz, 2H), 4.87 (s, 2H), 5.42 (s, 2H), 7.20 (br, 2H), 7.25-7.40 (m, 4H), 7.68 (s, 1H), 7.76 (s, H), 8.29 (s, 1H), 10.90 (s, 1H); MS: 394 (MH⁺).

Synthesis of Example BD

Scheme 17

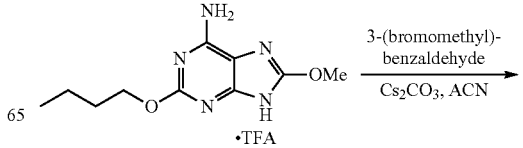

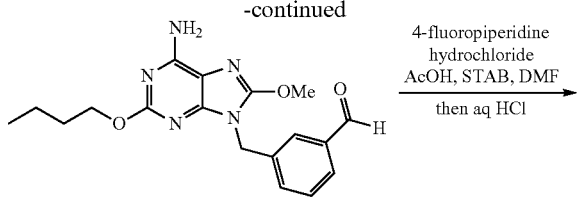

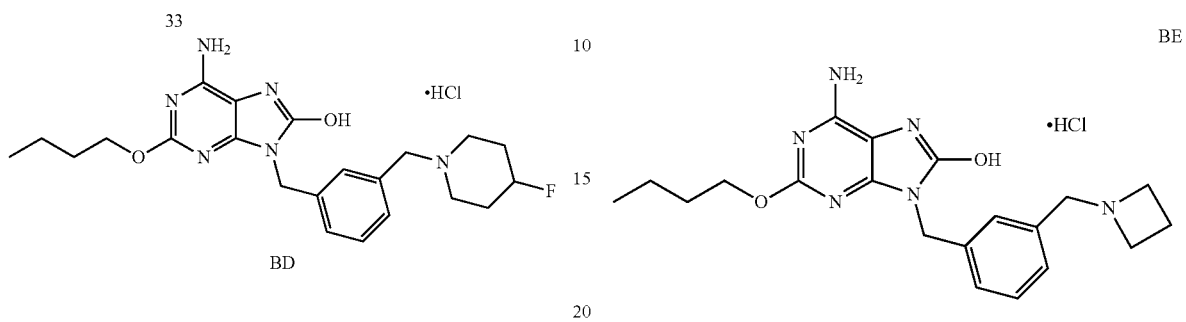

Compound 33

A sample of the 2-butoxy-8-methoxy-9H-purin-6-amine TFA salt (7.58 g) was dissolved in CH$_3$CN (400 mL) and treated with Cs$_2$CO$_3$ (21.1 g) at 23° C. for 5 min. 3-(bromomethyl)-benzaldehyde (4.27 g) was then added. Once the reaction was gauged complete using LCMS and HPLC, it was filtered through a plug of Na$_2$SO$_4$ over a glass frit. The filtrate was concentrated to an orange solid. A minimum of warm glacial AcOH (30 mL) was used to dissolve the solid with stirring in an oil bath at 80° C. H$_2$O (54 mL) was added slowly with mild stirring. Clouding was persistent, so the reaction was allowed to cool to 23° C. in the oil bath. An orange oil began to coagulate out of the mother liquor. More glacial AcOH (5 mL) was added, but the oil failed to resorb into the mother liquor. The mixture was cooled in a refrigerator overnight, and the orange oil solidified. The mother liquor was decanted away, and almost immediately, white crystals began to grow. These crystals proved to be 95% pure compound 33 (~1.5 g), which was captured via filtration. The orange solidified oil could be purified on silica gel (DCM:MeOH, 98:2, isocratic gradient), affording 90% pure 33 (yield not determined). $^1$H NMR (CDCl$_3$) δ: 0.97 (t, 3H), 1.46-1.55 (m, 2H), 1.73-1.81 (m, 2H), 4.11 (s, 3H), 4.31 (t, 2H), 5.18 (d, 4H), 7.47-7.60 (m, 2H), 7.79-7.86 (m, 2H), 9.99 (s, 1H); MS: 356 (MH$^+$).

Example BD

To a solution of aldehyde 33 (90 mg) in DMF (1.5 mL) was added 4-fluoropiperidine hydrochloride (106 mg). Glacial AcOH (90 μL) and NaBH(OAc)$_3$ (270 mg) were introduced, and the reaction was stirred at 23° C. for 1.5 h. Once the reaction was gauged complete using LCMS and HPLC analysis, 12 M aq HCl (300 μL) was added. The next day, 1.0 M aq HCl (1.0 mL) was added to aid conversion.

Once the reaction had reached completion, the entire reaction was directly purified on a C-18 reversed-phase HPLC column (eluent: 0.5% w/v aq HCl+CH$_3$CN; 5/90 to 100:0), giving amine BD (85.5 mg, 81% yield) as a yellow gum after lyophilization. $^1$H NMR (DMSO) δ: 0.89 (t, 3H), 1.32-1.38 (m, 2H), 1.57-1.63 (m, 2H), 1.90-2.12 (m, 5H), 3.07-3.21 (m, 4H), 4.12 (t, 2H), 4.28-4.32 (m, 2H), 4.89 (s, 2H), 7.36-7.44 (m, 4H), 10.04 (bs, 1H), 10.28 (s, 1H); MS: 429 (MH$^+$).

Examples BE and BF were prepared using procedures similar to those used to prepare Example BD, except that the appropriate amine was used for different examples and that the reductive amination step to make example BF was conducted at 80° C.

Example BE

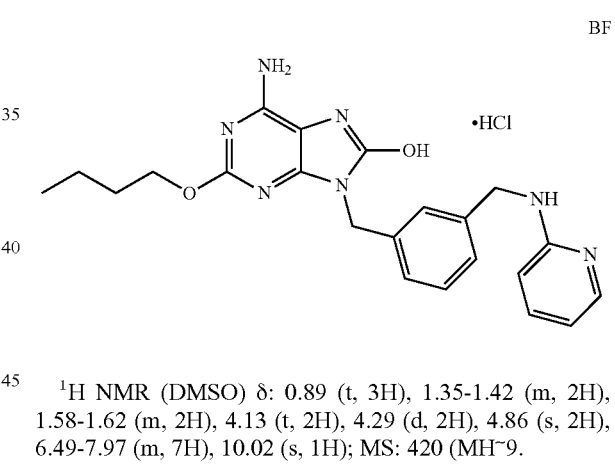

$^1$H NMR (DMSO) δ: 0.88 (t, 3H), 1.33-1.40 (m, 2H), 1.59-1.68 (m, 2H), 2.26-2.38 (m, 2H), 3.87-3.99 (m, 4H), 4.28 (t, 2H), 4.91 (s, 2H), 7.30-7.42 (m, 4H), 11.01 (bs, 1H), 11.13 (s, 1H); MS: 383 (MH$^+$).

Example BF

BF $^1$H NMR (DMSO) δ: 0.89 (t, 3H), 1.35-1.42 (m, 2H), 1.58-1.62 (m, 2H), 4.13 (t, 2H), 4.29 (d, 2H), 4.86 (s, 2H), 6.49-7.97 (m, 7H), 10.02 (s, 1H); MS: 420 (MH$^-$9.

Synthesis of Example BG

Scheme 18

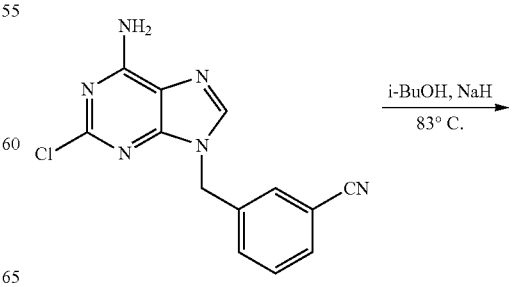

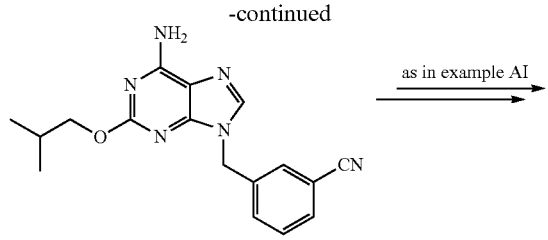

34

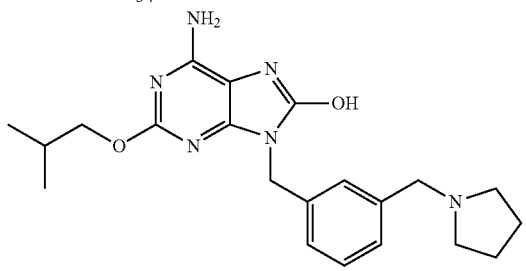

BG

Compound 34

Sodium Hydride (170 mg) was added to an excess of isobutanol (10 mL) until completely dissolved. Nitrile 12 (1.26 g) was added and the mixture stirred at 83° C. overnight. The mixture was poured onto icy water with 2 mL of glacial HOAc and stirred for 5 minutes. Extract with EtOAc (3×100 mL), dry with Na$_2$SO$_4$ and concentrate. Chromatography on silica gel using ISCO combiflash on a 40G column using solid loading and a DCM/20% MeOH in DCM eluent performed with a 4-40% gradient over 10 column volumes gave isobutyl ether 34 (333 mg). (The product was a mixture with corresponding ester from reduction of nitrile which was carried forward and removed later in the reaction sequence). MS: 323 (MH$^+$).

Example BG was prepared from Compound 34 using procedures similar to those used to prepare Example AI.

1H NMR (300 MHz, d$^6$ DMSO) δ: 0.91-0.93 (d J=6.6 Hz, 6H); 1.81-2.04 (m, 5H); 3.00 (m, 2H); 3.28 (m, 2H); 3.98-4.01 (d J=6.6 Hz, 2H); 4.28-4.31 (d J=6.3 Hz, 2H); 4.91 (s, 2H); 7.34-7.45 (m, 3H); 7.51-7.53 (d J=7.2 Hz, 1H) 10.75, (bs, 1H); 10.92 (s, 1H). MS: 397 (MH$^+$).

Example BH was prepared using procedures similar to those used to prepare Example BG, except that 3,3,3-trifluoropropan-1-ol was used in the first step and that the mixture reacted in a sealed tube at 94° C. for 2.5 h.

BH

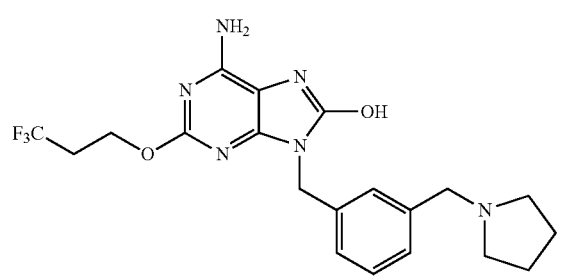

$^1$H NMR (300 MHz, d$^6$ DMSO) δ: 1.82-1.98 (bd, 8H); 2.68-2.76 (m, 2H); 3.02 (bm, 2H); 3.29 (bm, 2H); 4.29-4.37 (ddd, 4H); 4.90 (s, 2H), 7.36-7.50 (m, 4H); 10.40 (bs, 1H); 10.53 (s, 1H); MS: 437 (MH$^+$).

Synthesis of Example BI

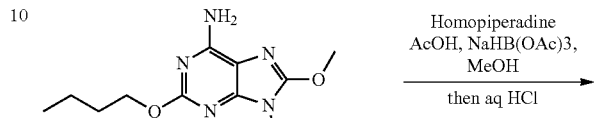

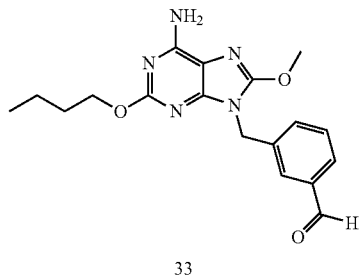

33

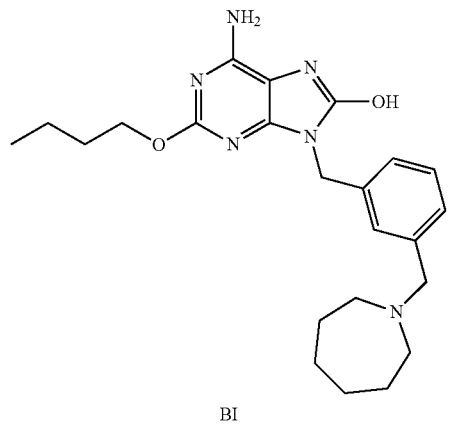

BI

To a solution of aldehyde 33 (230 mg) in MeOH (~10 mL) was added homopiperidine (aka hexamethyleneimine) (270 µL). Glacial AcOH (100 µL) and NaHB(OAc)$_3$ (307 mg) were introduced, and the reaction was stirred at 23° C. for 12 hrs. Once the reaction was determined to be complete using LCMS and HPLC analysis, the crude Schiff base was purified by PREP HPLC. All product fractions were combined, neutralized with an excess of K$_2$CO$_3$, concentrated to remove acetonitrile, and extracted with EtOAc (3×30 mL). The combined organic extracts were dried with Na$_2$SO$_4$ and concentrated to a solid in vacuo. The resulting solid was dissolved in minimal CH$_3$CN and conc. HCl (900 µA) was added and stirred at 23° C. for 30 minutes, then the entire reaction was directly purified on a Preparative C-18 reversed-phase HPLC column (eluent: 0.5% w/v aq HCl+CH$_3$CN; 1-40% CH$_3$CN in water over 20 minutes), giving amine Example BI (18 mg) as a lyophilized HCl salt. 1H NMR (300 MHz, d$^6$ DMSO) δ: 0.89 (t, 3H), 1.32-1.40 (m, 2H), 1.54-1.64 (m, 6H), 1.75-1.77 (m, 4H), 2.98-3.03 (m, 2H), 3.21-3.26 (m, 2H), 4.18 (t, 2H), 4.27 (d, 2H), 7.35-7.54 (m, 4H), 10.22 (bs, 1H), 10.71 (S, 1H); MS: 425 (MH$^+$).

Example BJ was prepared using procedures similar to those used to prepare Example BG, except that tetrahydrofuran-3-ol was used in the first step and the reaction mixture was reacted at 94° C. for 2 hrs.

BJ

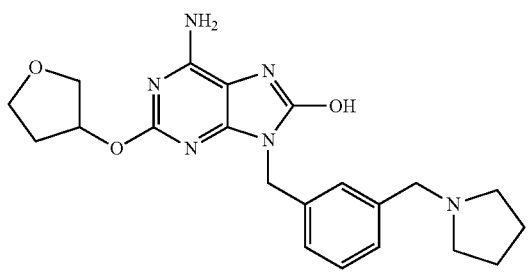

¹H NMR (300 MHz, d⁶ DMSO) δ: 1.81-1.98 (bd, 8H); 2.09-2.21 (m, 2H); 3.01 (bm, 2H); 3.31 (bm, 2H); 3.66-3.88 (m, 4H); 4.29-4.31 (d J=6.0 Hz, 2H); 4.89, (s, 2H); 5.27 (bm, 1H); 7.35-7.50 (m, 4H); 10.45 (bs, 1H); 10.59 (s, 1H); MS: 410 (MH⁺).

Example BK was prepared using procedures similar to those used to prepare Example BG, except that (tetrahydrofuran-2-yl)methanol was used in the first step and that the reaction mixture reacted in a sealed tube at 94° C. for 2 hrs.

BK

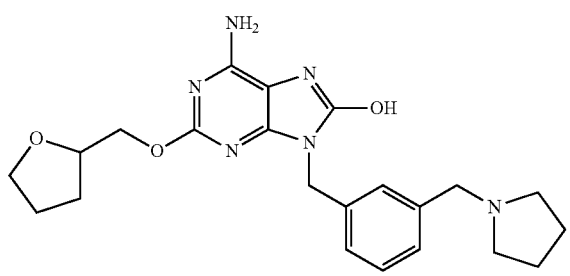

¹H NMR (300 MHz, d⁶ DMSO) δ: 1.58-2.01 (m, 8H), 2.87-3.17 (m, 2H), 3.37-3.35 (m, 2H), 3.60-3.77 (m, 2H), 4.04-4.14 (m, 3H), 4.30 (d, 2H), 4.90 (s, 2H), 7.24-7.50 (m, 4H), 10.20 (bs, 1H), 10.39 (s, 1H); MS: 425 (MH⁺).

Example BL was prepared using procedures similar to those used to prepare Example BG, except that 2,2,3,3,3-pentafluoropropanol was used in the first step and that the reaction mixture reacted in a sealed tube at 95° C. for 9 hrs.

BL

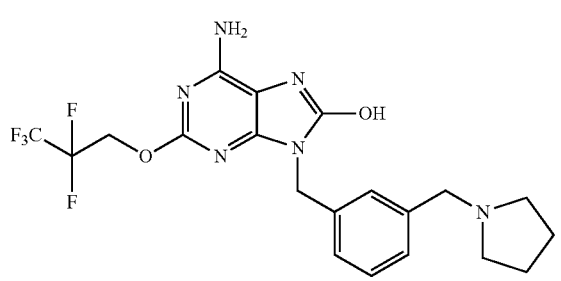

¹H NMR (300 MHz, d⁶ DMSO) δ: 1.80-1.99 (m, 4H), 3.01-3.18 (m, 2H), 3.27-3.32 (m, 2H), 4.30 (d, 2H), 4.91-4.99 (m, 4H), 7.33-7.52 (m, 4H), 10.48 (bs, 1h), 10.69 (s, 1H); MS: 472 (MH⁺).

Example BM was prepared using procedures similar to those used to prepare Example BG, except that cyclopentanol was used in the first step.

BM

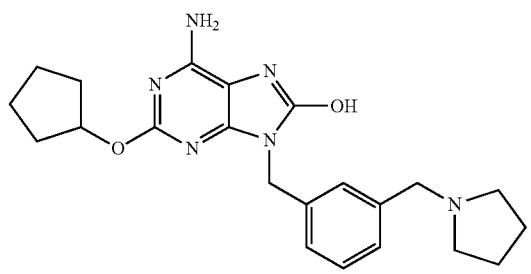

¹H NMR (300 MHz, DMSO) δ: 1.54-1.67 (m, 6H), 1.82-1.98 (m, 6H), 3.01 (m, 2H), 3.29 (m, 2H), 4.29-4.31 (d, 2H), 4.89 (s, 2H), 5.32 (m, 1H), 7.35-7.56 (m, 4H), 10.49 (bs, 1H), 10.63 (s, 1H); MS: 409 (MH⁺).

Example BN was prepared using procedures similar to those used to prepare Example A, except that Compound 2 was reacted directly with 1-methylpiperazine (i.e., bromination of the 8-position of the puring ring was not carried out).

BN

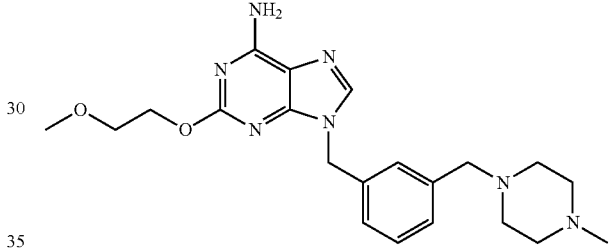

¹H NMR (DMSO) δ: 8.04 (s, 1H), 7.33-7.17 (m, 6H), 5.24 (s, 2H), 4.31 (t, J=4.5 Hz, 2H), 3.60 (t, J=4.5 Hz, 2H), 3.46 (s, 2H), 3.27 (s, 3H), 2.75-2.30 (m, 8H), 2.40 (s, 3H). MS: 412 (MH⁺)

Similarly, Example BO was prepared using procedures similar to those used to prepare Example A, except that Compound 2 was reacted directly with pyrrolidine (and bromination of the 8-position of the puring ring was not carried out).

BO

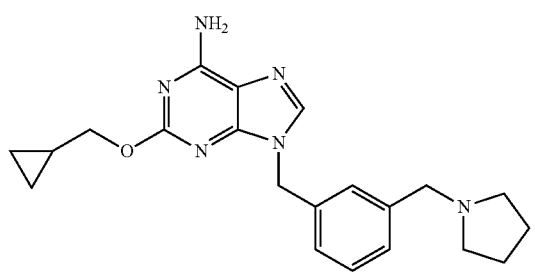

¹H NMR (DMSO) δ: 0.33-0.34 (m, 2H), 0.51-0.55 (m, 2H), 1.20-1.23 (m, 1H), 1.81-1.96 (m, 4H), 2.96-3.01 (m, 2H), 3.25-3.28 (m, 2H), 4.15-4.29 (m, 4H), 5.37 (s, 2H), 7.40-7.59 (m, 4H), 8.54 (s, 1H); MS: 379 (MH⁺).

Examples BP, BQ, BR, BS, and BT were prepared using procedures similar to those used to prepare Example A except that pyrrolidine was replaced with the appropriate amine for each of these examples.

BP

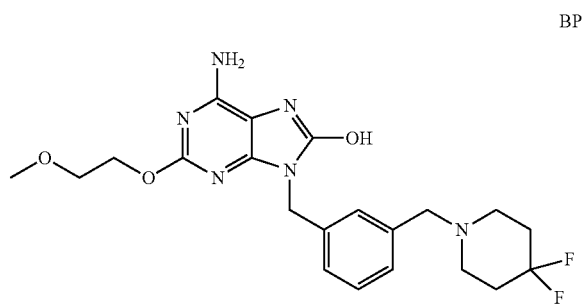 [SMILES: COCCOc1nc(N)c2nc(O)n(Cc3cccc(CN4CCC(F)(F)CC4)c3)c2n1]

¹H NMR (DMSO) δ: 11.23 (br, 1H), 10.69 (s, 1H), 7.54-7.36 (m, 4H), 7.10 (br, 2H), 4.87 (s, 2H), 4.32 (s, 2H), 4.27 (t, J=4.5 Hz, 2H), 3.56 (t, J=4.5 Hz, 2H), 3.40-3.30 (m, 2H), 3.23 (s, 3H), 3.12-3.01 (m, 2H), 2.50-2.22 (m, 4H). MS: 449 (MH⁺)

BQ

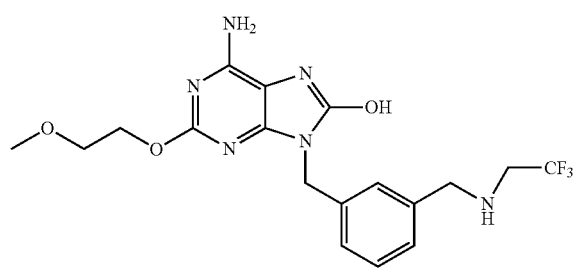

¹H NMR (DMSO) δ: 10.63 (s, 1H), 9.94 (br, 2H), 7.49-7.34 (m, 4H), 6.94 (br, 2H), 4.89 (s, 2H), 4.27 (t, J=4.5 Hz, 2H), 4.19 (s, 2H), 3.99 (q, J=18.9 Hz, 2H), 3.57 (t, J=4.5 Hz, 2H), 3.25 (s, 3H). MS: 427 (MH⁺)

BR

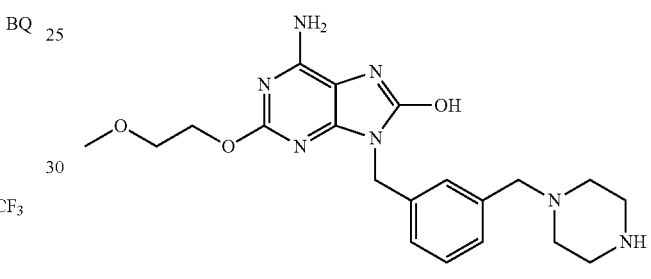

¹H NMR (DMSO) δ: 10.80 (s, 1H), 9.79 (br, 2H), 7.56-7.43 (m, 4H), 7.05 (br, 2H), 4.92 (s, 2H), 4.68-4.58 (m, 2H), 4.28 (t, J=4.5 Hz, 2H), 3.83-3.45 (m, 8H), 3.27 (s, 3H), 3.22-3.13 (m, 2H), 2.99 (s, 3H), 2.20-2.12 (m, 2H). MS: 442 (MH⁺)

BS

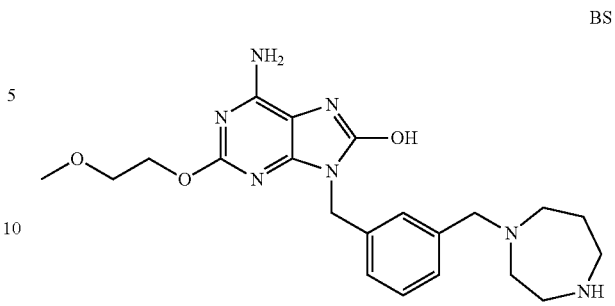

¹H NMR (DMSO) δ: 11.41 (br, 1H), 10.75 (s, 1H), 9.58 (br, 1H), 9.42 (br, 1H), 7.60-7.34 (m, 4H), 7.10 (br, 2H), 4.89 (s, 2H), 4.35 (s, 2H), 4.30 (t, J=4.5 Hz, 2H), 3.58 (t, J=4.5 Hz, 2H), 3.68-3.10 (m, 8H), 3.26 (s, 3H), 2.18-2.10 (m, 2H). MS: 428 (MH⁺)

BT

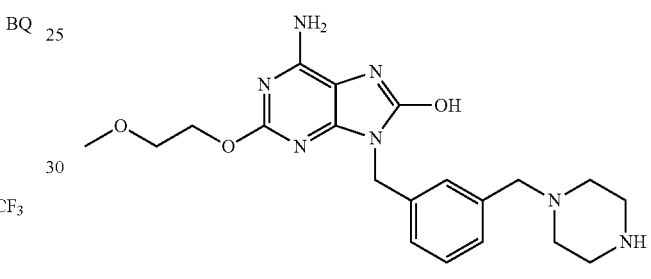

¹H NMR (DMSO) δ: 11.95 (br, 1H), 10.88 (s, 1H), 9.69 (br, 2H), 7.60-7.35 (m, 4H), 7.20 (br, 2H), 4.90 (s, 2H), 4.38 (s, 2H), 4.32 (t, J=4.5 Hz, 2H), 3.59 (t, J=4.5 Hz, 2H), 3.55-3.10 (m, 8H), 3.26 (s, 3H). MS: 414 (MH⁺)

Examples BU and BV were prepared using procedures similar to those used to prepare Example AC except that bis(cyclopropylmethyl) amine or cyclopropylmethanamine was used instead of pyrrolidine.

BU

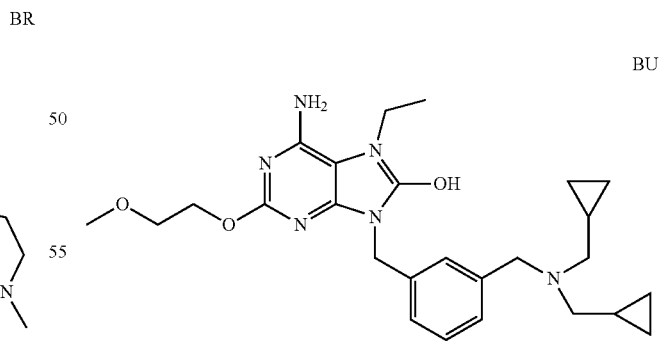

¹H NMR (DMSO) δ: 10.46 (br, 1H), 7.60-7.33 (m, 4H), 6.80 (br, 2H), 4.93 (s, 2H), 4.39 (d, J=4.5 Hz, 2H), 4.29 (t, J=4.8 Hz, 2H), 3.98 (q, J=6.6 Hz, 2H), 3.58 (t, J=4.5 Hz, 2H), 3.26 (s, 3H), 3.05-2.84 (m, 4H), 1.12 (t, J=6.9 Hz, 3H), 1.20-1.05 (m, 2H), 0.62-0.53 (m, 4H), 0.38-0.28 (m, 4H). MS: 481 (MH⁺)

BV

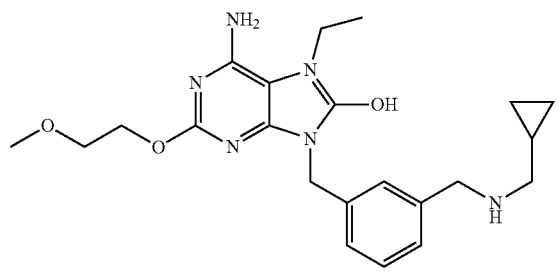

¹H NMR (DMSO) δ: 9.14 (br, 2H), 7.50-7.28 (m, 4H), 6.71 (br, 2H), 4.92 (s, 2H), 4.27 (t, J=4.5 Hz, 2H) 4.05-3.93 (m, 4H), 3.58 (t, J=4.5 Hz, 2H), 3.26 (s, 3H), 2.82-2.72 (m, 2H), 1.13 (t, J=6.9 Hz, 3H), 1.15-1.00 (m, 1H), 0.58-0.51 (m, 2H), 0.35-0.29 (m, 2H). MS: 427 (MH$^+$)

Example BW was prepared using procedures similar to those used to prepare Example AC except that 4-(bromomethyl)benzonitrile is used to alkylate Compound 1 instead of 3-(bromomethyl)benzonitrile, and subsequently, the corresponding analog of Compound 8 was hydrolyzed to 4-((6-amino-8-hydroxy-2-(2-methoxyethoxy)-9H-purin-9-yl)methyl)benzonitrile without reaction with ethyl iodide, and the corresponding 4-((6-amino-8-hydroxy-2-(2-methoxyethoxy)-9H-purin-9-yl)methyl)benzaldehyde was the reacted with pyrrolidine.

BW

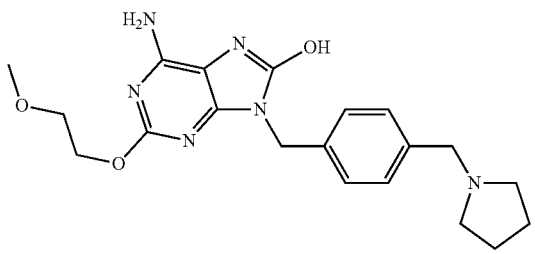

¹H NMR (300 MHz, DMSO) δ: 1.82-1.99 (m, 4H), 3.01-3.03 (m, 2H), 3.24-3.28 (m, 5H), 3.59 (t, 2H), 4.28-4.31 (m, 4H), 4.90 (s, 2H), 7.34-7.55 (m, 4H), 10.59 (bs, 2H); MS: 399 (MH$^+$).

TLR7Reporter Assay Protocol

A. HEK293 Assay

1. Cell Culture:

HEK293 cells stably transfected with the human TLR7 gene and a pNiFty™ NF-kB inducible luciferase reporter plasmid were obtained from Invivogen (San Diego, Calif.). DMEM/F12 medium, fetal bovine serum (FBS), Penicillin-Streptomycin (Pen-Strep), Blasticidin and Zeocine were from Invitrogen (Carlsbad, Calif.). The HEK293/TLR7/Luciferase cell line was constructed by transfecting stably the HEK293/TLR7 cells with the pNiFty plasmid. Cells were grown in the DMEM/F12 medium with 10% heat-inactivated FBS, supplemented with 1×Pen-Strep, 10 μg/mL Blasticidin and 5 μg/mL Zeocin.

2. Assay Procedure:

For the determination of the EC50 and Emax values of TLR7 agonists in the reporter assay, 20 μA of 2× test concentration of serial diluted compound in cell culture medium was added to each well of a white, clear-bottomed 384-well cell culture plate from Corning (Corning, N.Y.). To this plate, 20 μA of cell culture medium containing 12,000 HEK293/TLR7/Luciferase cells was dispensed to each well. The plate was then placed in incubator (37° C. and 5% $CO_2$) and incubated for 2 days. After the incubation, 40 μA of the pre-mixed lysis buffer/luciferase substrate solution was dispensed into each well. The lysis buffer (5×) and luciferase substrate was obtained from Promega (Madison, Wis.) and they were mixed at 2:3 (v/v) ratio immediately prior to use. After 10 minutes of incubation at room temperature, the luminescence signal was measured using a VictorLight plate reader (Perkin Elmer, Wellesley, Mass.) with an integration time of 0.1 seconds per sample.

Data analysis was performed with Prism software from GraphPad (San Diego, Calif.) using a single site binding algorithm. The maximum signal for each test compound ($E_{max}$) was normalized with the maximum signal for the positive control, Resiquimod, on each plate. The concentration of a compound that corresponds to 50% of the maximum signal is defined as the $EC_{50}$.

The compounds of the present invention have HCV EC50 values (μM) in the range of about 0.01 to about 1000, or about 0.1 to about 500, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10.

B. PBMC Assay

Assays were conducted to determine cytokine stimulation at 24 hours from human Peripheral Blood Mononuclear Cell (PMBC) using the compounds of the present invention. The assays were run in duplicate, with 8-point, half-log dilution curves. The compounds of the present invention were diluted from 10 μM DMSO solution. Cell supernatants are assayed directly for IFNα and 1:10 dilution for TNFα. The assays were performed in a similar fashion as described in Bioorg. Med. Chem. Lett. 16, 4559, (2006). Specifically, cryo-preserved PBMCs were thawed and seeded 96 well plates with 750,000 cells/well in 190 μL/well cell media. The PBMCs were then incubated for 1 hour at 37° C. at 5% $CO_2$. Then, the compounds of the present invention were added in 10 μL cell media at 8 point, half-log dilution titration. The plates were incubated at 37° C. and 5% $CO_2$ for 24 hours and then spinned at 1200 rpm for 10 min, which was followed by collecting supernatant and storing the same at −80° C. Cytokine secretion was assayed with Luminex and Upstate multi-plex kits, using a Luminex analysis instrument. IFN ECmax value for a compound was the concentration at which the compound stimulated maximum IFN a production as determined using the assay method above.

The compounds of the present invention have IFN ECmax values (nM) in the range of about 0.1 to about 10,000, or about 0.1 to about 1,000, or about 0.1 to about 300, or about 0.1 to about 100, or about 0.1 to about 10, or about 0.1 to about 5, or about 0.1 to about 1, or less than about 5000, or less than about 3000, or less than about 1000, or less than about 500, or less than about 400, or less than about 300, or less than about 200, or less than about 100, or less than about 50, or less than about 20, or less than about 10, or less than about 5, or less than about 1. Examples A, C, D, F, J, N, R, W, Y, AI, AJ, AQ, AS, AU, AV, AW, AZ, BE, BG, BH, and BM have IFN ECmax values (nM) of less than about 5.

What is claimed:

1. A compound represented by Formula Ia:

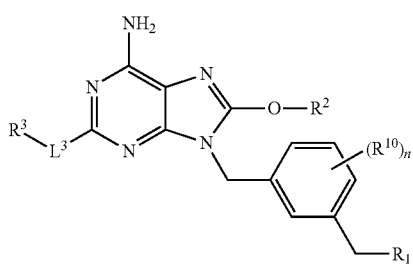

or a pharmaceutically acceptable salt thereof, wherein:

$R^1$ is selected from the group consisting of

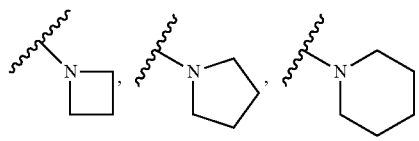

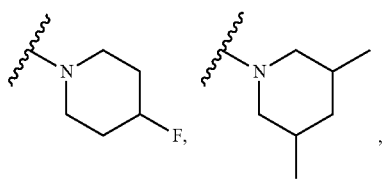

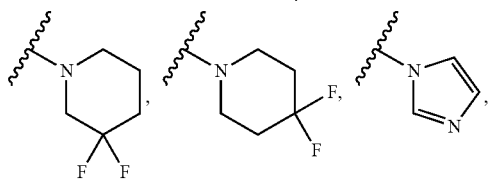

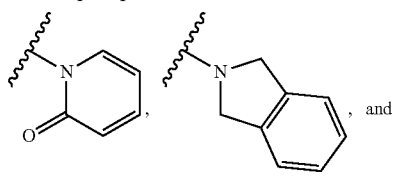

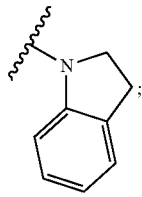

$R^2$ is H;

-$L^3$-$R^3$ is —OCH$_2$CH$_2$OCH$_3$, —OCH$_2$CH$_2$CH$_3$, —OCH$_2$CH$_2$CH$_2$CH$_3$, —O-i-butyl, —O-cyclobutyl, —O-cyclopentyl, —OCH$_2$-cyclopropyl, —OCH$_2$-cyclobutyl, —OCH$_2$CH$_2$-cyclopropyl, —OCH$_2$CH$_2$CH$_2$CH$_2$OH, —OCH$_2$CF$_3$, —OCH$_2$CH$_2$CF$_3$, —OCH$_2$CH$_2$CH$_2$CF$_3$, or (tetrahydrofuran-2-yl)methoxy;

$R^{10}$ is halogen, methoxy, —CF$_3$ or hydroxyl; and n is an integer from 0 to 1.

2. The compound of claim 1, wherein $R^1$ is selected from the group consisting of:

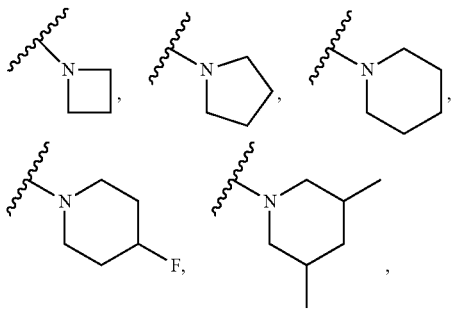

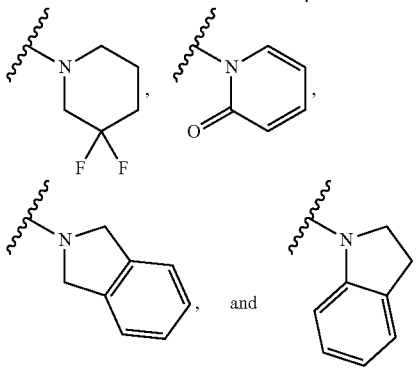

3. The compound of claim 1, wherein $R^1$ is selected from the group consisting of:

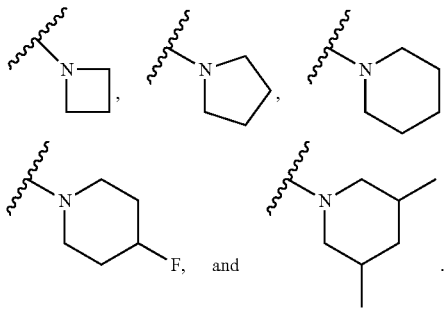

4. The compound of claim 1 wherein -$L^3$—$R^3$ is —OCH$_2$CH$_2$CH$_2$CH$_3$, —OCH$_2$CH$_2$OCH$_3$, —OCH$_2$CH$_2$CF$_3$, —OCH$_2$CH$_2$CH$_2$CH$_2$OH, or —OCH$_2$-cyclopropyl.

5. The compound of claim 1 selected from the group consisting of:

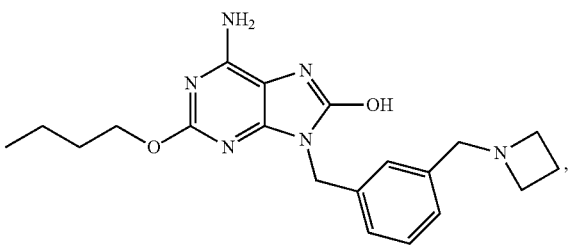

123
-continued
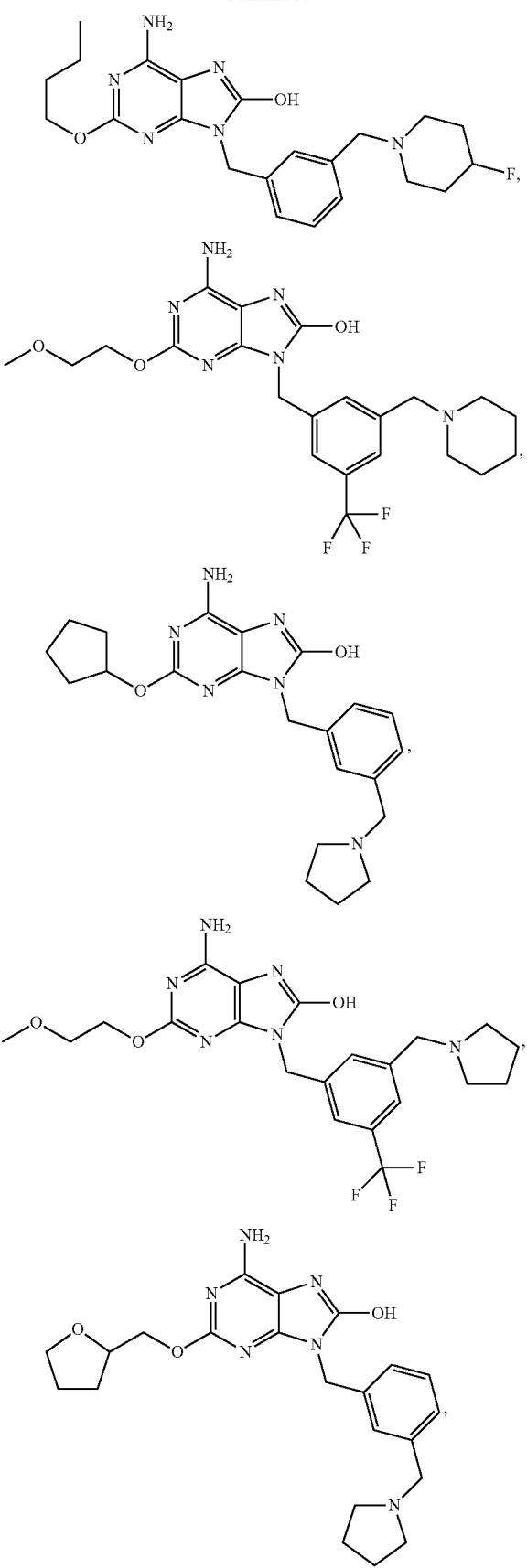
124
-continued
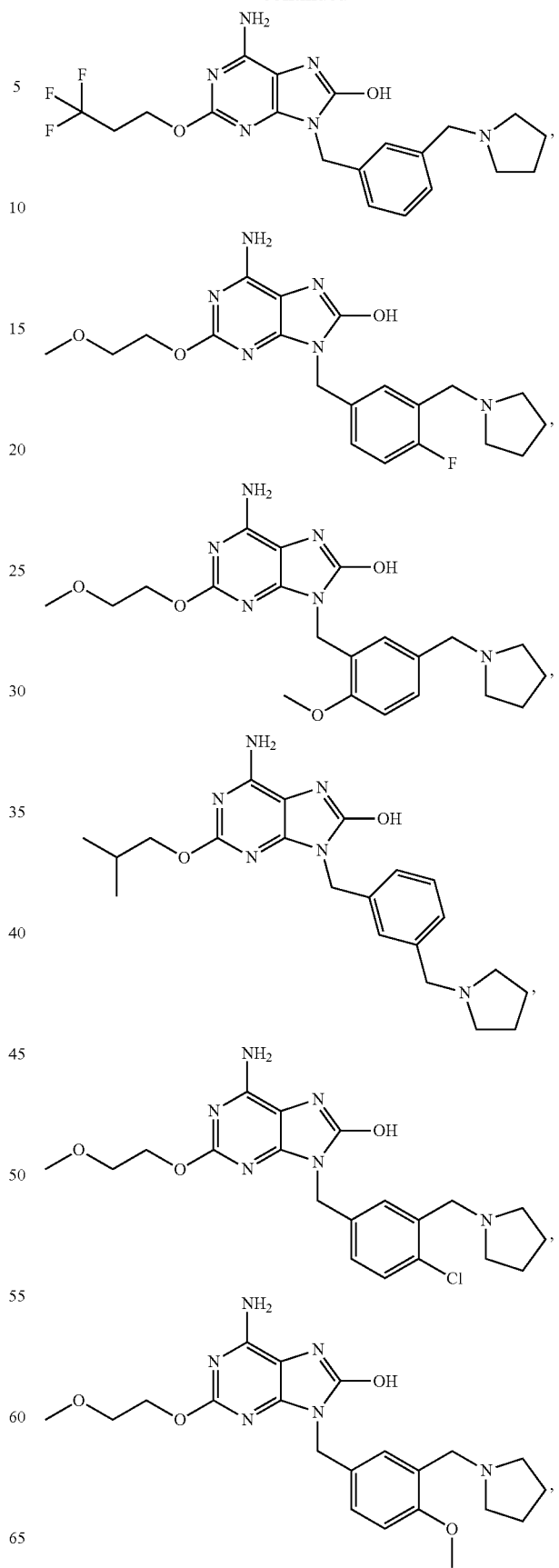

125
-continued
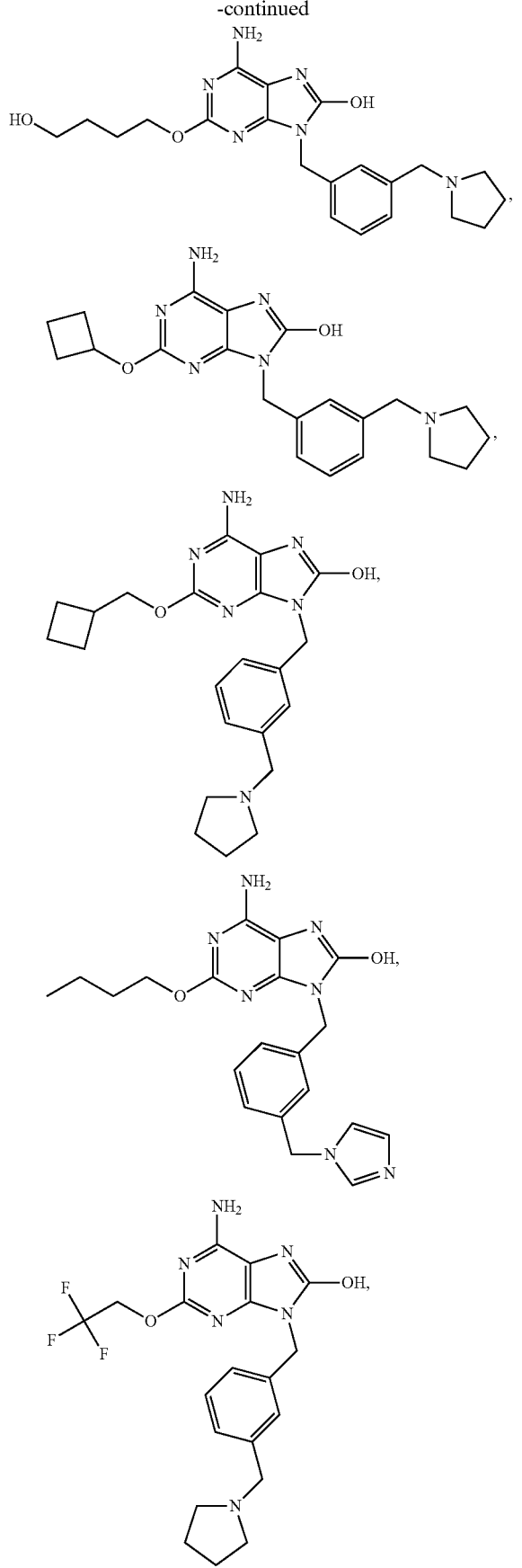
126
-continued
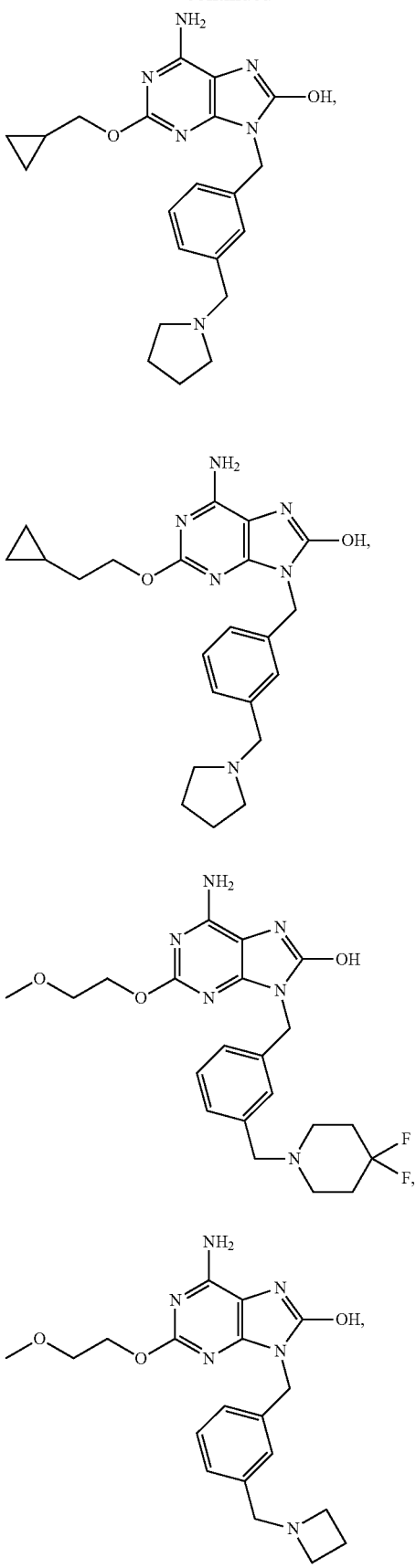

127
-continued
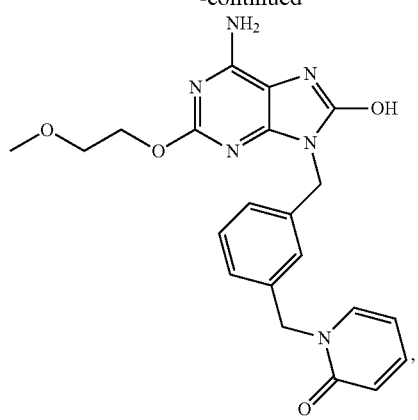
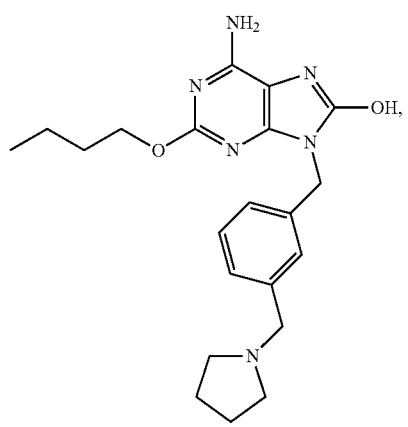
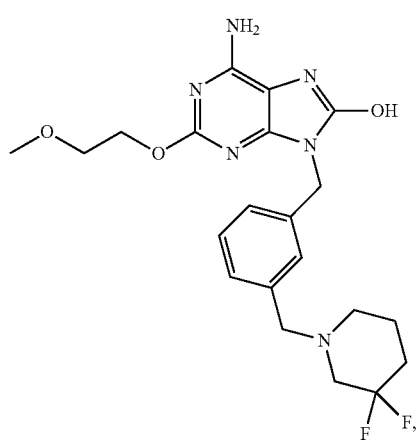
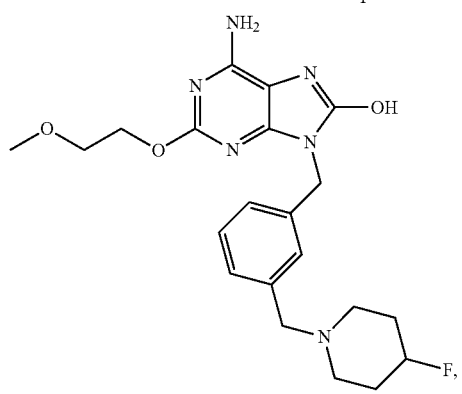
128
-continued
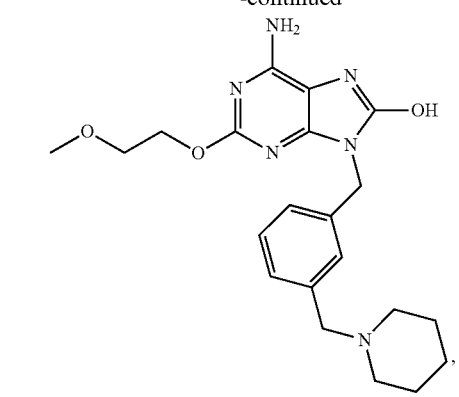
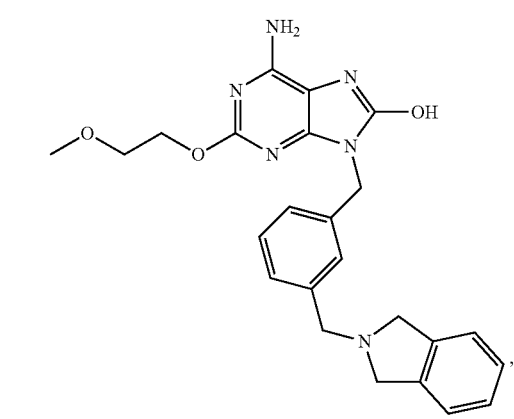
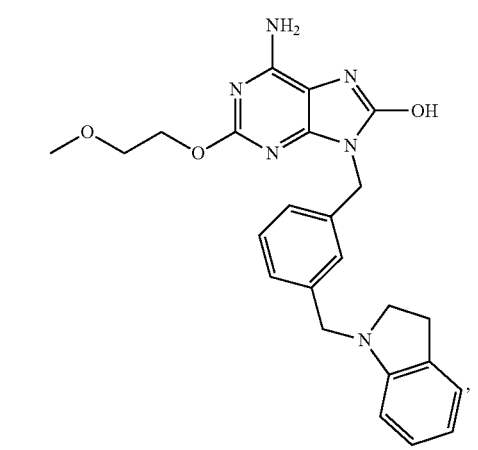
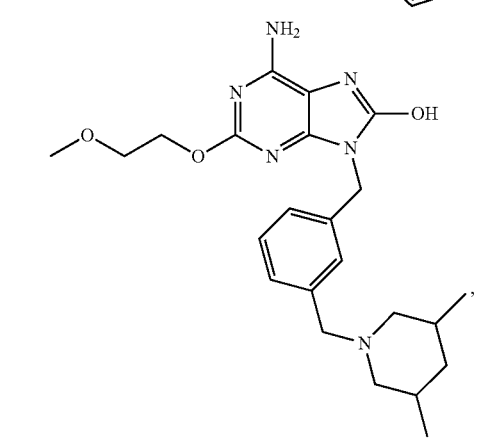

-continued
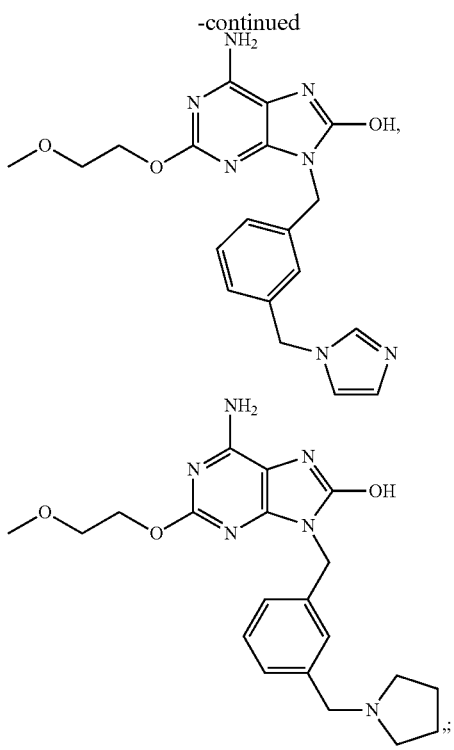
or pharmaceutically acceptable salts thereof.
6. The compound of claim 1 wherein -L³—R³ is —OCH₂CH₂CH₂CH₃.
7. The compound of claim 1 wherein R¹ is selected from the group consisting of:
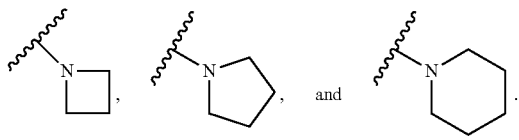 [SMILES: *N1CCC1 ; *N1CCCC1 ; *N1CCCCC1]
8. The compound of claim 1 is:
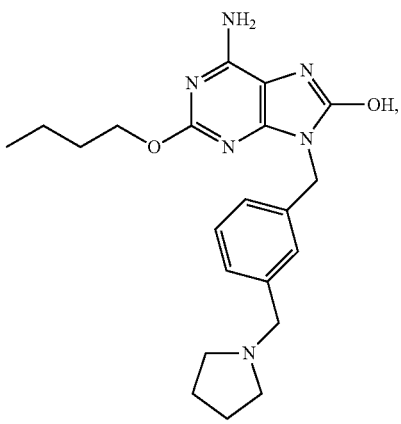 [SMILES: CCCCOc1nc(N)c2nc(O)n(Cc3cccc(CN4CCCC4)c3)c2n1]
or a pharmaceutically acceptable salt thereof.
* * * * *